US008188301B2

(12) United States Patent
Sonesson et al.

(10) Patent No.: US 8,188,301 B2
(45) Date of Patent: May 29, 2012

(54) DISUBSTITUTED PHENYLPYRROLIDINES AS MODULATORS OF CORTICAL CATECHOLAMINERGIC NEUROTRANSMISSION

(75) Inventors: Clas Sonesson, Billdal (SE); Lars Swanson, Öjersjö (SE); Fredrik Pettersson, Göteborg (SE); Nicholas Waters, Göteborg (SE); Susanna Waters, Göteborg (SE)

(73) Assignee: NSAB, Filial af NeuroSearch Sweden AB, Sverige, Ballerup (DK)

( * ) Notice: Subject to any disclaimer, the term of this patent is extended or adjusted under 35 U.S.C. 154(b) by 0 days.

(21) Appl. No.: 12/663,223

(22) PCT Filed: Jun. 4, 2008

(86) PCT No.: PCT/EP2008/056915
§ 371 (c)(1),
(2), (4) Date: Dec. 4, 2009

(87) PCT Pub. No.: WO2008/148801
PCT Pub. Date: Dec. 11, 2008

(65) Prior Publication Data
US 2010/0179211 A1    Jul. 15, 2010

Related U.S. Application Data

(60) Provisional application No. 60/941,994, filed on Jun. 5, 2007.

(30) Foreign Application Priority Data

Jun. 5, 2007 (SE) ...................................... 0701387

(51) Int. Cl.
*C07D 207/10* (2006.01)
*C07D 277/20* (2006.01)
*C07D 263/30* (2006.01)
*C07D 405/00* (2006.01)
*C07D 239/02* (2006.01)
*A61K 31/40* (2006.01)
*A61K 31/425* (2006.01)
*A61K 31/42* (2006.01)
*A01N 43/54* (2006.01)

(52) U.S. Cl. ........ 548/577; 548/202; 548/235; 548/517; 544/334; 514/424; 514/429; 514/256; 514/365; 514/374; 514/422

(58) Field of Classification Search .................... None
See application file for complete search history.

(56) References Cited

U.S. PATENT DOCUMENTS

| 2,878,264 A | 3/1958 | Lunsford |
| 3,118,907 A | 1/1964 | Yao et al. |
| 3,634,441 A | 1/1972 | Weistead et al. |
| 3,644,414 A | 2/1972 | Helsley |
| 5,128,362 A | 7/1992 | DeBernardis et al. |
| 2002/0169155 A1 | 11/2002 | Luly et al. |
| 2005/0070549 A1 | 3/2005 | Luly et al. |
| 2006/0052363 A1 | 3/2006 | Ablordeppey et al. |
| 2007/0105901 A1 | 5/2007 | Ohtake et al. |

FOREIGN PATENT DOCUMENTS

| DE | 1144279 B | 2/1963 |
| DE | 2017255 A1 | 10/1970 |
| EP | 0325983 A1 | 8/1989 |
| EP | 586229 A1 * | 3/1994 |
| EP | 1669350 A1 | 6/2006 |
| GB | 1202747 A | 8/1970 |
| WO | WO 92/18475 A2 | 10/1992 |
| WO | WO 97/24325 A1 | 7/1997 |
| WO | WO 00/05225 A1 | 2/2000 |
| WO | WO 00/70531 A2 | 11/2000 |
| WO | WO 01/16136 A2 | 3/2001 |
| WO | WO 01/46146 A1 | 6/2001 |
| WO | WO 2005/028438 A1 | 3/2005 |
| WO | WO 2005/121092 A1 | 12/2005 |
| WO | WO 2006/112685 A1 | 10/2006 |
| WO | WO 2006/117669 A1 | 11/2006 |
| WO | WO 2007/053145 A1 | 5/2007 |
| WO | WO 2007/071646 A1 | 6/2007 |
| WO | WO 2008/148799 A1 | 12/2008 |
| WO | WO 2008/148801 A2 | 12/2008 |

OTHER PUBLICATIONS

Ablordeppey et al., "Design and Synthesis of Novel Analogs of Haloperidol Incapable of Forming MPP+-Like Species," Medical Chemistry Research, vol. 3, pp. 459-457, 1993.
Ablordeppey et al., "Evaluation of the eutorner of 4-(3-(4-Chlorophenyl)-3-Hydroxypyrrolidin-1-yl)-1-(4-Fluorophenyl)Butan-1-One,{(+09}, a Pyrrolidine Analog of haloperidol," Bio. & Med. Chem. Ltrs. vol. 16, pp. 3219-3223, 2006.
Ahn et al., "N-Substituted-3-arylpyrrolidines: Potent and Selective Ligands at Serotonin 1A Receptor," Bioorganic & Medicinal Chemistry Letters, pp. 1379-1384, 1999.
Gould et al., "Pyrrolididnes. IX. 3-Aryl-3-pyrrolidinols," J. Med. Chem., vol. 7, pp. 60-67, Jan. 1964.
Haglid et al., "Synthetic Analogues of Nicotine. IV," Acta Chem. Scand., vol. 17, No. 6, pp. 1743-1750, 1963. International Search Report dated Dec. 10, 2008 for corresponding International Application No. PCT/EP2008/056915.
Sonesson et al., "Regioselective Synthesis of 3-Aryl Substituted Pyrrolidines Via Palladium Catalyzed Arylation: Pharmacological Evaluation for Central Dopaminergical and Serctonergic Activity," Bioorganic & Medicinal Chemistry Letters, vol. 7, No. 3, pp. 241-246, 1997.
Sonesson et al., "Substituted (S)-Phenylpiperidines and Rigid Congeners as Preferential Dopamine Autoreceptor Antagonists: Synthesis and Structure—Activity Relationship," Journal of Medical Chemistry, vol. 37, pp. 2735-2752, 1994.

(Continued)

*Primary Examiner* — Kamal Saeed
*Assistant Examiner* — Nyeemah A Grazier
(74) *Attorney, Agent, or Firm* — Birch, Stewart, Kolasch & Birch, LLP

(57) ABSTRACT

The present invention relates to the use of compounds which increase extracellular levels of catecholamines, dopamine and norepinephrine, in cerebral cortical areas of the mammalian brain, and more specifically to the use of 3-disubstituted phenyl-1-pyrrolidinols for the treatment of central nervous system disorders.

13 Claims, 21 Drawing Sheets

OTHER PUBLICATIONS

Figure 1:
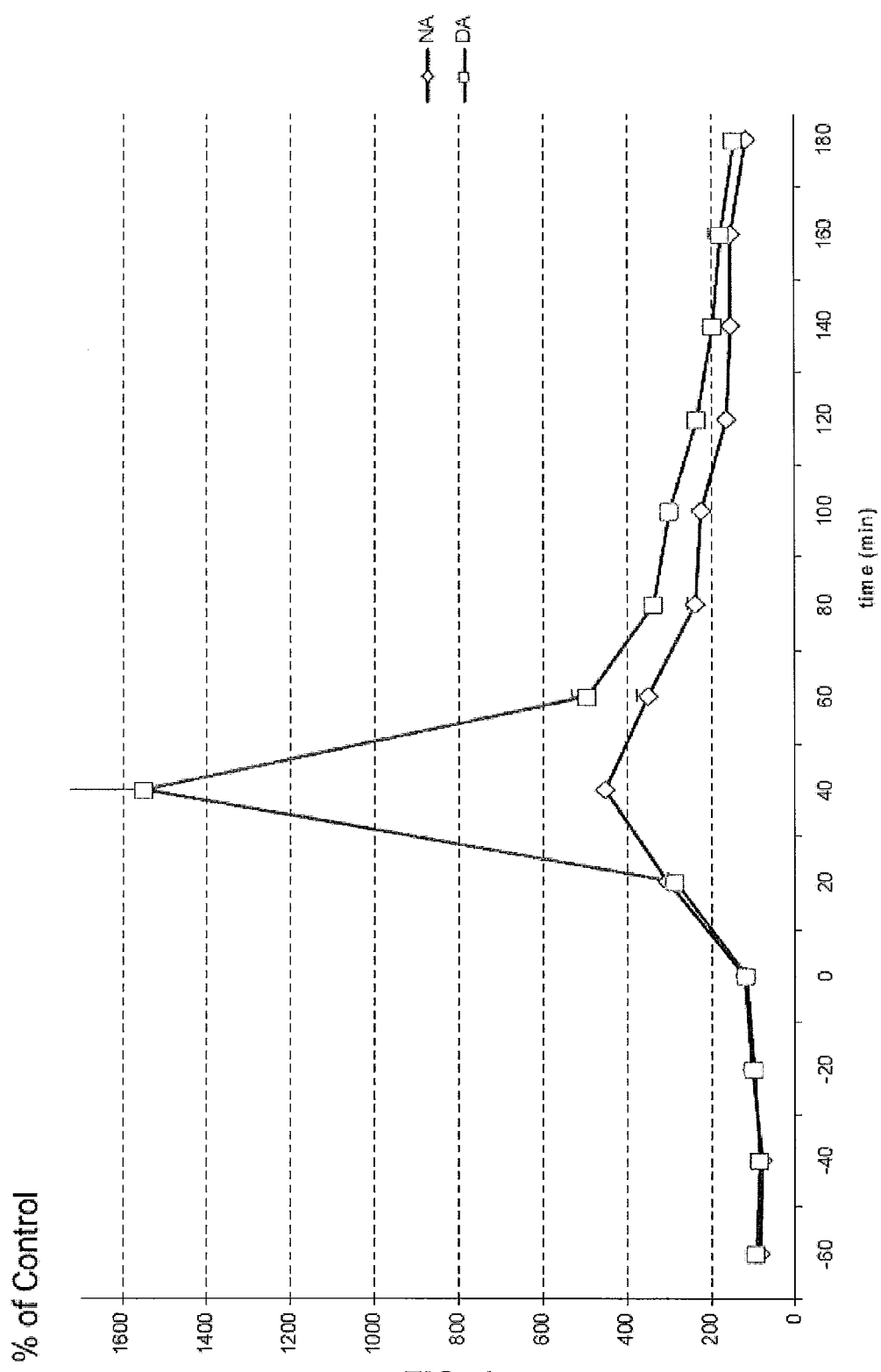

Wall et al., "Metabolism of 3-(p-Chlorophenyl) pyrrolidine, Structural Effects in Conversion of a Prototype γ-Aminobutyric Acid Prodrug to Lactam and γ-Aminobutyric Acid Type Metabolites." Journal of Medical Chemistry, vol. 32, pp. 1340-1348, 1989.

Widler et al., "Highly Potent Gerninal Bisphosphonates. From Pamidronate Disodium (Aredia) to Zoledronic Acid (Zometa)," Journal of Medical Chemistry, vol. 45, pp. 3721-3738, 2002.

Wu et al., "Pyrrolidines. VIII. 3-Acyloxy-3-Aryl-1-Ethyl-and-1-Methypyrrolidines," J. Medicinal & Pharmaceutical Chemistry. vol. 5, pp. 762-769, Jul. 1962.

European Search Report for Application No. PCT/EP2008/056912 dated Aug. 19, 2008.

Office Action issued on Dec. 21, 2011 in U.S. Appl. No. 12/663,211.

STN Accession No. 2007: 705815.

* cited by examiner

DISUBSTITUTED PHENYLPYRROLIDINES AS MODULATORS OF CORTICAL CATECHOLAMINERGIC NEUROTRANSMISSION

This application is the National Phase of PCT/EP2008/056915 filed on Jun. 4, 2008, which claims priority under 35 U.S.C. 119(e) to U.S. Provisional Application No. 60/941,994 filed on Jun. 5, 2007 and under 35 U.S.C. 119(a) to Patent Application No. 0701387-3 filed in Sweden on Jun. 5, 2007, all of which are hereby expressly incorporated by reference into the present application.

FIELD OF THE INVENTION

The present invention relates to new disubstituted phenylpyrrolidines and the use of these compounds which increase extracellular levels of catecholamines, dopamine and norepinephrine, in cerebral cortical areas of the mammalian brain, and more specifically to the use of 3-disubstituted aryl-pyrrolidinols for the treatment of central nervous system disorders.

BACKGROUND OF THE INVENTION

The cerebral cortex encompasses several major regions that are involved in higher functions such as thought, feelings, memory and planning (Principles of Neural science, 2nd Edition, Elsevier Science Publishing co., Inc. 1985, pp 671-687). Biogenic amines, i.e. dopamine, norepinephrine and serotonin, are important for mammalian cortical function. The ascending dopamine and norepinephrine pathways innervate the cortex. The serotonergic neurons of the CNS project to virtually all regions of the brain including the cerebral cortex (Fundamental Neuroscience, Academic press 1999, pp 207-212). Primary or secondary dysfunctions in the activity of these pathways lead to dysregulation of the activity at dopamine and norepinephrine and serotonin receptors in these brain areas and subsequently to manifestations of psychiatric and neurological symptoms.

The biogenic amines of the cortex modulate several aspects of cortical functions controlling affect, anxiety, motivation, cognition, attention, arousal and wakefulness (Neuropsychopharmacology, 5$^{th}$ generation of Progress, Lippincott, Williams and Wilkins 2002, Chapter 34). Thus, the catecholamines dopamine and norepinephrine exert strong influence on the prefrontal cortical areas, the integrity of which is essential for the so-called executive cognitive functions, related to e.g. attention, planning of actions and impulse control (the role of the catecholamines in these respects is reviewed in Arnsten and Li, 2005, Biol Psychiatry; 57; 1377-1384). Norepinephrine is a major part in the circuitry regulating anxiety and fear and is thus believed to be dysregulated in anxiety disorders such as panic disorders, generalized anxiety disorder (GAD) and specific phobias (Sullivan et al. 1999, Biol Psychiatry; 46:1205-121). Concerning mood and affective functions, the usefulness of compounds facilitating particularly norepinephrine and serotonin neurotransmission in the treatment of depression and anxiety has strongly contributed to the widely-accepted concept that these neurotransmitters are both involved in the regulation of affective functions (Goodman & Gilman's The Pharmacological Basis of Therapeutics, Tenth Edition, McGraw-Hill, 2001).

In general, compounds specifically affecting the transmission of biogenic amines, more precisely monoamines, norepinephrine, dopamine and serotonin are successfully used to alleviate the affective, cognitive, or attentional symptoms in patients suffering from e.g. depression, anxiety and attention deficit hyperactivity disorders (ADHD).

Furthermore, the monoamine systems in the cortex are known to be directly or indirectly involved in the core symptoms of schizophrenia. Based on a synthesis of biochemical and genetic findings along with neuropsychological observations indicating dysfunction of specific cortical areas in schizophrenia, it has been proposed that this disorder emerges as various pathological etiologies converge upon cortical function leading to dysregulation of the cortical micro-circuitry, which is clinically manifested as the symptoms of schizophrenia (Harrison and Weinberger, 2005, Molecular Psychiatry; 10:40-68). This cortical micro-circuitry is regulated by several neurotransmitters, including glutamate, GABA, and dopamine.

DESCRIPTION OF PRIOR ART

Compounds belonging to the class of substituted 3-phenylpyrrolidines have been reported previously. Among these compounds, some are inactive in the CNS, some display serotonergic or mixed serotonergic/dopaminergic pharmacological profiles while some are full or partial dopamine receptor agonists or antagonists with high affinity for dopamine receptors.

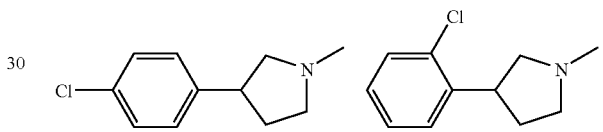

The above compounds have been disclosed as synthesis intermediates in WO 00/05225 (Preparation of biphenyl derivatives as serotonin antagonists) and by Haglid et al. as Nicotine analogs (Acta Chemica Scandinavica, 1963, 17 (6), 1743-50).

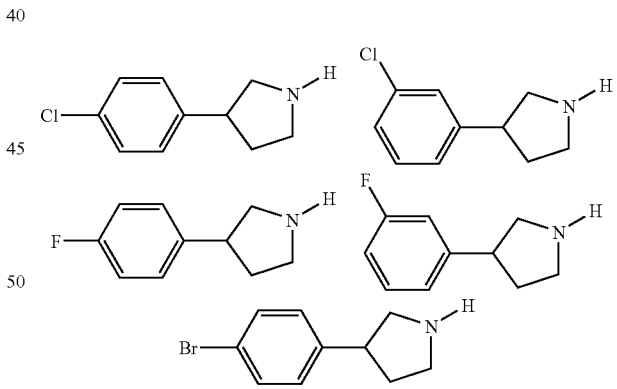

3-Chloro-phenyl-3-pyrrolidine has been disclosed as synthesis intermediate in WO 2006/117669 (Preparation of hydroxyarylcarboxamide derivatives for treating cancer) and WO 2006/112685 (Preparation of triazoles and tetrazoles containing carbamoyl group as anticonvulsants). 4-Chlorophenyl-3-pyrrolidine has been disclosed in J. Med. Chem. (2002), 45(17) 3721-3738 (Highly Potent Geminal Bisphosphonates. From Pamidronate Disodium (Aredia) to Zoledronic Acid (Zometa), Bioorganic & Medicinal Chemistry Letters (1999), 9(10), 1379-1384 (N-Substituted 3-arylpyrrolidines: potent and selective ligands at the serotonin 1A receptor), and Journal of Medicinal Chemistry (1989), 32(6) (Metabolism of 3-(p-chlorophenyl)pyrrolidine. Structural effects in conversion of a prototype γ-aminobutyric acid prodrug to lactam and γ-aminobutyric acid type metabolites). 3-Fluoro-phenyl-3-pyrrolidine has been disclosed in U.S. Pat. No. 5,128,362 and EP 325963 (Preparation of 1-(aminomethyl)-1,2,3,4-tetrahydro-naphthalenes as a 2-adrenergic antagonists). 4-Fluoro-phenyl-3-pyrrolidine has been disclosed in WO 2006/117669 (Preparation of hydroxyarylcarboxamide derivatives for treating cancer), Bioorganic & Medicinal Chemistry Letters (1999), 9(10), 1379-1384 (N-Substituted 3-arylpyrrolidines: potent and selective ligands at the serotonin 1A receptor), and U.S. Pat. No. 5,128, 362 (Preparation of 1-aminomethyl-1,2,3,4-tetrahydro-naphthalenes as adrenergic a 2 antagonists). 4-Bromo-phenyl-3-pyrrolidine has been disclosed in WO 2006/117669 (Preparation of hydroxyarylcarboxamide derivatives for treating cancer), Bioorganic & Medicinal Chemistry Letters (1999), 9(10), 1379-1384 (N-Substituted 3-arylpyrrolidines: potent and selective ligands at the serotonin 1A receptor), U.S. Pat. No. 5,128,362 (Preparation of 1-aminomethyl-1,2, 3,4-tetrahydro-naphthalenes as adrenergic a 2 antagonists), and WO 01/16136 (Preparation of tricyclic inhibitors of poly (ADP-ribose) polymerases).

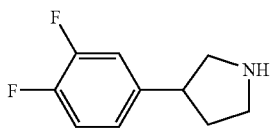

3,4-Difluoro-phenyl-3-pyrrolidine has been disclosed as a synthesis intermediate in WO 2005/028438 (Preparation of piperidine compounds as histamine H3 antagonists or inverse agonists)

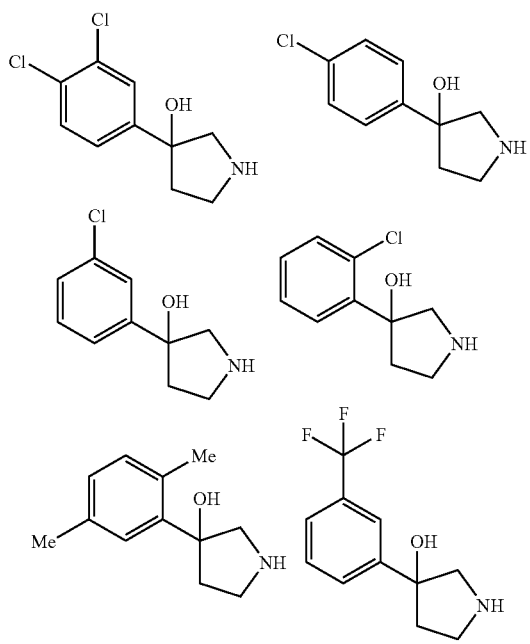

Pyrrolidinols with a secondary amine, shown above, have been disclosed by Wu et al. (3-substituted-3-pyrrolidinols, U.S. Pat. No. 3,118,907), Gould et al. (Pyrrolidines. IX. 3-Aryl-3-pyrrolidinols; J. Med. Chem. 1964, 7, 60-7), Lunsford et al. (Substituted amino alcohols, U.S. Pat. No. 2,878, 264), Hesley et al. (1-Substituted-3-phenylpyrrolidines and their pharmacological effects on the central nervous system; DE 2017255), Lunsford et al. (Tranquilizing and analgetic 1,3-disubstituted-pyrrolidines; GB 1202747), Ablordeppey et al. (Haloperidol analogs as antipsychotic agents;) WO 2007/053145 A1, Ablordeppey et al. (Evaluation of the eutomer of 4-[3-(4-chlorophenyl)-3-hydroxypyrrolidin-1-yl]-1(4-fluorophenyl)butan-1-one, ((+))-SYA 09), a pyrrolidine analog of haloperidol; Bioorg. Med. Chem. Lett. 2006, 16, 3219-3223), Ablordeppey et al. (Preparation of haloperidols as dopamine receptor antagonists; US 2006-052363), Luly et al. (Preparation of tricyclic-substituted piperidinols and analogs as chemokine receptor antagonists: US 2002-0169155 and US 2005-0070549), Kato et al. (Heterocyclic diphenylmethane derivatives as MIP-1a/RANTES receptor antagonists; WO 97/24325), Ablordeppey et al. (Design and synthesis of novel analogs of haloperidol incapable of forming MPP+ like species: Medicinal Chemistry Research 1993, 7, 459-67), and Wu et al. (Pyrrolidines. VIII. 3-Acyloxy-3-aryl-1-ethyl- and -1-methylpyrrolidines; J. Medicinal & Pharmaceutical Chemistry 1962, 5, 762-69)

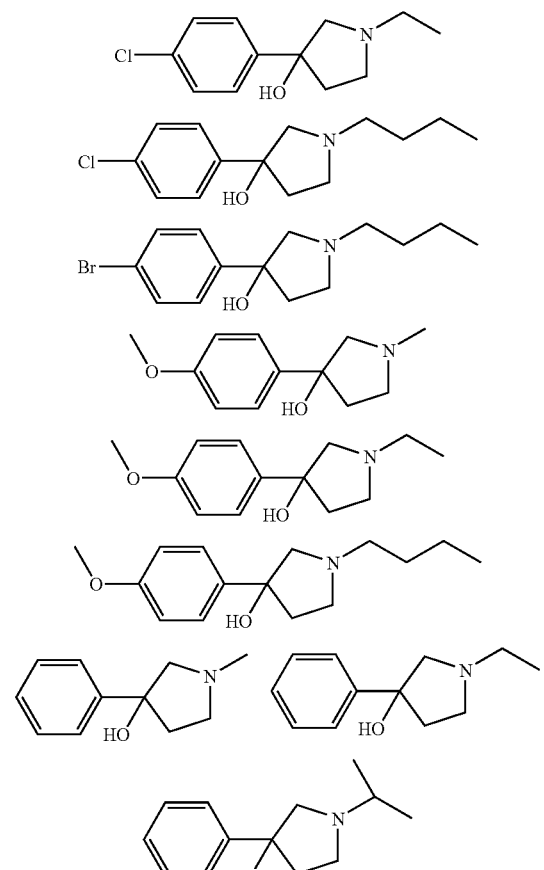

The above pyrrolidinols have been disclosed by Lunsford et al. as blockers for the sympathetic nervous system, Adrenergic blocking agents and Blood pressure effects (DE1144279B1 (1958); U.S. Pat. No. 2,878,264 (1959))

Compounds of Formula 1 (WO 92/18475) have been disclosed to possess dopaminergic stabilizer properties.

Formula 1:

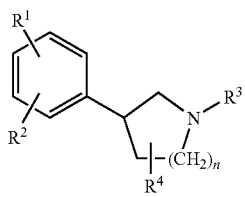

From compounds with Formula 1, Sonesson et al. (J. Med. Chem. 1994, 37, 2735-2753) have published a series of phenyl piperidines with preferential autoreceptor antagonists properties. The authors found the compounds to increase the DOPAC levels in striatum at 100 μmol/kg, which is a hallmark of dopamine D2 antagonists. Some examples from this publication are shown below.

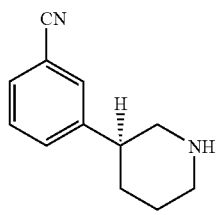

Example 26

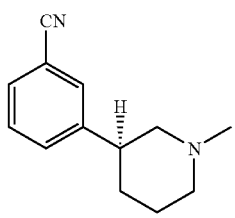

Example 27

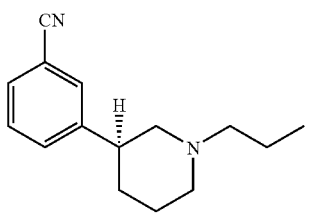

Example 10

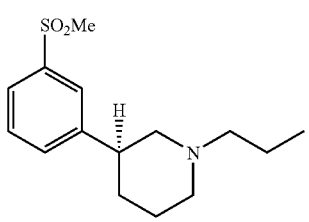

Example 16

Examples from J. Med. Chem. 1994, 37, 2735-2753

The following structures are known as synthesis intermediates in WO 01/46146.

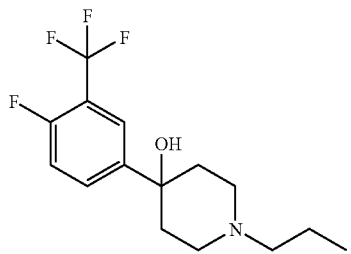

Preparation 10 in
WO01/46146

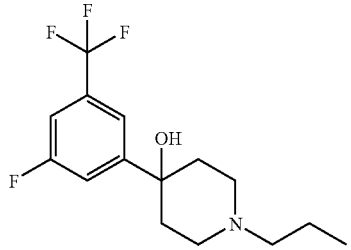

Preparation 11 in
WO01/46146

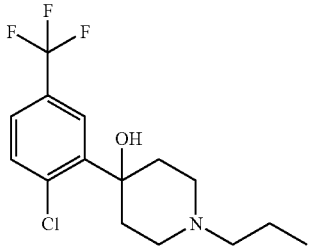

Preparation 15 in
WO01/46146

WO 2005/121092 relates to the following piperidine compounds:

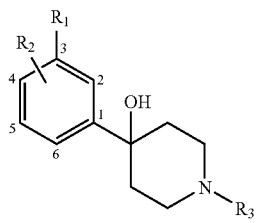

some of which are listed in Table 1, below.

In addition, Sonesson et al. (Bioorg. Med. Chem. Lett. 1997, 7, 241-246) have described that 3-phenyl-pyrrolidines substituted with electron withdrawing groups in the meta-position of the phenyl ring displays preferential dopamine autoreceptor antagonist properties. One Example from this series is presented below:

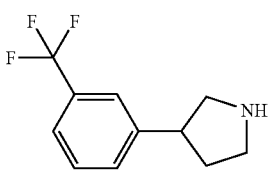

The prior art teaches that 3-phenyl-piperidines and 3-phenyl-pyrrolidines of J. Med. Chem. 1994, 37, 2735 or Bioorg. Med. Chem. Lett. 1997, 7, 241-246 have a specific, efficacious, and characteristic effect on the metabolism of dopamine, measured as increases in tissue content of DOPAC (3,4-dihydroxyphenylacetic acid) in the striatum (see Table 1). This effect on subcortical dopamine metabolism is not the objective of the present invention.

In addition, using a microdialysis technique it is shown that compounds from J. Med. Chem. 1994, 37, 2735-2753 were found to increase extracellular levels of monoamines, (dopamine, norepinephrine and serotonin), with equal effects in both striatum and in cerebral cortical areas of the mammalian brain (See FIGS. 1-10). In other words, the regionally selective properties of the compounds of the present invention between striatum and in cerebral cortical areas are not present in the prior art.

Thus, there is no guidance in WO 92/18475, WO 2005/121092, J. Med. Chem. 1994, 37, 2735 or Bioorg. Med. Chem. Lett. 1997, 7, 241-246, on how to obtain compounds that increase norepinephrine and dopamine neurotransmission with a preference for the frontal cortex.

SUMMARY OF THE INVENTION

One object of the present invention is to provide new compounds for therapeutic use, and more precisely compounds with modulation of dopamine and norepinephrine neurotransmission in the mammalian brain, including the human brain. Another object of the invention is to provide compounds with therapeutic effects after oral administration. A still further object is the provision of compounds with more optimal pharmacodynamic properties such as e.g. kinetic behaviour, bioavailability, solubility or efficacy.

The present invention concerns the unexpected discovery of the pharmacological effects of compounds of the invention on monoamines in the cerebral cortex, and the use of compounds of the invention as treatment for certain CNS disorders. By pharmacological testing in vivo in the rat it is demonstrated that compounds of the present invention produce regionally selective increases in catecholamine levels in the frontal cortex. Due to the specific modulatory effects of the catecholamines on cortical functions related to cognition, attention and affect, the compounds of the invention can be used in the treatment of disorders characterised by dysfunctions in these areas. Thus, the compounds can be used in the treatment of cognitive disorders, ADHD, depression, and anxiety. The compounds can also be used to treat schizophrenia, which is characterised by dysfunctions of the cerebral cortex manifested in cognitive failure and psychosis.

DETAILED DESCRIPTION OF THE INVENTION

The following abbreviations will be used in the present invention:
NA: norepinephrine, NM: normetanephrine; DA: dopamine, DOPAC: 3,4-dihydroxyphenylacetic acid; 3-MT: 3-methoxytyramine; 5-HT: serotonin (5-hydroxytryptamine).

The present invention relates to new 4-(disubstituted aryl)-pyrrolidinols, specifically 4-(ortho,para-disubstituted phenyl)-1-pyrrolidinols, 4-(meta,para-disubstituted phenyl)-1-pyrrolidinols, 4-(meta,meta-disubstituted phenyl)-1-pyrrolidinols and 4-(ortho,meta-disubstituted phenyl)-1-pyrrolidinols in the form of free base or pharmaceutically acceptable salts thereof, pharmaceutical compositions containing said compounds and use of said compounds in therapy.

Specifically, the invention relates to a compound of Formula (2):

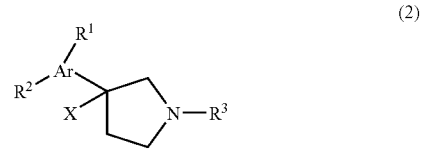

wherein;
Ar is selected from the group consisting of phenyl, thiophenyl, furanyl, 2-pyrimidinyl, oxazoyl and thiazolyl;
$R^1$ is selected from the group consisting of F and Cl;
$R^2$ is selected from the group consisting of F and Cl;
$R^3$ is selected from the group consisting of H, Me, Et, n-Pr, i-Pr, n-Bu, i-Bu, s-Bu, t-Bu, cyclopropylmethyl, $CFH_2CH_2CH_2$—, $CF_2HCH_2CH_2$—, $CF_3CH_2CH_2$—, allyl and $CH_3OCH_2CH_2$—, and
X is selected from the group consisting of F or OH; provided that when X is OH, $R^3$ is not H;
any of its stereoisomers or any mixture of its stereoisomers, or an N-oxide thereof, or a pharmaceutically acceptable salt thereof.

In a first embodiment, the invention relates to a compound of Formula (2), wherein;
Ar is selected from the group consisting of phenyl, thiophenyl, furanyl, 2-pyrimidinyl, oxazoyl and thiazolyl;
$R^1$ is selected from the group consisting of F and Cl;
$R^2$ is selected from the group consisting of F and Cl;
$R^3$ is selected from the group consisting of H, Me, Et, n-Pr, n-Bu, i-Bu, allyl and $CH_3OCH_2CH_2$—, and
X is selected from the group consisting of F or OH; provided that when X is OH, $R^3$ is not H;
any of its stereoisomers or any mixture of its stereoisomers, or an N-oxide thereof, or a pharmaceutically acceptable salt thereof.

In one embodiment, Ar is 2-thiophenyl, 2-furanyl, 2-oxazoyl or 2-thiazolyl.

Suitably, Ar is phenyl. In a further embodiment, the compound of the invention is a compound of Formula (3):

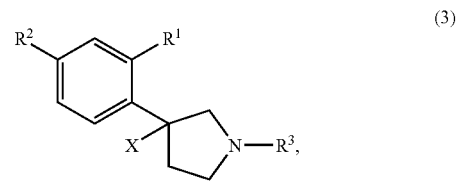

or Formula (4):

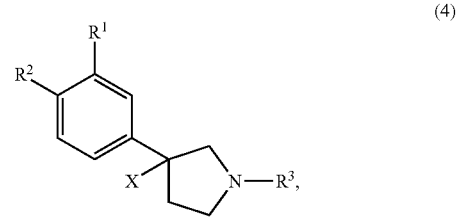

or Formula (5):

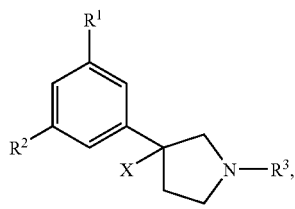

or Formula (6):

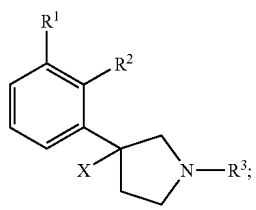

wherein $R^1$, $R^2$, $R^3$ and X are as defined above; or a pharmaceutically acceptable salt thereof.

In one embodiment, $R^1$ is F. In a further embodiment, $R^1$ is Cl. In a still further embodiment $R^2$ is F. In a further embodiment, $R^2$ is Cl. In a still further embodiment, $R^1$ is F and $R^2$ is F. In a further embodiment, $R^1$ is Cl and $R^2$ is Cl. In a still further embodiment, $R^1$ is Cl and $R^2$ is F. In a further embodiment, $R^1$ is F and $R^2$ is Cl.

In a still further embodiment, $R^3$ is be Et or n-Pr. In a further embodiment, $R^3$ is n-Pr. In a still further embodiment, $R^3$ is Et. In a further embodiment, $R^3$ is butyl, such as n-Bu or i-Bu. In a still further embodiment, $R^3$ is propyl, such as n-Pr or i-Pr. In a further embodiment, $R^3$ is H. In a still further embodiment, $R^3$ is H or Me, and $R^2$ is F. In a further embodiment, $R^3$ is Me. In a further embodiment, $R^3$ is allyl. In a further embodiment, $R^3$ is $CH_3OCH_2CH_2-$. In a still further embodiment, $R^3$ is cyclopropylmethyl. In a further embodiment, $R^3$ is $CF_3CH_2CH_2-$. One embodiment of the present invention is the pyrrolidinols, i.e. wherein X is OH. When X is OH, in one embodiment $R^3$ is n-Pr. Another embodiment of the present invention is the fluoro-pyrrolidines, i.e. wherein X is F. When X is F, in one embodiment $R^3$ is preferably Me.

Embodiments of Formula (3): In one embodiment of the compound of Formula (3), X is OH. In a further embodiment, $R^1$ is F. In a still further embodiment $R^2$ is F. In a special embodiment, $R^1$ and $R^2$ are both F. In a further embodiment, $R^3$ is Me.

Embodiments of Formula (4): In one embodiment of the compound of Formula (4), X is OH. In a further embodiment, $R^1$ is F. In a still further embodiment, $R^1$ is Cl. In a further embodiment $R^2$ is F. In a still further embodiment $R^2$ is Cl. In a special embodiment, $R^1$ and $R^2$ are both F. In a further embodiment, $R^1$ is Cl and $R^2$ is F. In a still further embodiment, $R^1$ and $R^2$ are both Cl. In a further embodiment, $R^3$ is Me. In a further embodiment, $R^3$ is Et. In a further embodiment, $R^3$ is n-Pr. In a still further embodiment, $R^3$ is i-Pr.

Embodiments of Formula (5): In one embodiment of the compound of Formula (5), X is OH. In a further embodiment, X is F. In a still further embodiment, $R^1$ is F. In a further embodiment, $R^1$ is Cl. In a still further embodiment $R^2$ is F. In a further embodiment $R^2$ is Cl. In a special embodiment, $R^1$ and $R^2$ are both F. In a further embodiment, $R^1$ is Cl and $R^2$ is F. In a still further embodiment, $R^1$ and $R^2$ are both Cl. In a further embodiment, $R^3$ is H. In a still further embodiment, $R^3$ is Me. In a further embodiment, $R^3$ is Et. In a still further embodiment, $R^3$ is n-Pr. In a further embodiment, $R^3$ is n-Bu. In a still further embodiment, $R^3$ is i-Bu. In a further embodiment, $R^3$ is allyl. In a further embodiment, $R^3$ is $CH_3OCH_2CH_2-$.

Embodiments of Formula (6): In one embodiment of the compound of Formula (6), X is OH. In a further embodiment, X is F. In a still further embodiment, $R^1$ is F. In a further embodiment, $R^1$ is Cl. In a still further embodiment $R^2$ is F. In a further embodiment $R^2$ is Cl. In a special embodiment, $R^1$ and $R^2$ are both F. In a further embodiment, $R^1$ is Cl and $R^2$ is F. In a still further embodiment, $R^1$ and $R^2$ are both Cl. In a further embodiment, $R^3$ is H. In a still further embodiment, $R^3$ is Me. In a further embodiment, $R^3$ is Et. In a still further embodiment, $R^3$ is n-Pr. In a further embodiment, $R^3$ is n-Bu. In a still further embodiment, $R^3$ is i-Bu. In a further embodiment, $R^3$ is allyl. In a further embodiment, $R^3$ is $CH_3OCH_2CH_2-$. In a still further embodiment, $R^3$ is cyclopropylmethyl. In a further embodiment, $R^3$ is $CF_3CH_2CH_2-$.

Compounds of formulae 2-6 have been found to increase the extracellular levels of norepinephrine and dopamine preferentially in the frontal cortex with no or substantially smaller effects in the striatum, as measured by the microdialysis technique. The unprecedented increase in cortical norepinephrine and dopamine of these compounds is illustrated in FIGS. 1-10.

Compounds from the invention are:
3-(3,4-difluorophenyl)-1-ethylpyrrolidin-3-ol;
3-(3,5-difluorophenyl)-1-methylpyrrolidin-3-ol;
3-(2,4-difluorophenyl)-1-methylpyrrolidin-3-ol;
3-(3,4-dichlorophenyl)-1-ethylpyrrolidin-3-ol;
3-(3,5-difluorophenyl)-1-propylpyrrolidin-3-ol;
3-(3,5-difluorophenyl)-1-ethylpyrrolidin-3-ol;
3-(3,4-difluorophenyl)-1-propylpyrrolidin-3-ol;
3-(3,5-dichlorophenyl)-1-ethylpyrrolidin-3-ol;
3-(3-chloro-5-fluorophenyl)-1-ethylpyrrolidin-3-ol;
3-(2,3-difluorophenyl)-1-ethylpyrrolidin-3-ol;
3-(3-chloro-4-fluorophenyl)-1-ethylpyrrolidin-3-ol;
3-(3,4-difluorophenyl)-1-methylpyrrolidin-3-ol;
3-(2,3-dichlorophenyl)-1-ethylpyrrolidin-3-ol;
3-(2,4-dichlorophenyl)-1-methylpyrrolidin-3-ol;
3-(2,4-dichlorophenyl)-1-isobutylpyrrolidin-3-ol;
3-(2,4-dichlorophenyl)-1-ethylpyrrolidin-3-ol;
1-allyl-3-(2,4-dichlorophenyl)pyrrolidin-3-ol;
3-(2,4-dichlorophenyl)-1-propylpyrrolidin-3-ol;
3-(2,4-dichlorophenyl)-1-(2-methoxyethyl)pyrrolidin-3-ol;
1-butyl-3-(2,4-dichlorophenyl)pyrrolidin-3-ol;
3-(2,4-difluorophenyl)-1-isobutylpyrrolidin-3-ol;
3-(2,4-difluorophenyl)-1-ethylpyrrolidin-3-ol;
1-allyl-3-(2,4-difluorophenyl)pyrrolidin-3-ol;
3-(2,4-difluorophenyl)-1-propylpyrrolidin-3-ol;
3-(2,4-difluorophenyl)-1-(2-methoxyethyl)pyrrolidin-3-ol;
1-butyl-3-(2,4-difluorophenyl)pyrrolidin-3-ol;
3-(2-chloro-4-fluorophenyl)-1-methylpyrrolidin-3-ol;
3-(2-chloro-4-fluorophenyl)-1-isobutylpyrrolidin-3-ol;
3-(2-chloro-4-fluorophenyl)-1-ethylpyrrolidin-3-ol;
1-allyl-3-(2-chloro-4-fluorophenyl)pyrrolidin-3-ol;
3-(2-chloro-4-fluorophenyl)-1-propylpyrrolidin-3-ol;
3-(2-chloro-4-fluorophenyl)-1-(2-methoxyethyl)pyrrolidin-3-ol;
1-butyl-3-(2-chloro-4-fluorophenyl)pyrrolidin-3-ol;
3-(4-chloro-2-fluorophenyl)-1-methylpyrrolidin-3-ol;
3-(4-chloro-2-fluorophenyl)-1-isobutylpyrrolidin-3-ol;
3-(4-chloro-2-fluorophenyl)-1-ethylpyrrolidin-3-ol;

1-allyl-3-(4-chloro-2-fluorophenyl)pyrrolidin-3-ol;
3-(4-chloro-2-fluorophenyl)-1-propylpyrrolidin-3-ol;
3-(4-chloro-2-fluorophenyl)-1-(2-methoxyethyl)pyrrolidin-3-ol;
1-butyl-3-(4-chloro-2-fluorophenyl)pyrrolidin-3-ol;
3-(2,3-dichlorophenyl)-1-methylpyrrolidin-3-ol;
3-(2,3-dichlorophenyl)-1-isobutylpyrrolidin-3-ol;
1-allyl-3-(2,3-dichlorophenyl)pyrrolidin-3-ol;
3-(2,3-dichlorophenyl)-1-propylpyrrolidin-3-ol;
3-(2,3-dichlorophenyl)-1-(2-methoxyethyl)pyrrolidin-3-ol;
1-butyl-3-(2,3-dichlorophenyl)pyrrolidin-3-ol;
3-(2,3-difluorophenyl)-1-methylpyrrolidin-3-ol;
3-(2,3-difluorophenyl)-1-isobutylpyrrolidin-3-ol;
3-(2,3-difluorophenyl)-1-propylpyrrolidin-3-ol;
3-(2,3-difluorophenyl)-1-(2-methoxyethyl)pyrrolidin-3-ol;
1-butyl-3-(2,3-difluorophenyl)pyrrolidin-3-ol;
3-(3-chloro-2-fluorophenyl)-1-methylpyrrolidin-3-ol;
3-(3-chloro-2-fluorophenyl)-1-isobutylpyrrolidin-3-ol;
3-(3-chloro-2-fluorophenyl)-1-ethylpyrrolidin-3-ol;
1-allyl-3-(3-chloro-2-fluorophenyl)pyrrolidin-3-ol;
3-(3-chloro-2-fluorophenyl)-1-propylpyrrolidin-3-ol;
3-(3-chloro-2-fluorophenyl)-1-(2-methoxyethyl)pyrrolidin-3-ol;
1-butyl-3-(3-chloro-2-fluorophenyl)pyrrolidin-3-ol;
3-(2-chloro-3-fluorophenyl)-1-methylpyrrolidin-3-ol;
3-(2-chloro-3-fluorophenyl)-1-isobutylpyrrolidin-3-ol;
3-(2-chloro-3-fluorophenyl)-1-ethylpyrrolidin-3-ol;
1-allyl-3-(2-chloro-3-fluorophenyl)pyrrolidin-3-ol;
3-(2-chloro-3-fluorophenyl)-1-propylpyrrolidin-3-ol;
3-(2-chloro-3-fluorophenyl)-1-(2-methoxyethyl)pyrrolidin-3-ol;
1-butyl-3-(2-chloro-3-fluorophenyl)pyrrolidin-3-ol;
1-allyl-3-(2,3-difluorophenyl)pyrrolidin-3-ol;
3-(3-chloro-4-fluorophenyl)-1-methylpyrrolidin-3-ol;
3-(3-chloro-4-fluorophenyl)-1-isobutylpyrrolidin-3-ol;
1-allyl-3-(3-chloro-4-fluorophenyl)pyrrolidin-3-ol;
3-(3-chloro-4-fluorophenyl)-1-propylpyrrolidin-3-ol;
3-(3-chloro-4-fluorophenyl)-1-(2-methoxyethyl)pyrrolidin-3-ol;
1-butyl-3-(3-chloro-4-fluorophenyl)pyrrolidin-3-ol;
3-(3,4-difluorophenyl)-1-isobutylpyrrolidin-3-ol;
1-allyl-3-(3,4-difluorophenyl)pyrrolidin-3-ol;
3-(3,4-difluorophenyl)-1-(2-methoxyethyl)pyrrolidin-3-ol;
1-butyl-3-(3,4-difluorophenyl)pyrrolidin-3-ol;
3-(4-chloro-3-fluorophenyl)-1-methylpyrrolidin-3-ol;
3-(4-chloro-3-fluorophenyl)-1-isobutylpyrrolidin-3-ol;
3-(4-chloro-3-fluorophenyl)-1-ethylpyrrolidin-3-ol;
1-allyl-3-(4-chloro-3-fluorophenyl)pyrrolidin-3-ol;
3-(4-chloro-3-fluorophenyl)-1-propylpyrrolidin-3-ol;
3-(4-chloro-3-fluorophenyl)-1-(2-methoxyethyl)pyrrolidin-3-ol;
1-butyl-3-(4-chloro-3-fluorophenyl)pyrrolidin-3-ol;
3-(3,4-dichlorophenyl)-1-methylpyrrolidin-3-ol;
3-(3,4-dichlorophenyl)-1-isobutylpyrrolidin-3-ol;
1-allyl-3-(3,4-dichlorophenyl)pyrrolidin-3-ol;
3-(3,4-dichlorophenyl)-1-propylpyrrolidin-3-ol;
3-(3,4-dichlorophenyl)-1-(2-methoxyethyl)pyrrolidin-3-ol;
1-butyl-3-(3,4-dichlorophenyl)pyrrolidin-3-ol;
3-(3,5-dichlorophenyl)-1-methylpyrrolidin-3-ol;
3-(3,5-dichlorophenyl)-1-isobutylpyrrolidin-3-ol;
1-allyl-3-(3,5-dichlorophenyl)pyrrolidin-3-ol;
3-(3,5-dichlorophenyl)-1-propylpyrrolidin-3-ol;
3-(3,5-dichlorophenyl)-1-(2-methoxyethyl)pyrrolidin-3-ol;
1-butyl-3-(3,5-dichlorophenyl)pyrrolidin-3-ol;
3-(3,5-difluorophenyl)-1-isobutylpyrrolidin-3-ol;
1-allyl-3-(3,5-difluorophenyl)pyrrolidin-3-ol;
1-butyl-3-(3,5-difluorophenyl)pyrrolidin-3-ol;
3-(3,5-difluorophenyl)-1-(2-methoxyethyl)pyrrolidin-3-ol;
3-(3-chloro-5-fluorophenyl)-1-methylpyrrolidin-3-ol;
3-(3-chloro-5-fluorophenyl)-1-isobutylpyrrolidin-3-ol;
1-allyl-3-(3-chloro-5-fluorophenyl)pyrrolidin-3-ol;
3-(3-chloro-5-fluorophenyl)-1-propylpyrrolidin-3-ol;
3-(3-chloro-5-fluorophenyl)-1-(2-methoxyethyl)pyrrolidin-3-ol; and
1-butyl-3-(3-chloro-5-fluorophenyl)pyrrolidin-3-ol.

Further compounds of the invention in which X is F are:
3-(3,5-difluorophenyl)-3-fluoropyrrolidine;
3-(3,5-difluorophenyl)-3-fluoro-1-methylpyrrolidine;
3-(3,5-dichlorophenyl)-3-fluoropyrrolidine;
3-(3-chloro-2-fluorophenyl)-3-fluoropyrrolidine;
3-(3-chloro-2-fluorophenyl)-3-fluoro-1-methylpyrrolidine;
3-(2-chloro-3-fluorophenyl)-3-fluoropyrrolidine;
3-(2-chloro-3-fluorophenyl)-3-fluoro-1-methylpyrrolidine;
3-(2,3-dichlorophenyl)-3-fluoropyrrolidine;
3-(2,3-dichlorophenyl)-3-fluoro-1-methylpyrrolidine;
3-(2,3-difluorophenyl)-3-fluoropyrrolidine;
3-(2,3-difluorophenyl)-3-fluoro-1-methylpyrrolidine;
3-(4-chloro-2-fluorophenyl)-3-fluoropyrrolidine;
3-(4-chloro-2-fluorophenyl)-3-fluoro-1-methylpyrrolidine;
3-(2-chloro-4-fluorophenyl)-3-fluoropyrrolidine;
3-(2-chloro-4-fluorophenyl)-3-fluoro-1-methylpyrrolidine;
3-(2,4-dichlorophenyl)-3-fluoropyrrolidine;
3-(2,4-dichlorophenyl)-3-fluoro-1-methylpyrrolidine;
3-(2,4-difluorophenyl)-3-fluoropyrrolidine;
3-(2,4-difluorophenyl)-3-fluoro-1-methylpyrrolidine;
3-(4-chloro-3-fluorophenyl)-3-fluoropyrrolidine;
3-(4-chloro-3-fluorophenyl)-3-fluoro-1-methylpyrrolidine;
3-(3-chloro-4-fluorophenyl)-3-fluoropyrrolidine;
3-(3-chloro-4-fluorophenyl)-3-fluoro-1-methylpyrrolidine;
3-(3,4-dichlorophenyl)-3-fluoropyrrolidine;
3-(3,4-dichlorophenyl)-3-fluoro-1-methylpyrrolidine;
3-(3,4-difluorophenyl)-3-fluoropyrrolidine;
3-(3,4-difluorophenyl)-3-fluoro-1-methylpyrrolidine;
3-(3-chloro-5-fluorophenyl)-3-fluoropyrrolidine;
3-(3-chloro-5-fluorophenyl)-3-fluoro-1-methylpyrrolidine; and
3-(3,5-dichlorophenyl)-3-fluoro-1-methylpyrrolidine.

In a special embodiment the compound of the invention is
(−)-3-(3,5-DIFLUOROPHENYL)-1-ETHYLPYRROLIDIN-3-OL;
(+)-3-(3,5-DIFLUOROPHENYL)-1-ETHYLPYRROLIDIN-3-OL;
3-(3-CHLORO-4-FLUOROPHENYL)-1-ETHYLPYRROLIDIN-3-OL;
3-(2,3-DIFLUOROPHENYL)-1-ETHYLPYRROLIDIN-3-OL;
3-(3-CHLORO-5-FLUOROPHENYL)-1-ETHYLPYRROLIDIN-3-OL;
3-(3,5-DICHLOROPHENYL)-1-ETHYLPYRROLIDIN-3-OL;
3-(3,4-DIFLUOROPHENYL)-1-PROPYLPYRROLIDIN-3-OL;
3-(3,5-DIFLUOROPHENYL)-1-ETHYLPYRROLIDIN-3-OL;
3-(3,5-DIFLUOROPHENYL)-1-PROPYLPYRROLIDIN-3-OL;
3-(3,4-DICHLOROPHENYL)-1-ETHYLPYRROLIDIN-3-OL;
3-(3,5-DIFLUOROPHENYL)-3-FLUORO-1-METHYLPYRROLIDINE;
3-(3,4-DIFLUOROPHENYL)-1-ETHYLPYRROLIDIN-3-OL;
3-(3,5-DIFLUOROPHENYL)-3-FLUOROPYRROLIDINE;

3-(3,5-DICHLOROPHENYL)-3-FLUOROPYRROLIDINE;
3-(2,4-DIFLUOROPHENYL)-1-METHYLPYRROLIDIN-3-OL;
3-(3,4-DIFLUOROPHENYL)-1-METHYLPYRROLIDIN-3-OL;
3-(2,3-DICHLOROPHENYL)-1-ETHYLPYRROLIDIN-3-OL;
3-(3,5-DIFLUOROPHENYL)-1-METHYLPYRROLIDIN-3-OL;
3-(3-CHLORO-2-FLUOROPHENYL)-1-METHYLPYRROLIDIN-3-OL;
3-(3-CHLORO-2-FLUOROPHENYL)-1-ETHYLPYRROLIDIN-3-OL;
3-(3-CHLORO-4-FLUOROPHENYL)-1-PROPYLPYRROLIDIN-3-OL;
3-(3-CHLORO-5-FLUOROPHENYL)-1-PROPYLPYRROLIDIN-3-OL;
3-(2,3-DIFLUOROPHENYL)-3-FLUOROPYRROLIDINE;
(+)-3-(3,4-DIFLUOROPHENYL)-1-ETHYLPYRROLIDIN-3-OL;
(−)-3-(3,4-DIFLUOROPHENYL)-1-ETHYLPYRROLIDIN-3-OL;
3-(3-CHLORO-5-FLUOROPHENYL)-1-METHYLPYRROLIDIN-3-OL;
(+)-3-(3,4-DIFLUOROPHENYL)-1-PROPYLPYRROLIDIN-3-OL;
(−)-3-(3,4-DIFLUOROPHENYL)-1-PROPYLPYRROLIDIN-3-OL;
(+)-3-(3,5-DIFLUOROPHENYL)-1-PROPYLPYRROLIDIN-3-OL;
(−)-3-(3,5-DIFLUOROPHENYL)-1-PROPYLPYRROLIDIN-3-OL;
(−)-3-(3-CHLORO-5-FLUOROPHENYL)-1-ETHYLPYRROLIDIN-3-OL;
(−)-3-(2,3-DIFLUOROPHENYL)-1-ETHYLPYRROLIDIN-3-OL;
(−)-3-(2,3-DIFLUOROPHENYL)-1-PROPYLPYRROLIDIN-3-OL;
(+)-3-(2,3-DIFLUOROPHENYL)-1-PROPYLPYRROLIDIN-3-OL;
(+)-3-(3-CHLORO-2-FLUOROPHENYL)-1-ETHYLPYRROLIDIN-3-OL;
(+)-3-(2,3-DIFLUOROPHENYL)-1-ETHYLPYRROLIDIN-3-OL;
(−)-3-(3-CHLORO-2-FLUOROPHENYL)-1-ETHYLPYRROLIDIN-3-OL;
(−)-1-BUTYL-3-(2,3-DIFLUOROPHENYL)PYRROLIDIN-3-OL;
(−)-3-(2,3-DIFLUOROPHENYL)-1-ISOBUTYLPYRROLIDIN-3-OL;
(−)-3-(2,3-DIFLUOROPHENYL)-1-METHYLPYRROLIDIN-3-OL;
(−)-1-ALLYL-3-(2,3-DIFLUOROPHENYL)PYRROLIDIN-3-OL;
(−)-3-(2,3-DIFLUOROPHENYL)-1-(2-METHOXYETHYL)PYRROLIDIN-3-OL;
(−)-1-BUTYL-3-(3,5-DIFLUOROPHENYL)PYRROLIDIN-3-OL;
(−)-1-ALLYL-3-(3,5-DIFLUOROPHENYL)PYRROLIDIN-3-OL;
(−)-3-(3,5-DIFLUOROPHENYL)-1-(2-METHOXYETHYL)PYRROLIDIN-3-OL;
(−)-3-(3,5-DIFLUOROPHENYL)-1-ISOBUTYLPYRROLIDIN-3-OL;
(−)-3-(3,5-DIFLUOROPHENYL)-1-METHYLPYRROLIDIN-3-OL;
(−)-3-(2,3-DIFLUOROPHENYL)-1-(3,3,3-TRIFLUOROPROPYL)PYRROLIDIN-3-OL;
(−)-1-(CYCLOPROPYLMETHYL)-3-(2,3-DIFLUOROPHENYL)PYRROLIDIN-3-OL;
3-(3,4-DIFLUOROPHENYL)-1-ISOPROPYLPYRROLIDIN-3-OL;
(+)-1-BUTYL-3-(3,5-DIFLUOROPHENYL)PYRROLIDIN-3-OL;
(+)-3-(3,5-DIFLUOROPHENYL)-1-METHYLPYRROLIDIN-3-OL;
(+)-3-(3,5-DIFLUOROPHENYL)-1-ISOBUTYLPYRROLIDIN-3-OL;
(+)-3-(3,5-DIFLUOROPHENYL)-1-(2-METHOXYETHYL)PYRROLIDIN-3-OL;
(+)-1-ALLYL-3-(3,5-DIFLUOROPHENYL)PYRROLIDIN-3-OL;
(+)-3-(3-CHLORO-2-FLUOROPHENYL)-1-METHYLPYRROLIDIN-3-OL;
(−)-3-(3-CHLORO-2-FLUOROPHENYL)-1-METHYLPYRROLIDIN-3-OL;
(+)-1-BUTYL-3-(2,3-DIFLUOROPHENYL)PYRROLIDIN-3-OL;
(+)-3-(2,3-DIFLUOROPHENYL)-1-METHYLPYRROLIDIN-3-OL;
(+)-3-(2,3-DIFLUOROPHENYL)-1-(2-METHOXYETHYL)PYRROLIDIN-3-OL;
(+)-3-(2,3-DIFLUOROPHENYL)-1-ISOBUTYLPYRROLIDIN-3-OL;
(+)-1-ALLYL-3-(2,3-DIFLUOROPHENYL)PYRROLIDIN-3-OL;
(+)-3-(2,3-DIFLUOROPHENYL)-1-(3,3,3-TRIFLUOROPROPYL)PYRROLIDIN-3-OL;
(+)-1-(CYCLOPROPYLMETHYL)-3-(2,3-DIFLUOROPHENYL)PYRROLIDIN-3-OL;
(−)-3-(3-CHLORO-5-FLUOROPHENYL)-1-METHYLPYRROLIDIN-3-OL;
(+)-3-(3-CHLORO-5-FLUOROPHENYL)-1-METHYLPYRROLIDIN-3-OL;
(+)-3-(3-CHLORO-5-FLUOROPHENYL)-1-ETHYLPYRROLIDIN-3-OL;
or a pharmaceutically acceptable salt thereof.

Any combination of two or more of the embodiments as described above is considered within the scope of the present invention.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methane-sulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

Specific examples of prodrugs of the compounds of the present invention are the N-oxides mentions below and the following N-hydroxy-derivatives:
3-(3-chloro-2-fluorophenyl)-3-fluoropyrrolidin-1-ol;
3-(2-chloro-3-fluorophenyl)-3-fluoropyrrolidin-1-ol;
3-(2,3-dichlorophenyl)-3-fluoropyrrolidin-1-ol;
3-(2,3-difluorophenyl)-3-fluoropyrrolidin-1-ol;
3-(4-chloro-2-fluorophenyl)-3-fluoropyrrolidin-1-ol;
3-(2-chloro-4-fluorophenyl)-3-fluoropyrrolidin-1-ol;
3-(2,4-dichlorophenyl)-3-fluoropyrrolidin-1-ol;
3-(2,4-difluorophenyl)-3-fluoropyrrolidin-1-ol;
3-(4-chloro-3-fluorophenyl)-3-fluoropyrrolidin-1-ol;
3-(3-chloro-4-fluorophenyl)-3-fluoropyrrolidin-1-ol;
3-(3,4-dichlorophenyl)-3-fluoropyrrolidin-1-ol;
3-(3,4-difluorophenyl)-3-fluoropyrrolidin-1-ol;
3-(3-chloro-5-fluorophenyl)-3-fluoropyrrolidin-1-ol;
3-(3,5-dichlorophenyl)-3-fluoropyrrolidin-1-ol;
3-(3,5-difluorophenyl)-3-fluoropyrrolidin-1-ol.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms.

The invention includes all such isomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphor-sulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

N-Oxides

In the context of this invention an N-oxide designates an oxide derivative of a tertiary amine, including a nitrogen atom of an aromatic N-heterocyclic compound, a non-aromatic N-heterocyclic compounds, a trialkylamine and a trialkenylamine. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

The following N-oxides act as prodrugs to the compounds of the invention; Formula (7):

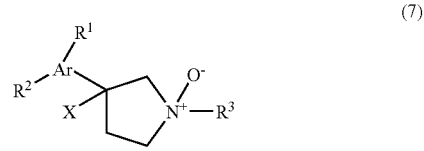

(7)

wherein:
Ar is selected from the group consisting of phenyl, thiophenyl, furanyl, 2-pyrimidinyl, oxazoyl and thiazolyl;
$R^1$ is selected from the group consisting of F and Cl;
$R^2$ is selected from the group consisting of F and Cl;
$R^3$ is selected from the group consisting of H, Me, Et, n-Pr, n-Bu, i-Bu, allyl and $CH_3OCH_2CH_2$—,
X is selected from the group consisting of F or OH; provided that when X is OH, $R^3$ is not H;
and the pharmaceutically acceptable salts.

Of particular interest are prodrugs having Formula (8):

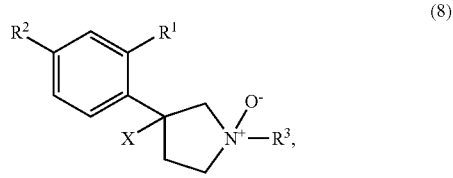

(8)

or Formula (9):

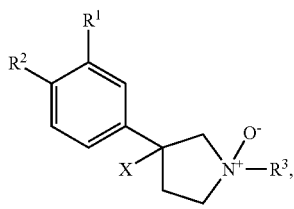

or Formula (10):

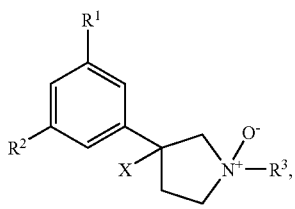

or Formula (11):

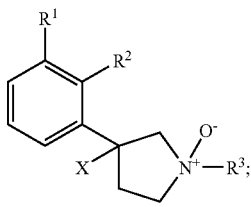

wherein $R^1$, $R^2$, $R^3$ and X are as defined above, and the pharmaceutically acceptable salts thereof. Suitably, $R^1$ is F. $R^3$ may be Et or n-Pr, and is preferably n-Pr. When $R^3$ is H or Me, $R^2$ may be F. In one embodiment, $R^3$ is Me. Another embodiment of the present invention is the pyrrolidinols, i.e. wherein X is OH.

N-oxides according to the invention include:
3-(3-chloro-2-fluorophenyl)-3-fluoro-1-methylpyrrolidine 1-oxide;
3-(2,3-dichlorophenyl)-3-fluoro-1-methylpyrrolidine 1-oxide;
3-(2-chloro-3-fluorophenyl)-3-fluoro-1-methylpyrrolidine 1-oxide;
3-(2,3-difluorophenyl)-3-fluoro-1-methylpyrrolidine 1-oxide;
3-(2,4-dichlorophenyl)-3-fluoro-1-methylpyrrolidine 1-oxide;
3-(4-chloro-2-fluorophenyl)-3-fluoro-1-methylpyrrolidine 1-oxide;
3-(2-chloro-4-fluorophenyl)-3-fluoro-1-methylpyrrolidine 1-oxide;
3-(2,4-difluorophenyl)-3-fluoro-1-methylpyrrolidine 1-oxide;
3-(4-chloro-3-fluorophenyl)-3-fluoro-1-methylpyrrolidine 1-oxide;
3-(3,4-difluorophenyl)-3-fluoro-1-methylpyrrolidine 1-oxide;
3-(3,4-dichlorophenyl)-3-fluoro-1-methylpyrrolidine 1-oxide;
3-(3-chloro-4-fluorophenyl)-3-fluoro-1-methylpyrrolidine 1-oxide;
3-(3-chloro-5-fluorophenyl)-3-fluoro-1-methylpyrrolidine 1-oxide;
3-(3,5-dichlorophenyl)-3-fluoro-1-methylpyrrolidine 1-oxide;
3-(3,5-difluorophenyl)-3-fluoro-1-methylpyrrolidine 1-oxide;
3-(3-chloro-5-fluorophenyl)-1-ethylpyrrolidin-3-ol 1-oxide; and
3-(2,3-difluorophenyl)-1-propylpyrrolidin-3-ol 1-oxide.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Biological Activity

The compounds according to the present invention possess norepinephrine, dopamine and to some extent serotonin-modulating properties and both they and their pharmaceutical compositions are useful in treating numerous central nervous system disorders including psychiatric disorders. Particularly, the compounds and their pharmaceutical compositions are used in the treatment of CNS disorders where the cortical monoaminergic systems are dysfunctional due to direct or indirect causes.

The compounds and compositions according to the invention can be used to treat cognitive disorders including neurodegenerative (e.g. dementia and age-related cognitive impairment) and developmental disorders, such as Autism spectrum disorders, ADHD, Cerebral Palsy, Gilles de la Tourette's syndrome, as well as cognitive disorders occurring as part of the core symptoms of schizophrenia.

The compounds and compositions according to the invention can be used to treat affective disorders including depression and bipolar disorder. They can also be used to treat schizophrenia and schizophreniform disorders.

The compounds and compositions according to the invention can be used to treat anxiety disorders including generalized anxiety disorder (GAD), specific phobias and panic disorder (PD). They are also useful for treatment of sleep disorders.

The compounds according to the present invention have been shown to increase the extra-cellular levels of dopamine and norepinephrine in the cerebral cortex and in some cases also serotonin.

However, compounds of the present invention do not have the effects on the metabolism of dopamine in the striatum that is characteristic for the pharmacological actions of the compounds described in the prior art. Thus the compounds of the present invention have a surprising and distinct pharmacology (see Table 1).

TABLE 1

The increase in DOPAC levels (3,4-dihydroxyphenylacetic acid) in the rat striatum after systemic adminstration of test compound (100 μmol/kg s.c.). Expressed as the %-increase from control value. For method see the enclosed description.

| | DOPAC %-increase |
|---|---|
| Comparative Examples[1] | |
| Example 10 of ref. 1 | +262[2] |
| Example 16 of ref. 1 | +150[2] |
| Example 26 of ref. 1 | +67[2] |
| Example 27 of ref. 1 | +74[2] |
| Example 9d of ref. 2 | +63[3] |
| Example 11d of ref. 2 | +197[3] |
| Example 1 of WO2005/121092 | +217 |
| Example 3 of WO2005/121092 | +144 |
| Example 4 of WO2005/121092 | +107 |
| Example 5 of WO2005/121092 | +185 |
| Example 8 of WO2005/121092 | +121 |
| Example 2 of WO2005/121092 | +169 |
| Examples | |
| Example 1 | 0 |
| Example 2 | −16 |
| Example 3 | −28 |
| Example 4 | −10 |
| Example 5 | −26 |
| Example 6 | −10 |
| Example 7 | 0 |
| Example 8 | −24 |
| Example 9 | −5 |
| Example 10 | −26 |
| Example 11 | −4 |
| Example 12 | −19 |
| Example 32 | +8 |
| Example 36 | −15 |

[1]Comparative Examples from prior art; Ref 1: J. Med. Chem. 1994, 37, 2735; Ref 2: Bioorg. Med. Chem. Lett. 1997, 7, 241-246. Ref. 3; WO 2005/121092.
[2]Data taken from Table 2 in Ref 1.
[3]Data taken from Table 2 in Ref 2.
The data from this reference is DOPA accumulation and not DOPAC. DOPAC and DOPA are both a measure of the indirect change in concentration of dopamine in the brain of the experimental animals.
An increase in DOPAC and DOPA levels show an increased synthesis and turnover of dopamine in the system. DOPA accumulation measures the increase in the concentration of 3,4-dihydroxyphenylalanine in the striatal regions of the brain.
DOPAC measures the increase in the concentration of 3,4-dihydroxy phenylacetic acid in the striatal regions of the brain. There is a strong relation between DOPA and DOPAC It can be seen that—upon administration—those of the tested compounds described in WO 2005/121092, J. Med. Chem. 1994, 37, 2735 and Bioorg. Med. Chem. Lett. 1997 produce a significant increase in striatum DOPAC levels. In contrast, compounds of the present invention have surprisingly shown to provide a weak effect in striatum DOPAC levels. On the other hand, the essential characteristic of compounds of the present invention is to produce increased cortical levels of catecholamines, measured as the extracellular levels of dopamine and norepinephrine assessed by the microdialysis technique, while displaying no or at most weak effects on subcortical catecholamines (FIGS. 1-10).

Description of Animal Models Used in the Invention

The measurement of the tissue content of DOPAC is well established in the field of research since the 1960's. In short, male Sprague-Dawely rats are administered the test compound 60 minutes prior to decapitation. The brain is rapidly taken out and dissected. The striatum is rapidly frozen and subsequently quantitatively analysed with respect to its content of DOPAC by means of HPLC and electrochemical detection. The number of animals used for each test compound/vehicle is 4/group.

The microdialysis technique (Ungerstedt, Herrera-Marschitz et al. 1982) is a well established technique for measuring extracellular levels of neurotransmitters (Ungerstedt 1991). The microdialysis technique was used to measure the effect of drugs upon the monoamine transmitters. The appended graphs (FIGS. 20 and 21) show the effects of one established antidepressant (mirtazapine) upon monoamines in the striatum and frontal cortex, as well as for compounds claimed in the present invention (FIGS. 1-10). The number of animals (n) used for each compound tested is noted in the figure legend.

Effects on Dopamine and Norepinephrine in Cortical Regions

Cognition

The cortical circuitry underlying cognitive functions including memory, attention and working memory comprises a network of glutamatergic and GABAergic neurons, innervated by ascending dopaminergic and norepinephrinergic projections (Harrison and Weinberger 2005, Arnsten and Li 2005). Dopamine, acting through DA D1 receptors, enhances cognitive functions, while hypofunction of the cortical DA transmission produces specific cognitive deficits (reviewed in Goldman-Rakic, 2004). Likewise, norepinephrine has been found to enhance cognitive functions, presumably depending on stimulation of post-synaptic alpha-2 receptors in the prefrontal cortex (Arnsten, 2004). Clinical examples of the effects of cortical DA and NE deficiency are the cognitive disorders seen in schizophrenia and ADHD. In schizophrenia, cortical DA deficiency is regarded as a key feature underlying cognitive dysfunctions (Perlman et al., 2004, Goldman-Rakic, 2004). One mechanism by which such cortical DA hypofunction is believed to arise is a well described point mutation in the COMT encoding gene, leading to exaggerated activity of COMT, and therefore, an increased rate of elimination of DA, and ensuing, decreased levels of DA particularly in the cortex (Harrison and Weinberger 2005, Perlman et al., 2004). This mutation of COMT is genetically linked to schizophrenia as well as correlated to cognitive performance in healthy individuals. Apart from COMT anomalies, a variety of other pathogenetic pathways are proposed to lead to a functionally similar state of cortical dysfunction in schizophrenia, manifested by the characteristic abnormalities of cognitive functions seen in schizophrenic patients (Harrison and Weinberger, 2005). For instance, a number of susceptibility genes are thought to preferentially affect NMDA receptor mediated glutamate transmission. Due to the beneficial effects on cognitive functions by augmented DA D1 receptor stimulation, strengthening of cortical DA transmission can normalise cortical activity and enhance cognitive functions in schizophrenia as well as in other conditions (Goldman-Rakic, 2004). Furthermore, since the abnormalities in the cortical microcircuitry are regarded as the core feature underlying the clinical syndrome, restoration of this microcircuitry by facilitating DA transmission should not only improve cognitive functions in schizophrenia, but also reduce psychotic symptoms. Thus, normalisation of cortical DA transmission would as a secondary effect lead to normalisation of subcortical DA transmission, and thus, alleviation of the symptoms related to subcortical hyperdopaminergia (Goldman-Rakic, 2004, Perlman et al., 2004). Furthermore, a common feature of atypical antipsychotics, hypothesised to underlie their superior efficacy and fewer side effects compared to other antipsychotic compounds, is their ability to increase cortical dopamine (Moghaddam and Bunney, 1990, Deutch et al., 1991). It is important to note that the principle described in this invention to achieve cognitive enhancement and antipsychotic effects is dependent on regionally selective cortical increase in DA and NE, while increases in subcortical, eg striatal, DA are not sought for. In conclusion, compounds according to this invention that increase cortical DA, but not subcortical DA transmission, will improve cognitive functions and reduce psychotic symptoms in schizophrenia.

The other clinical example showing the role of DA and NE in cognitive functions is the clinical features of ADHD, including the mode of action of compounds used to relieve the symptoms in this disorder. The key features of ADHD are deficiencies in attention, lack of ability to focus on a task for a prolonged time, impulsivity, and hyperactivity (Biederman 2005, Arnsten and Li 2005). In neuropsychological tests, ADHD patients perform poorly on tests specifically assessing prefrontal cortical functions (Arnsten and Li, 2005). The structure of the cortical circuitry underlying these functions suggests that insufficient DA and NE transmission would lead to the specific neuropsychological deficits seen in ADHD. Studies on the etiology of ADHD all point toward disregulation of DA and NE, particularly in cortical regions. The pharmacological treatments available are mainly psycho-stimulants, including dex-amphetamine, and methylphenidate, which increase DA and NE in most brain areas. A recent advancement in the treatment of ADHD is the compound atomoxetine (U.S. Pat. No. 5,658,590), which produces regionally selective increases in cortical DA and NE, relieving core symptoms while avoiding side effects related to increase subcortical in DA transmission, thus supporting that cortical, rather than subcortical effects on catecholamines are essential to the clinical efficacy of ADHD medications (Pliszka, 2005).

Taken together, there is solid evidence that enhanced cortical DA and NE transmission would improve the symptoms of ADHD, including cognitive improvement. Furthermore, the role of cortical DA and NE in cognitive functions implies that enhancement of cortical DA transmission also improves cognitive functioning in cognitive disorders arising from causes other than schizophrenia or ADHD, as well as in healthy individuals. This is supported by the correlation between COMT activity and cognitive performance in healthy individuals (Perlman et al., 2004) and by numerous studies in rodents, primates and humans concerning the influence of cortical DA and NE on cognitive functions in healthy states as well as in different disorders (Arnsten, 2004, Goldman-Rakic, 2004). Consequently, the compounds according to the present invention will be useful to treat the symptoms of ADHD, as well as cognitive disorders in general, due to their ability to produce regionally selective increases in cortical DA and NE.

Anxiolytic and Antidepressant Actions

A common trait for all clinically effective classes of antidepressants is an elevation of the levels of dopamine and norepinephrine in the cortex (Tanda, Carboni et al. 1994; Millan, Lejeune et al. 2000). As an example, the clinically effective antidepressant mirtazapine (remeron) has been shown to increase predominantly extracellullar norepinephrine and dopamine in the cortex (See FIG. 21, and Devoto, Flore et al. 2004). As compounds claimed in the present invention elevate the levels of dopamine and norepinephrine in the cortex this supports our claim that they function as antidepressants (see FIGS. 1-10). Furthermore, norepinephrine is strongly involved in the neuronal pathways, comprising the locus ceruleus, the amygdala, and the cerebral cortex, controlling fear and anxiety and so, modulation of cortical norepinephrine transmission modulates states of anxiety (Sullivan et al. 1999, Biol Psychiatry; 46:1205-121). Accordingly, compounds that alter cortical norepinephrinergic transmission are reported to be effective in the treatment of anxiety disorders. More specifically, NE modulating compounds like mirtazapine (Remeron), which produces marked increases in cortical NE levels by a mechanism other than NE reuptake inhibition (FIG. 21), and venlafaxine, which increases cortical NE by inhibition of norepinephrine re-uptake, both have anxiolytical properties in clinical studies (Neuropsychopharmacology, $5^{th}$ generation of Progress, Lippincott, Williams and Wilkins 2002, pp 967-980). Based on this evidence for the beneficial effects of enhanced cortical norepinephrine transmission on anxiety disorders, along with the neurobiological back-ground demonstrating the crucial role of norepinephrine in the control of anxiety, it is concluded that the compounds of the present invention, which produces marked increases in cortical NE will be effective in the treatment of anxiety disorders.

EXAMPLES ACCORDING TO THE INVENTION

FIGS. 1-10

FIG. 1. Example 1, 50 µmol/kg s.c. p.f. cortex amines

Figure 2:
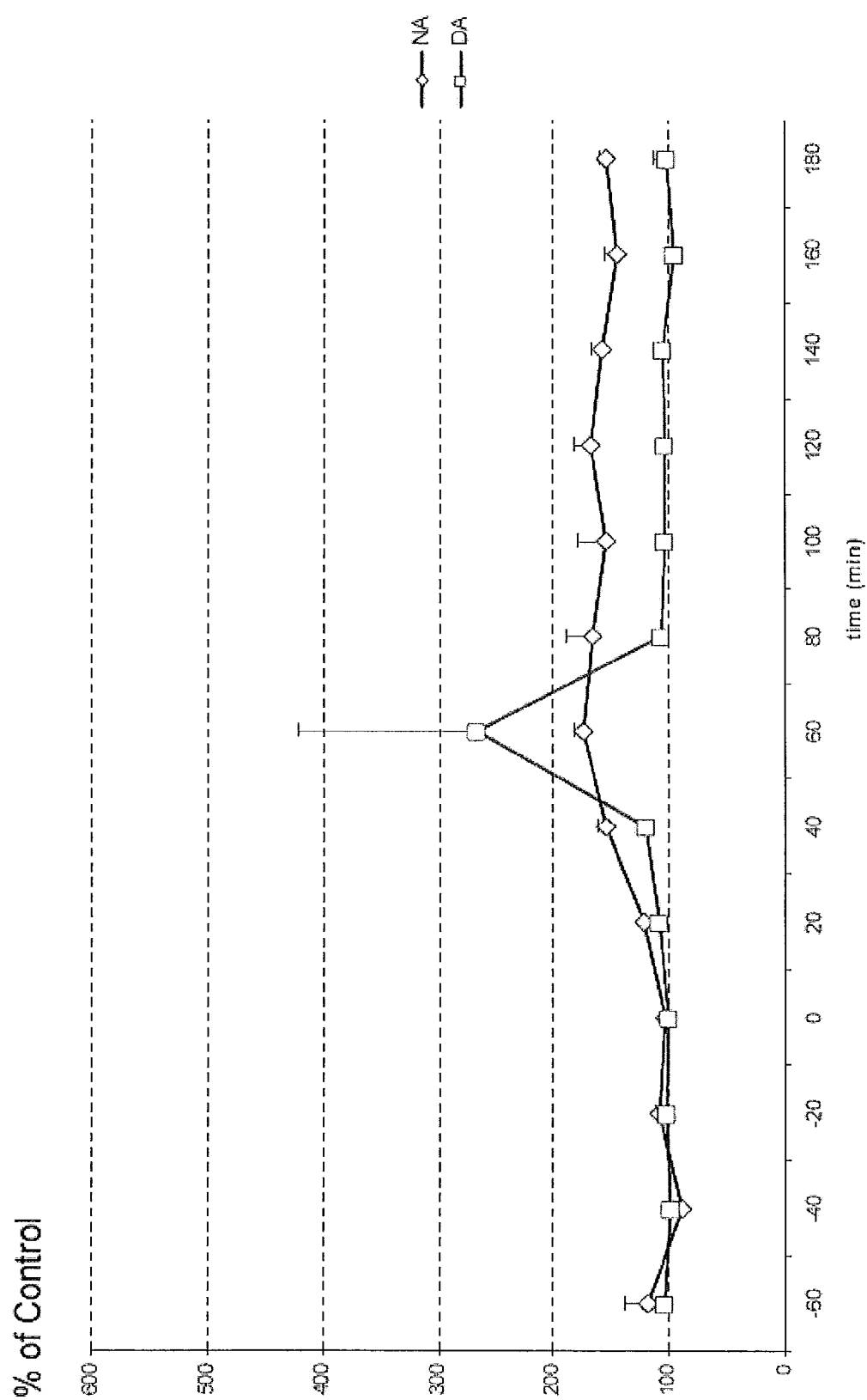
Figure 3:
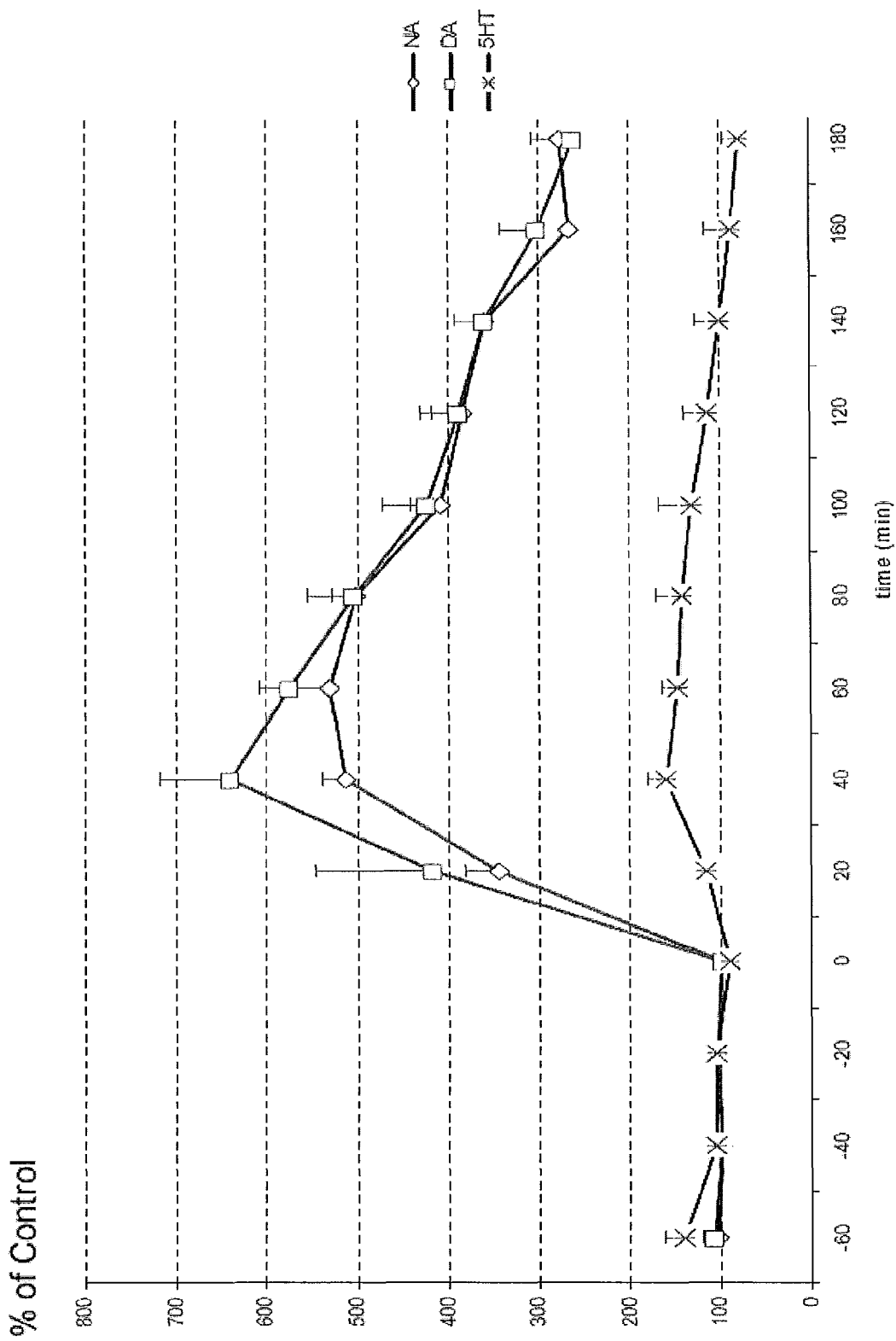
Figure 4:
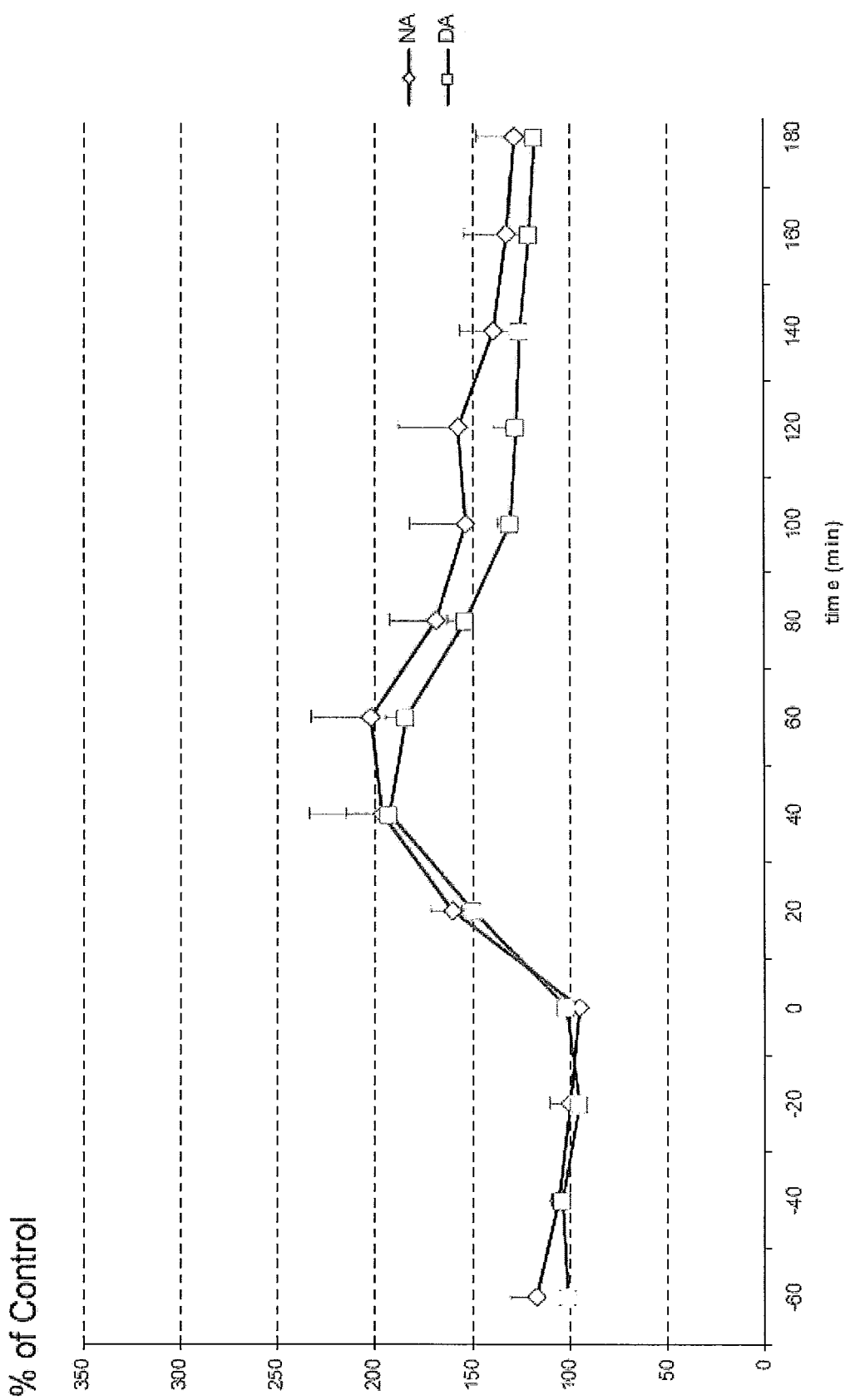
Figure 5:
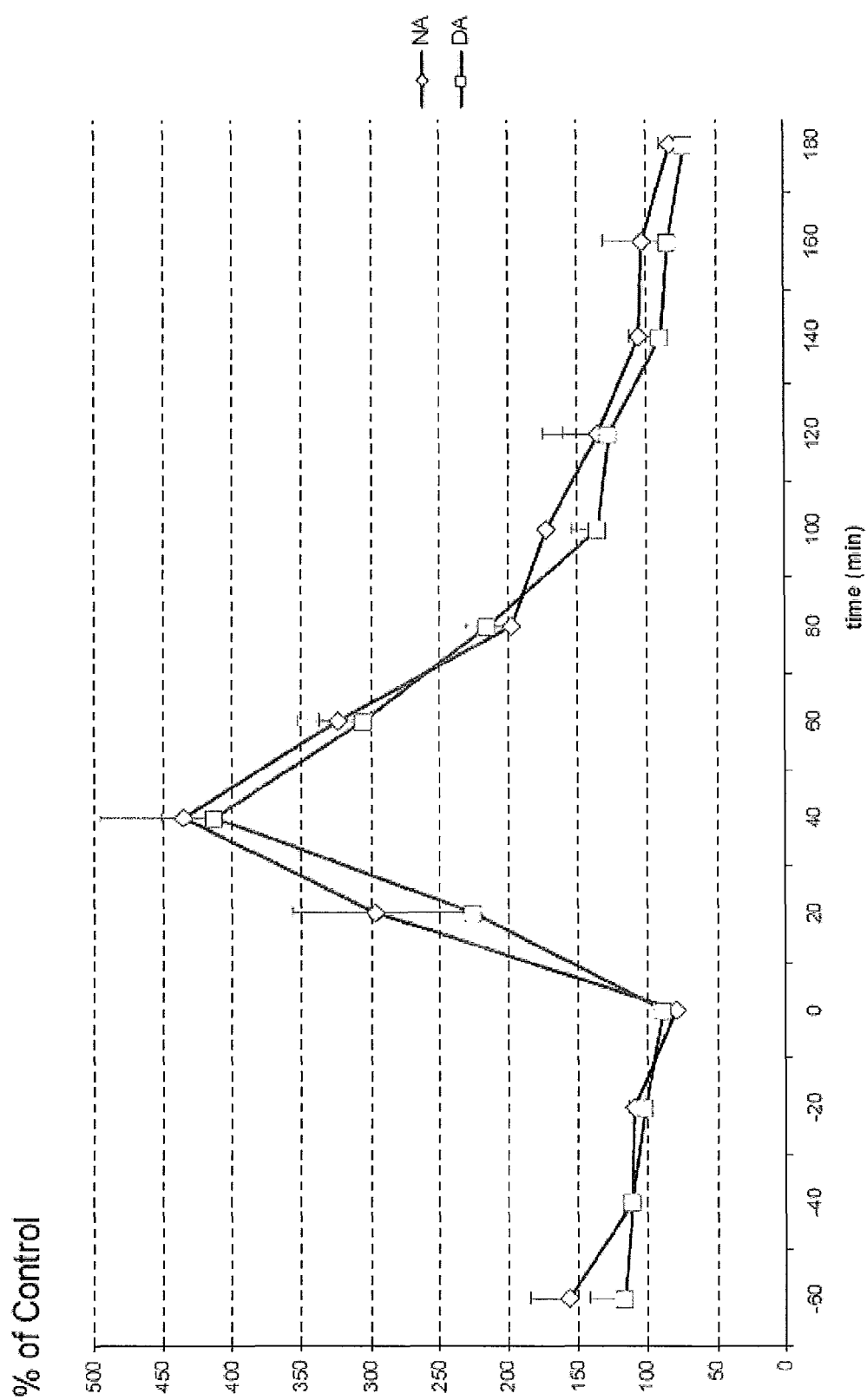
Figure 6:
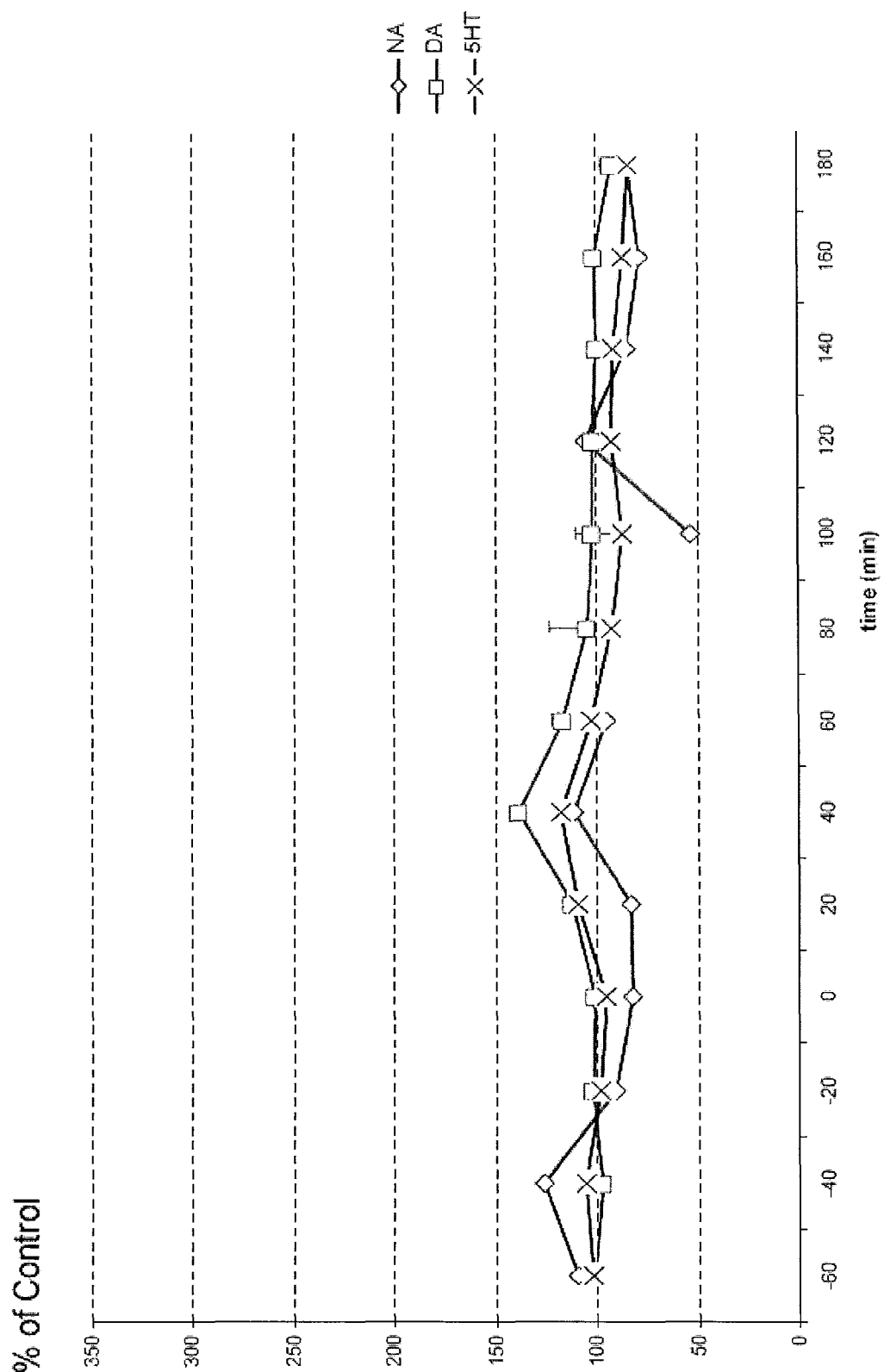
Figure 7:
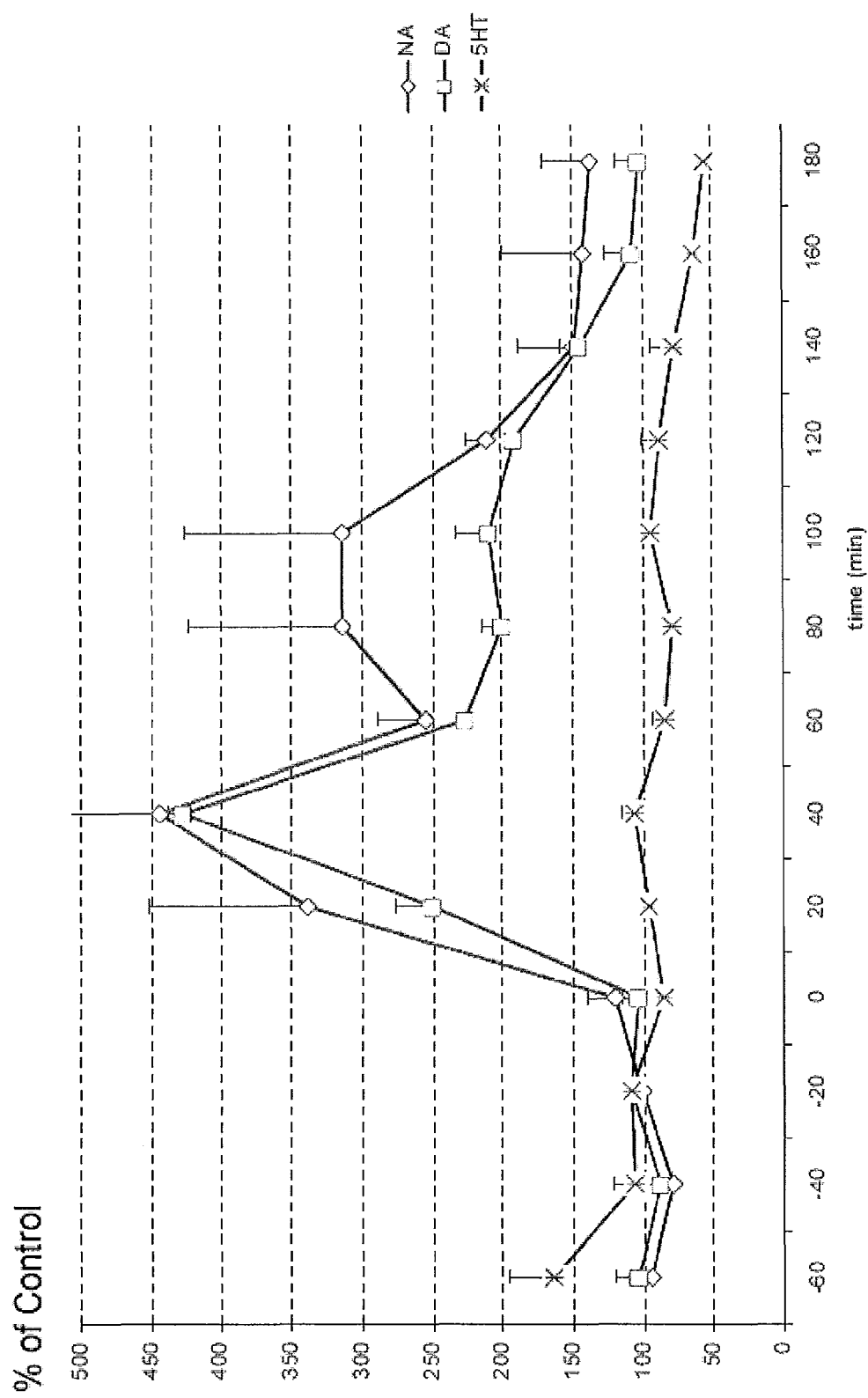
Figure 8:
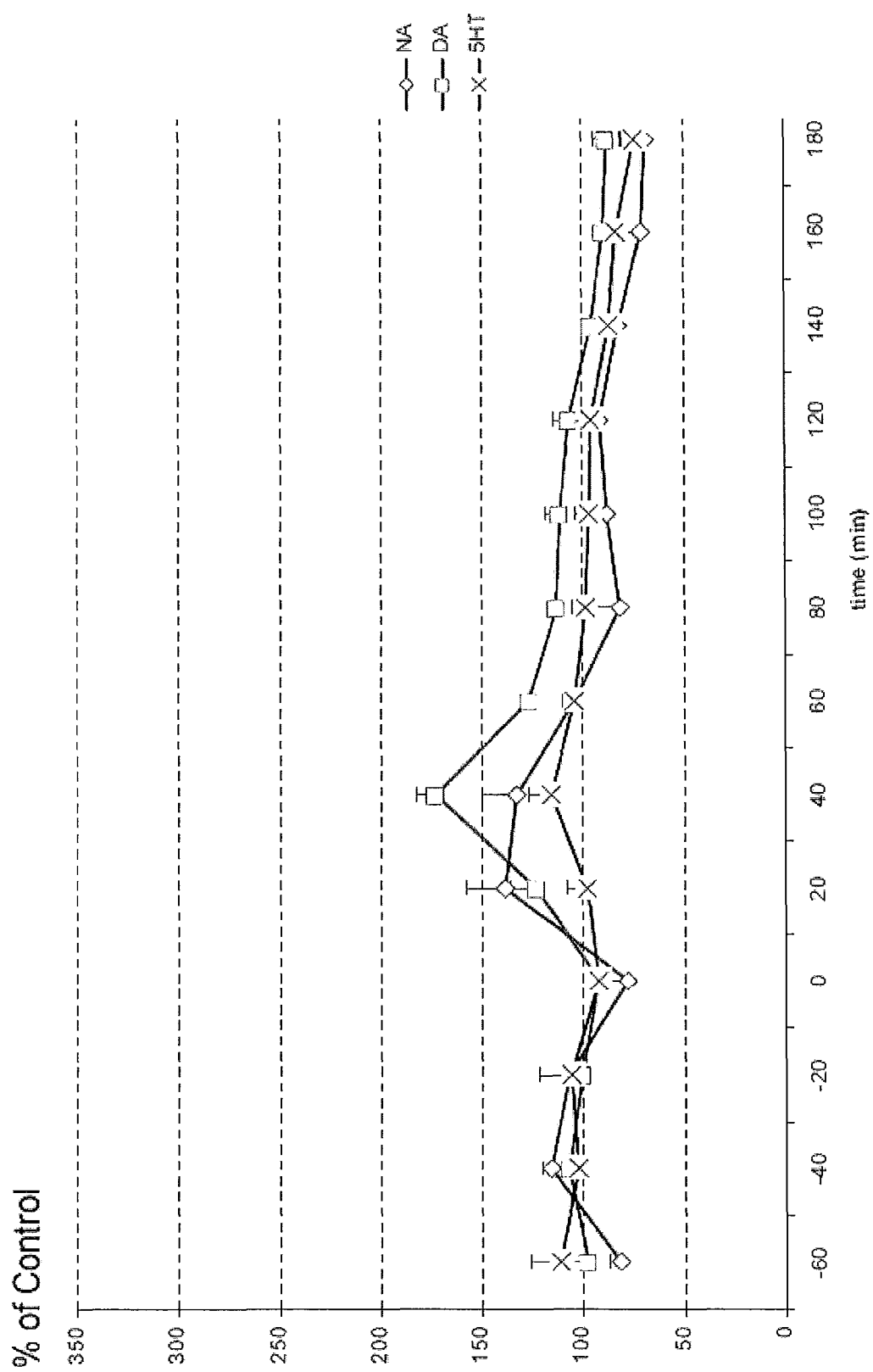
Figure 9:
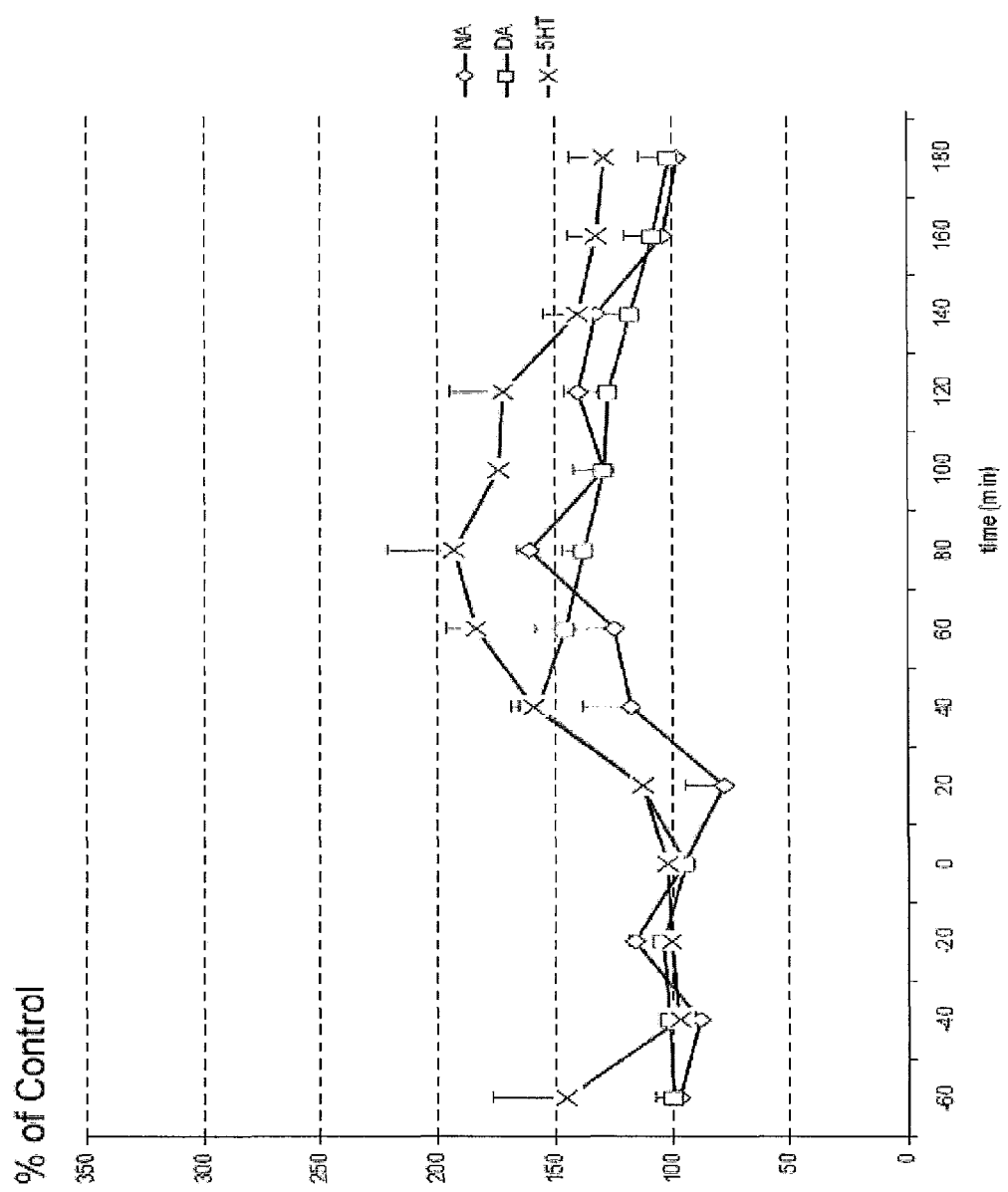
Figure 10:
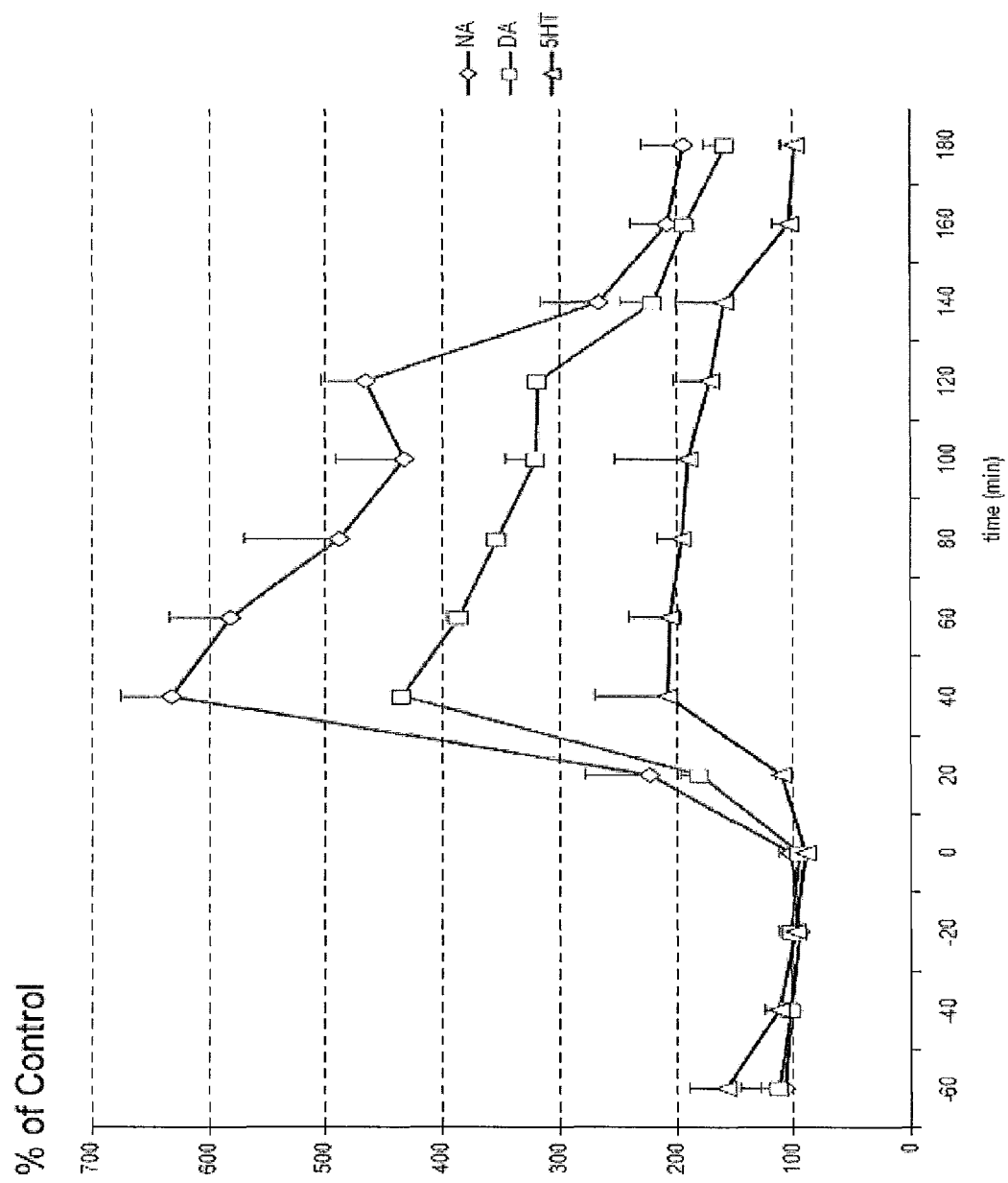

Example 1 is injected (s.c.) at time-point 0. The values depicted in FIG. 1 represent percent of control in relation to baseline values. The microdialysis was performed in awake and freely moving rats. Dopamine=DA; Norepinephrine=NA; Serotonin=5-HT; Error-bars=SEM FIG. 2. Example 1, 50 µmol/kg s.c. striatum amines Example 1 is injected (s.c.) at time-point 0. The values depicted in FIG. 2 represent percent of control in relation to baseline values. The microdialysis was performed in awake and freely moving rats. Dopamine=DA; Norepinephrine=NA; Serotonin=5-HT; Error-bars=SEM FIG. 3. Example 2, 50 µmol/kg s.c. p.f. cortex amines Example 2 is injected (s.c.) at time-point 0. The values depicted in FIG. 3 represent percent of control in relation to baseline values. The microdialysis was performed in awake and freely moving rats. Dopamine=DA; Norepinephrine=NA; Serotonin=5-HT; Error-bars=SEM FIG. 4. Example 2, 50 µmol/kg s.c. striatum amines Example 2 is injected (s.c.) at time-point 0. The values depicted in FIG. 4 represent percent of control in relation to baseline values. The microdialysis was performed in awake and freely moving rats. Dopamine=DA; Norepinephrine=NA; Serotonin=5-HT; Error-bars=SEM FIG. 5: Example 9, 50 µmol/kg s.c. p.f. cortex amines Example 9 is injected (s.c.) at time-point 0. The values depicted in FIG. 5 represent percent of control in relation to baseline values. The microdialysis was performed in awake and freely moving rats. Dopamine=DA; Norepinephrine=NA; Serotonin=5-HT; Error-bars=SEM FIG. 6. Example 9, 50 µmol/kg s.c. striatum amines Example 9 is injected (s.c.) at time-point 0. The values depicted in FIG. 6 represent percent of control in relation to baseline values. The microdialysis was performed in awake and freely moving rats. Dopamine=DA; Norepinephrine=NA; Serotonin=5-HT; Error-bars=SEM FIG. 7: Example 11, 50 µmol/kg s.c. p.f. cortex amines Example 11 is injected (s.c.) at time-point 0. The values depicted in FIG. 7 represent percent of control in relation to baseline values. The microdialysis was performed in awake and freely moving rats. Dopamine=DA; Norepinephrine=NA; Serotonin=5-HT; Error-bars=SEM FIG. 8. Example 11, 50 µmol/kg s.c. striatum amines Example 11 is injected (s.c.) at time-point 0. The values depicted in FIG. 8 represent percent of control in relation to baseline values. The microdialysis was performed in awake and freely moving rats. Dopamine=DA; Norepinephrine=NA; Serotonin=5-HT; Error-bars=SEM FIG. 9. Example 12 50 µmol/kg s.c. striatum amines Example 12 is injected (s.c.) at time-point 0. The values depicted in FIG. 9 represent percent of control in relation to baseline values. The microdialysis was performed in awake and freely moving rats. Dopamine=DA; Norepinephrine=NA; Serotonin=5-HT; Error-bars=SEM FIG. 10. Example 12, 50 µmol/kg s.c. p.f. cortex amines Example 12 is injected (s.c.) at time-point 0. The values depicted in FIG. 10 represent percent of control in relation to baseline values. The microdialysis was performed in awake and freely moving rats. Dopamine=DA; Norepinephrine=NA; Serotonin=5-HT; Error-bars=SEM Comparative Examples

FIGS. 11-21

Figure 11:
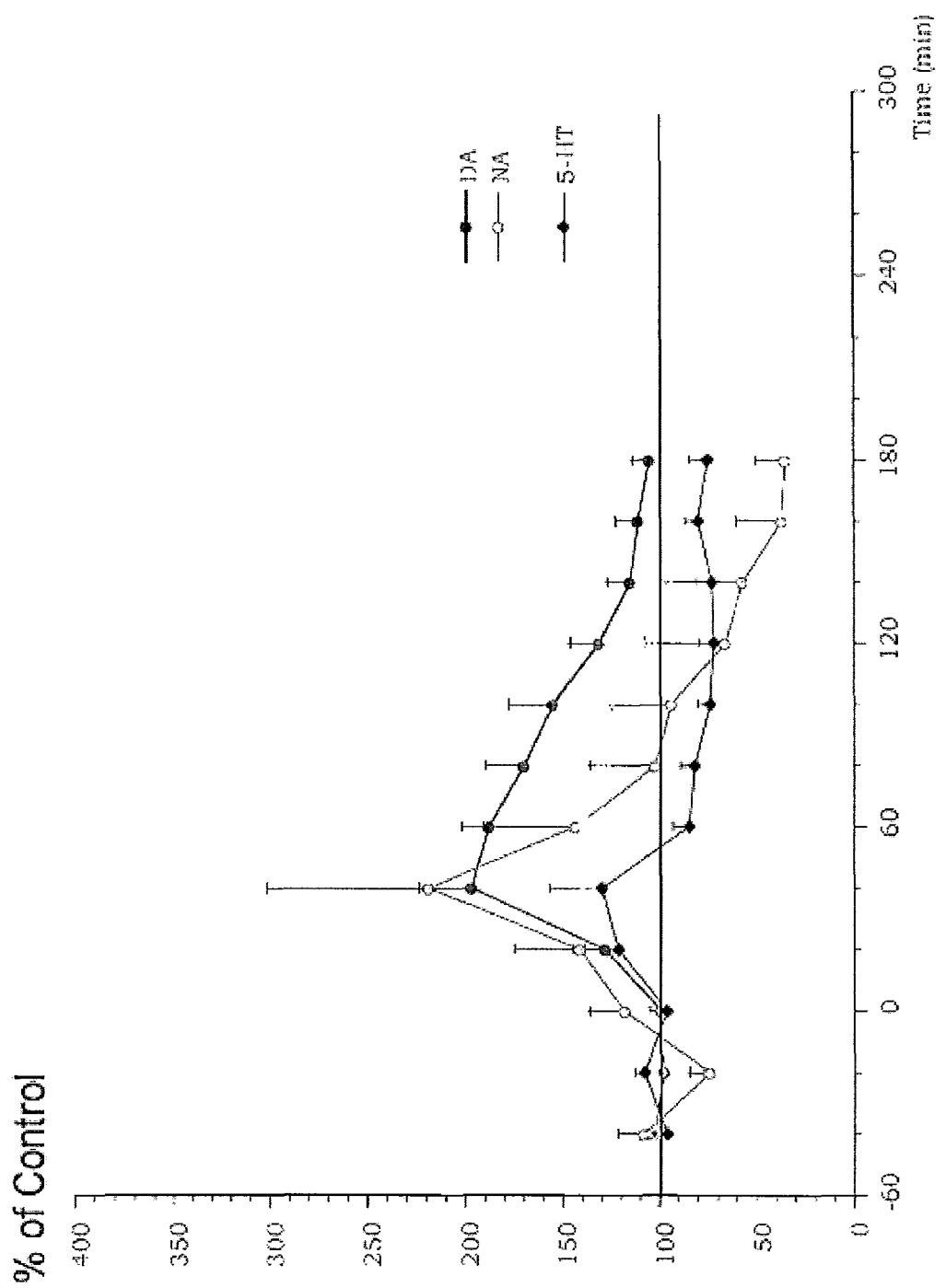
Figure 12:
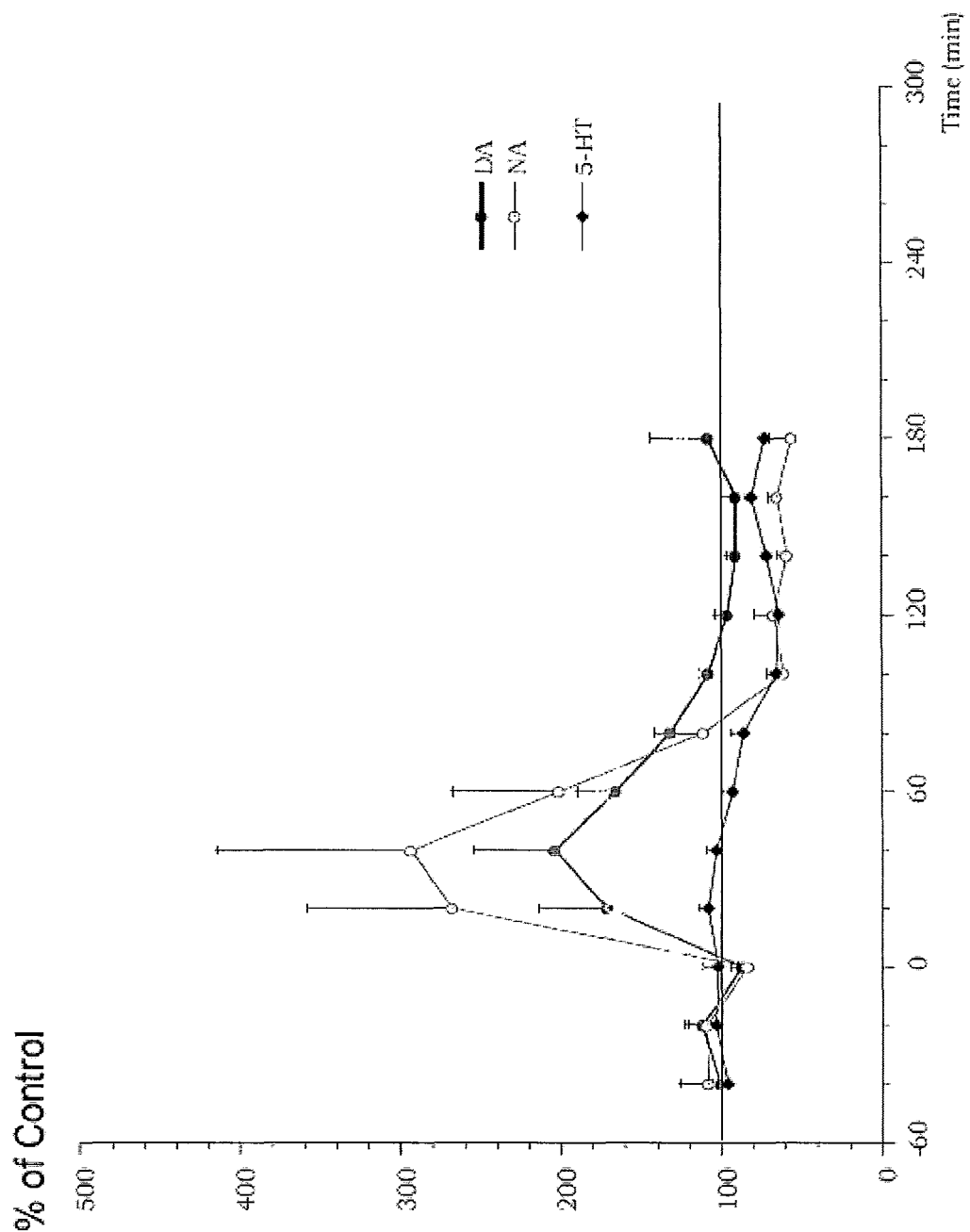
Figure 13:
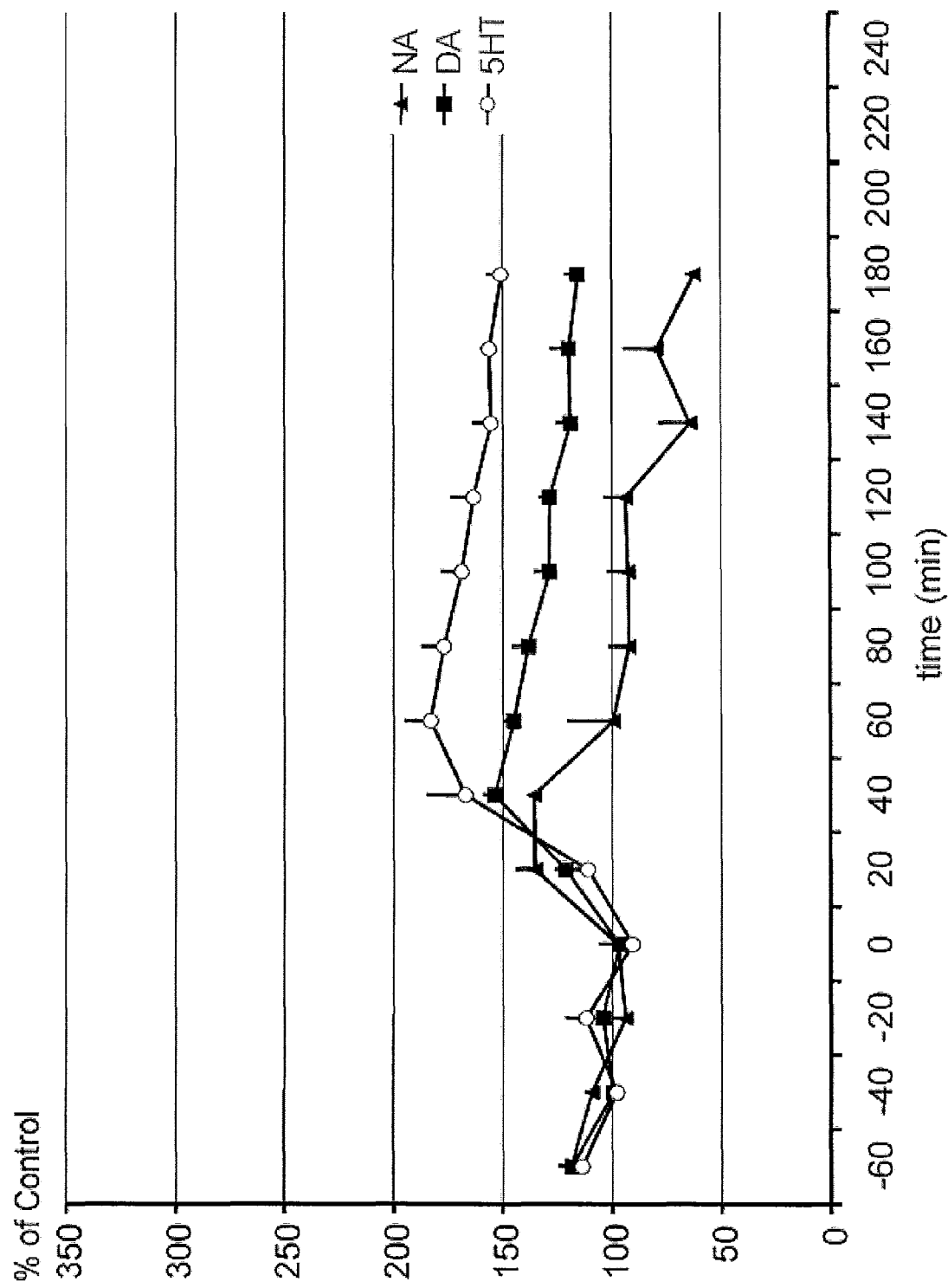
Figure 14:
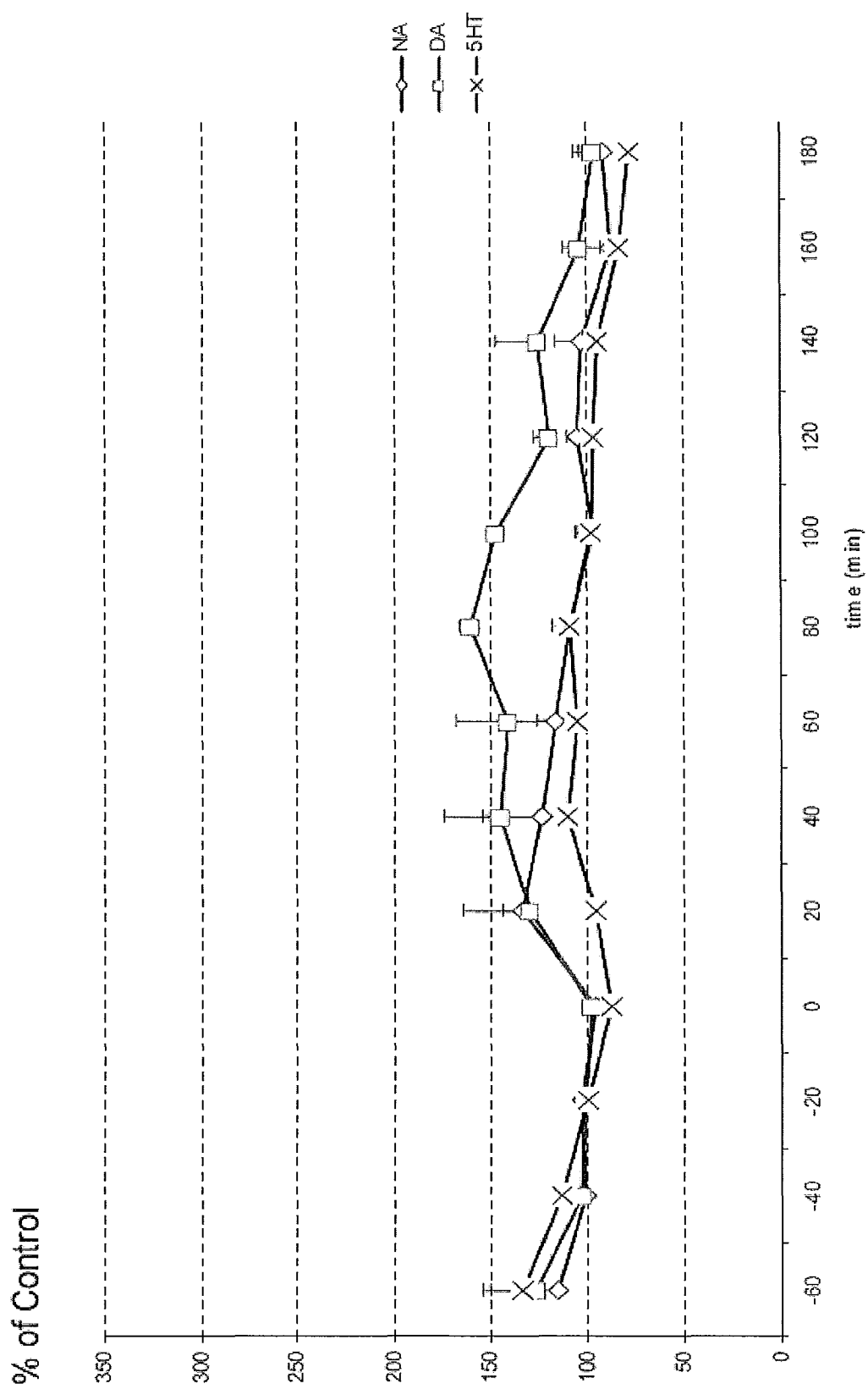
Figure 15:
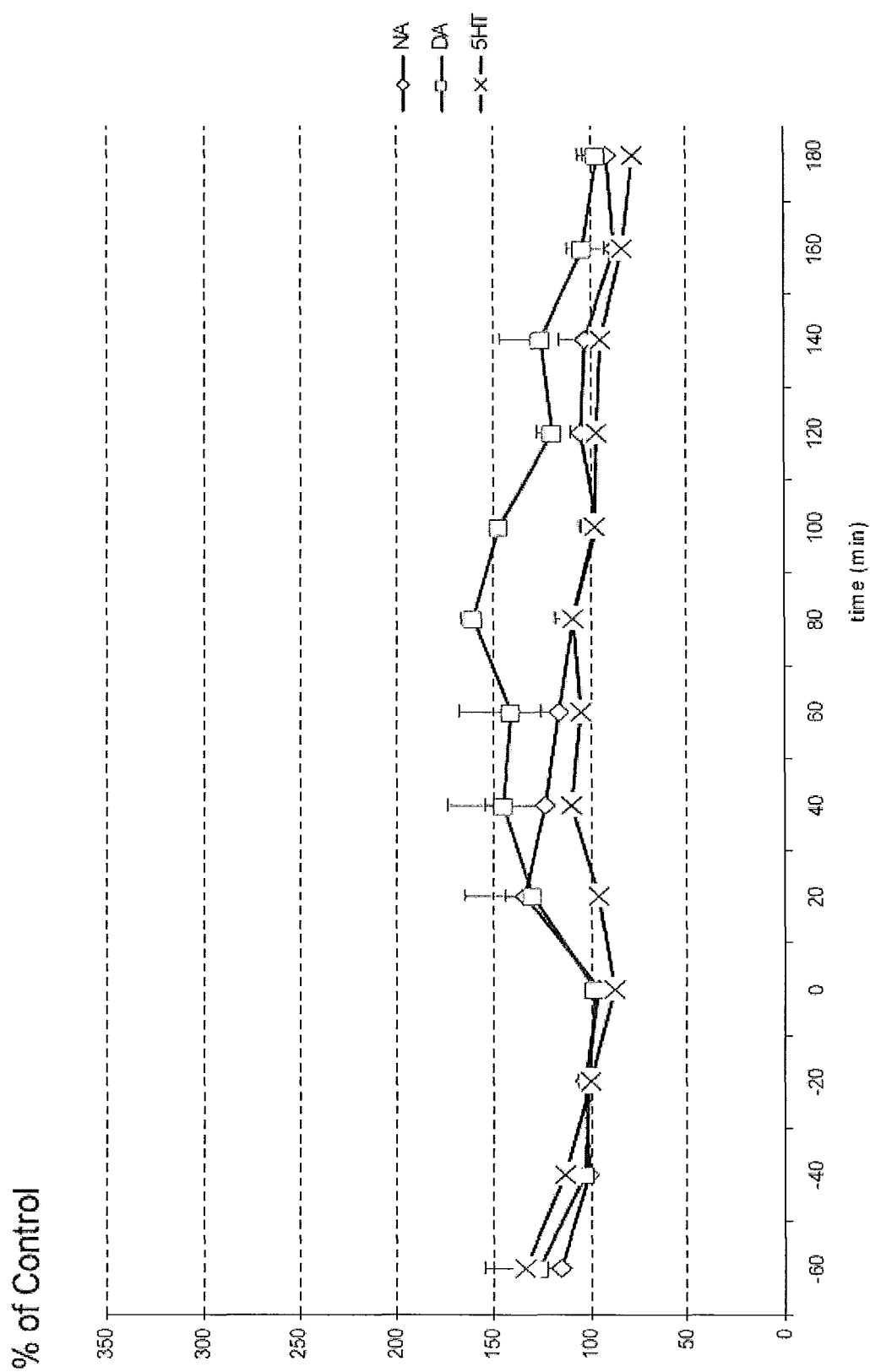
Figure 16:
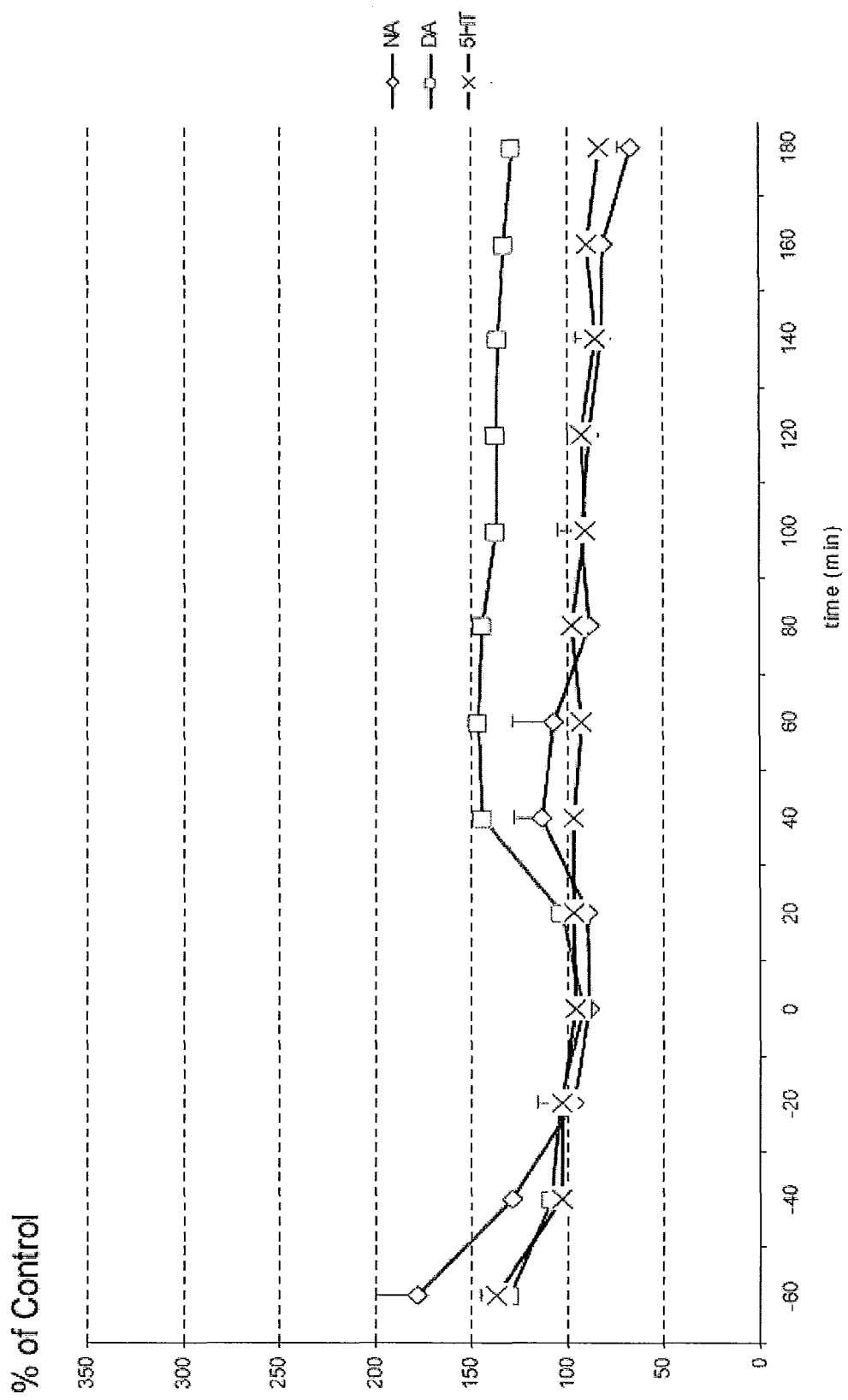
Figure 17:
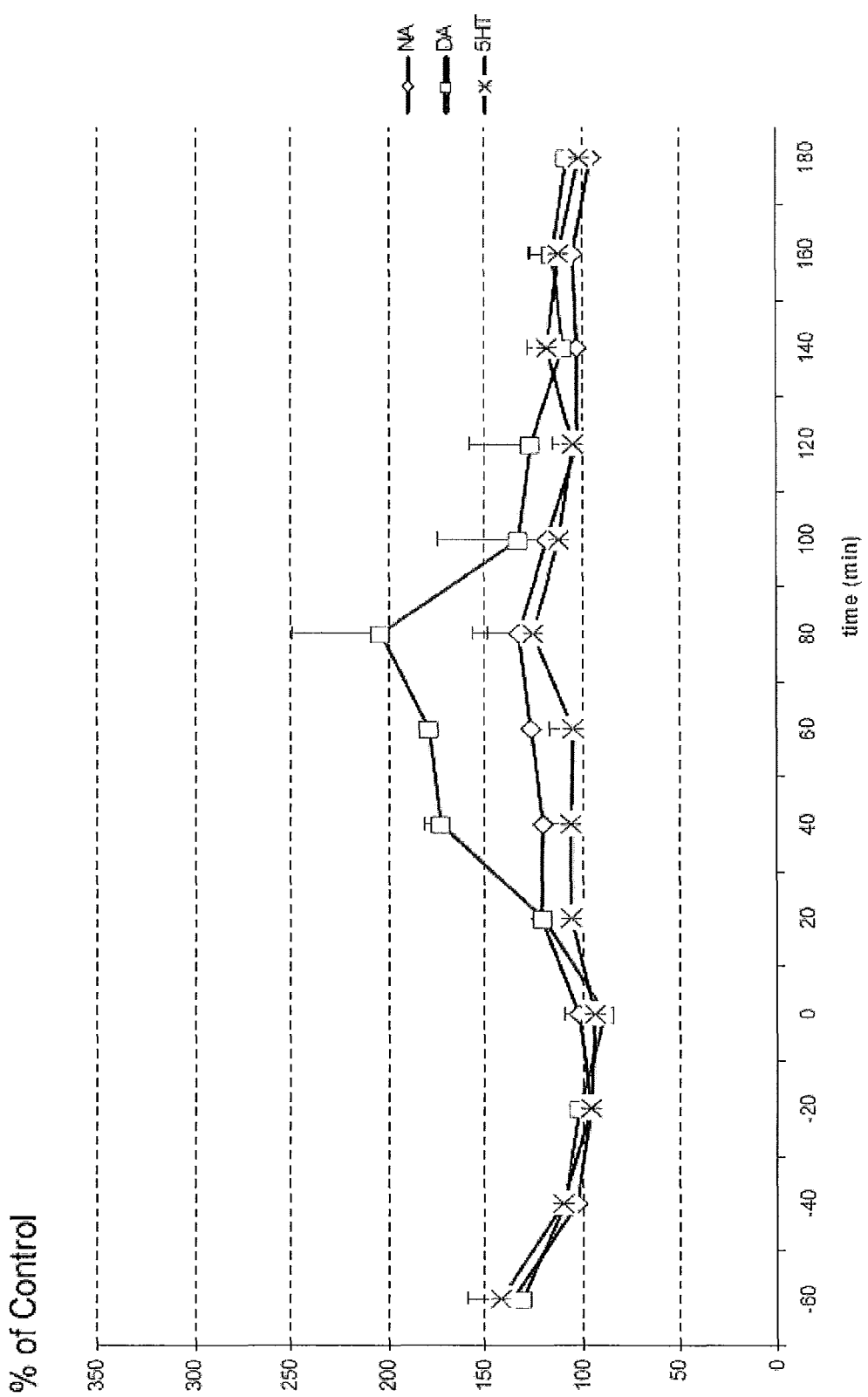
Figure 18:
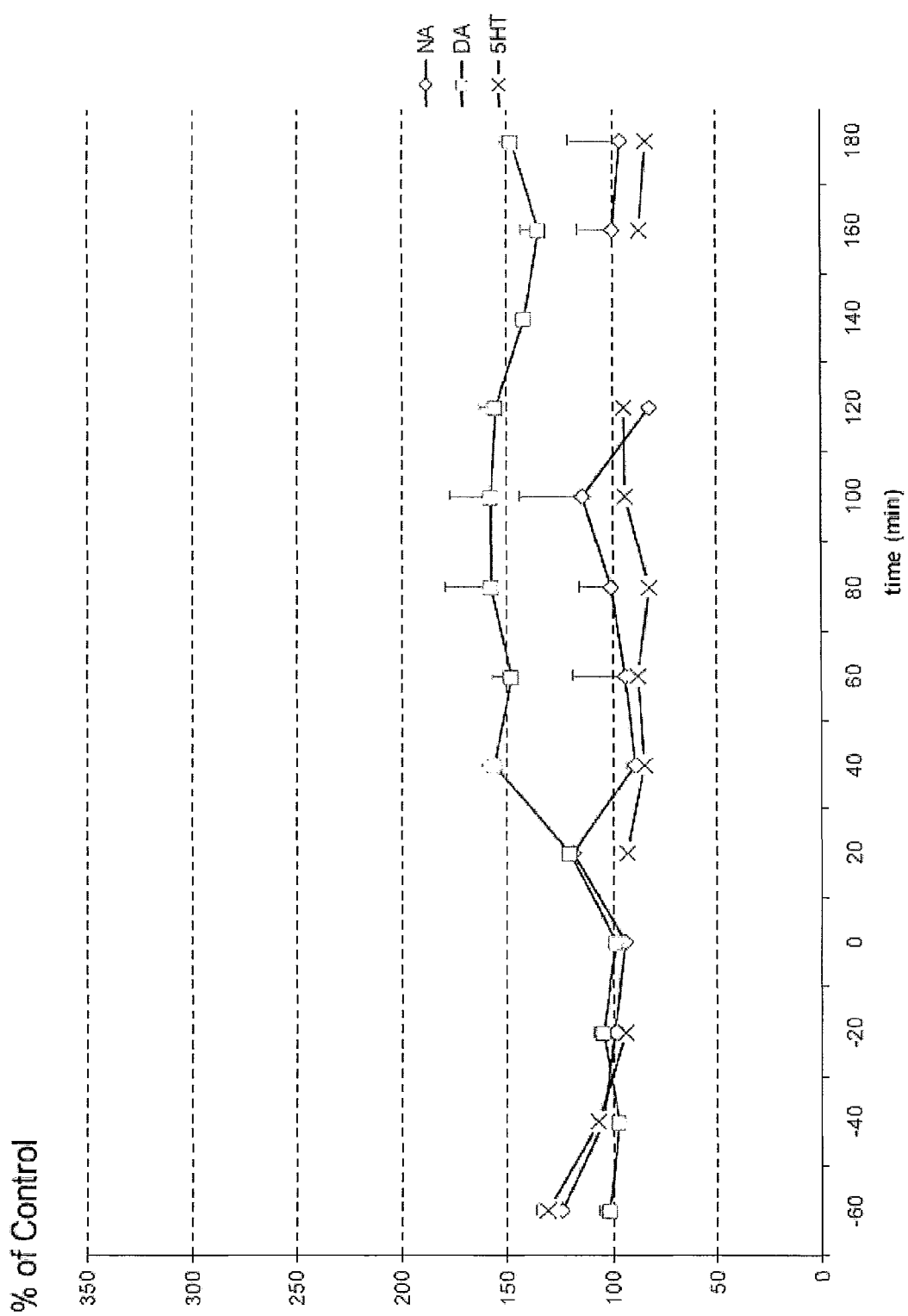
Figure 19:
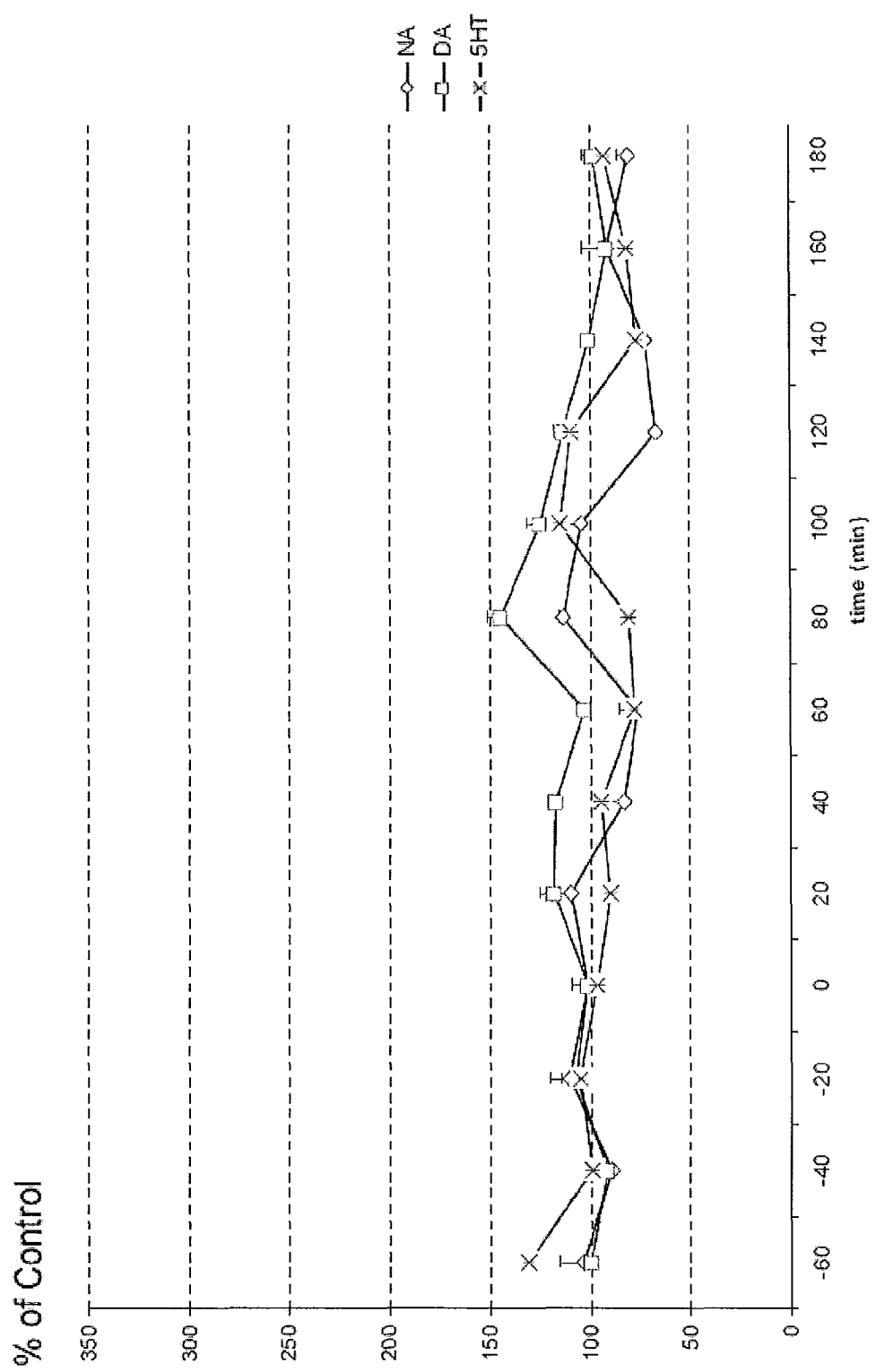
Figure 20:
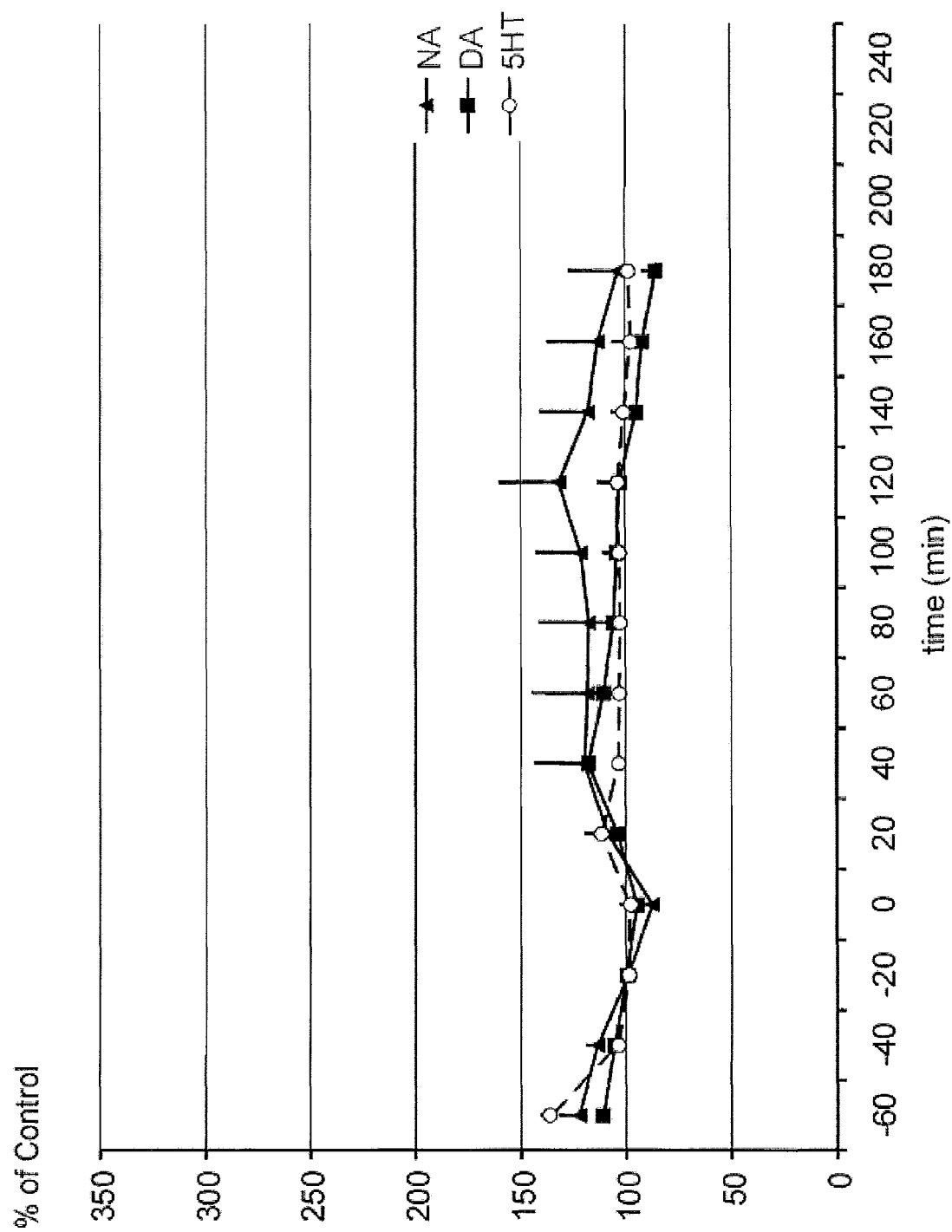
Figure 21:
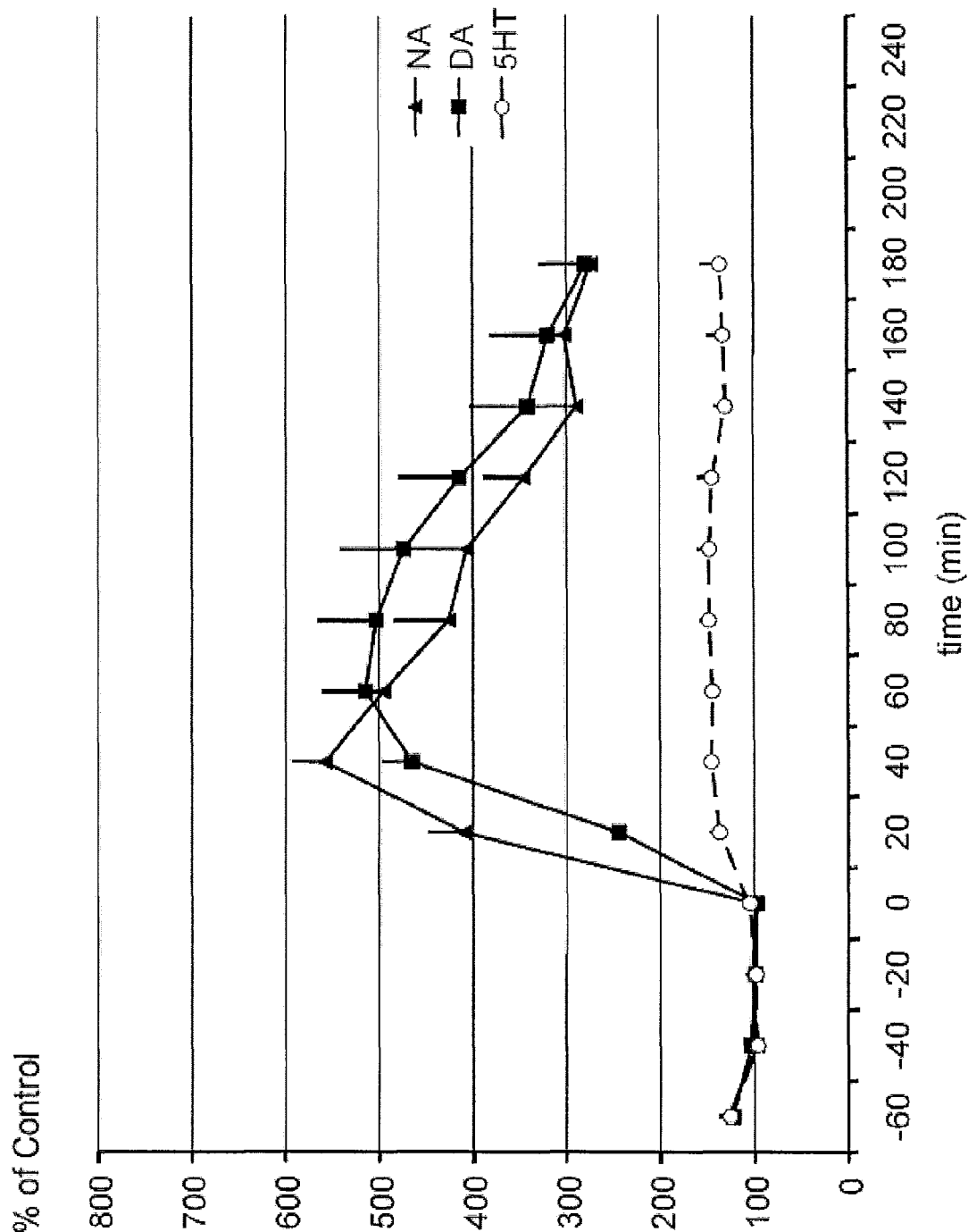

FIG. 11. (S)-(−)-3-[3-methylsulfonyl)phenyl]-1-propylpiperidine (Example 16 in J. Med. Chem. 1994, 37, 2735) 50 µmol/kg s.c. striatum (S)-(−)-3-[3-methylsulfonyl)phenyl]-1-propylpiperidine is injected (s.c) at time-point 0. The values depicted in FIG. 11 represent percent of control in relation to baseline values. The microdialysis was performed in awake and freely moving rats. Dopamine=DA; Norepinephrine=NA; Serotonin=5-HT Error-bars=SEM FIG. 12. (S)-(−)-3-[3-methylsulfonyl)phenyl]-1-propylpiperidine (Example 16 in J. Med. Chem. 1994, 37, 2735) 50 µmol/kg s.c. p.f. cortex (S)-(−)-3-[3-methylsulfonyl)phenyl]-1-propylpiperidine is injected (s.c) at time-point 0. The values depicted in FIG. 12 represent percent of control in relation to baseline values. The microdialysis was performed in awake and freely moving rats. Dopamine=DA; Norepinephrine=NA; Serotonin=5-HT Error-bars=SEM FIG. 13. 4-(4-chloro-3-trifluoromethyl-phenyl)-1-propyl-piperidine (Example 9 in WO01/46146) 50 µmol/kg s.c. striatum amines 4-(4-chloro-3-trifluoromethyl-phenyl)-1-propyl-piperidine is injected (s.c) at time-point 0. The values depicted in FIG. 13 represent percent of control in relation to baseline values. The microdialysis was performed in awake and freely moving rats. Dopamine=DA; Norepinephrine=NA; Serotonin=5-HT; Error-bars=SEM FIG. 14. Example 3 of WO 2005/121092 50 µmol/kg s.c. striatum amines Example 3 of WO 2005/121092 is injected (s.c) at time-point 0. The values depicted in FIG. 14 represent percent of control in relation to baseline values. The microdialysis was performed in awake and freely moving rats. Dopamine=DA; Norepinephrine=NA; Serotonin=5-HT Error-bars=SEM FIG. 15. Example 3 of WO 2005/121092 50 µmol/kg s.c. p.f. cortex 4-(4-fluoro-3-trifluoromethyl-phenyl)-1-ethyl-piperidine is injected (s.c) at time-point 0. The values depicted in FIG. 15 represent percent of control in relation to baseline values. The microdialysis was performed in awake and freely moving rats. Dopamine=DA; Norepinephrine=NA; Serotonin=5-HT; Error-bars=SEM FIG. 16. Example 8 of WO 2005/121092 50 µmol/kg s.c. striatum amines 4-(4-fluoro-3-trifluoromethyl-phenyl)-1-ethyl-piperidine is injected (s.c) at time-point 0. The values depicted in FIG. 16 represent percent of control in relation to baseline values. The microdialysis was performed in awake and freely moving rats. Dopamine=DA; Norepinephrine=NA; Serotonin=5-HT; Error-bars=SEM FIG. 17. Example 8 of WO 2005/121092 50 µmol/kg s.c. p.f. cortex Example 8 of WO 2005/121092 is injected (s.c) at time-point 0. The values depicted in FIG. 17 represent percent of control in relation to baseline values. The microdialysis was performed in awake and freely moving rats. Dopamine=DA; Norepinephrine=NA; Serotonin=5-HT; Error-bars=SEM FIG. 18. Example 2 of WO 2005/121092 50 µmol/kg s.c. striatum amines Example 2 of WO 2005/121092 is injected (s.c) at time-point 0. The values depicted in FIG. 18 represent percent of control in relation to baseline values. The microdialysis was performed in awake and freely moving rats. Dopamine=DA; Norepinephrine=NA; Serotonin=5-HT; Error-bars=SEM FIG. 19. Example 2 of WO 2005/121092 50 µmol/kg s.c. p.f. cortex Example 2 of WO 2005/121092 is injected (s.c) at time-point 0. The values depicted in FIG. 19 represent percent of control in relation to baseline values. The microdialysis was performed in awake and freely moving rats. Dopamine=DA; Norepinephrine=NA; Serotonin=5-HT; Error-bars=SEM FIG. 20. Mirtazapine (remeron) 10 mg/kg s.c. p.f. striatum Remeron is injected (s.c.) at time-point 0. The values depicted in FIG. 20 represent percent of control in relation to baseline values. The microdialysis was performed in awake and freely moving rats. Dopamine=DA; Norepinephrine=NA; Serotonin=5-HT; Error-bars=SEM FIG. 21. Mirtazapine (Remeron) 10 mg/kg s.c. p.f. cortex Remeron is injected (s.c.) at time-point 0. The values depicted in FIG. 21 represent percent of control in relation to baseline values. The microdialysis was performed in awake and freely moving rats. Dopamine=DA; Norepinephrine=NA; Serotonin=5-HT; Error-bars=SEM

REFERENCES

Arnsten A. F. T. and Li B. (2005) Neurobiology of executive functions: Catecholamine influences on prefrontal cortical functions BIOL PSYCHIATRY 2005; 57:1377-1384 Biederman, J. Attention-Deficit/Hyperactivity Disorder: A selective overview BIOL PSYCHIATRY 2005; 57:1215-1220.

Harrison, P. J. and Weinberger, D. R. (2005) Schizophrenia genes, gene expression and neuropathology. on the matter of their convergence. Molecular Psychiatry 10: 40-68.

Moghaddam, B. and Bunney, B. S. (1990) Acute effects of typical and atypical antipsychotic drugs on the release of dopamine from prefrontal cortex, nucleus accumbens, and striatum of the rat: an in vivo microdialysis study. J. Neurochem 54, 5:1755-1759.

Deutch A Y, Moghaddam B, Innis R B, Krystal J H, Aghajanian G K, Bunney B S, Charney D S. (1991) Mechanisms of action of atypical antipsychotic drugs. Implications for novel therapeutic strategies for schizophrenia. Schizophr Res. March-April; 4(2):121-56.

Pliszka, S. R. (2005) The neuropsychopharmacology of attention-deficit/hyperactivity disorder. Biol Psychiatry. 2005 Jun. 1; 57(11):1385-90. Review.

Ungerstedt, U. (1991). "Microdialysis-principles and applications for studies in animals and man." J. Int. Med. 230: 365-373.

Ungerstedt, U., M. Herrera-Marschitz, U. Jungnelius, L. Stahle, U. Tossman and T. Zetterström (1982). Dopamine Synaptic Mechanisms Reflected in Studies Combining Behavioural Recordings and Brain Dialysis. Advances in Dopamine Research. M. Kohksa. Oxford, Perganon Press. 37: 219-231.

Devoto, P., G. Flore, L. Pira, G. Longu and G. L. Gessa (2004). "Mirtazapine-induced corelease of dopamine and norepinephrine from noradrenergic neurons in the medial prefrontal and occipital cortex." Eur J Pharmacol 487(1-3): 105-11.

Millan, M. J., F. Lejeune and A. Gobert (2000). "Reciprocal autoreceptor and heteroreceptor control of serotonergic, dopaminergic and noradrenergic transmission in the frontal cortex: relevance to the actions of antidepressant agents." J Psychopharmacol 14(2): 114-38.

Tanda, G., E. Carboni, R. Frau and G. Di Chiara (1994). "Increase of extracellular dopamine in the prefrontal cortex: a trait of drugs with antidepressant potential?" Psychopharmacology (Berl) 115(1-2): 285-8.

Goldman-Rakic, P. et al. (2004) Targeting the dopamine D1 receptor in schizophrenia: insights for cognitive dysfunction. Psychopharmacology 174:3-16.

Arnsten, A. (2004) Adrenergic targets for the treatment of cognitive deficits in schizophrenia. Psychopharmacology 174:25-31.

Methods of Preparation

The compounds of the invention may be prepared as outlined below in Scheme 1. However, the invention is not limited to these methods. The compounds may also be prepared as described for structurally-related compounds in the prior art. The reactions can be carried out according to standard procedures (eg. *Comprehensive Organic Transformations: A Guide to Functional Group Preparations* Richard C. Larock, 22 Oct., 1999 Wiley-VCH, ISBN: 0471190314; or *March's Advanced Organic Chemistry: Reactions, Mechanisms, and Structure*, 5th Edition. Michael B. Smith, Jerry March, Jan. 15, 2001 Wiley-Interscience, ISBN: 0471585890) or as described in the working examples. The starting materials for the processes described in the present application are known or may readily be prepared by conventional methods from commercially available chemicals.

Persons skilled in the art will appreciate that, in order to obtain compounds of the invention in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

A synthesis of the compounds of the invention is outlined below in Scheme 1.

Scheme 1

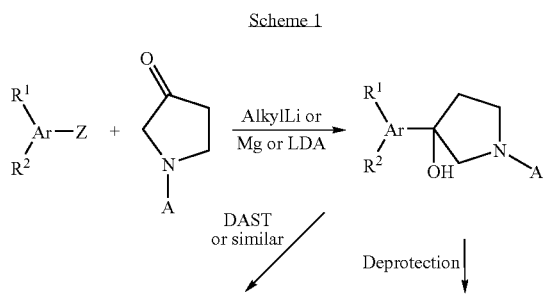

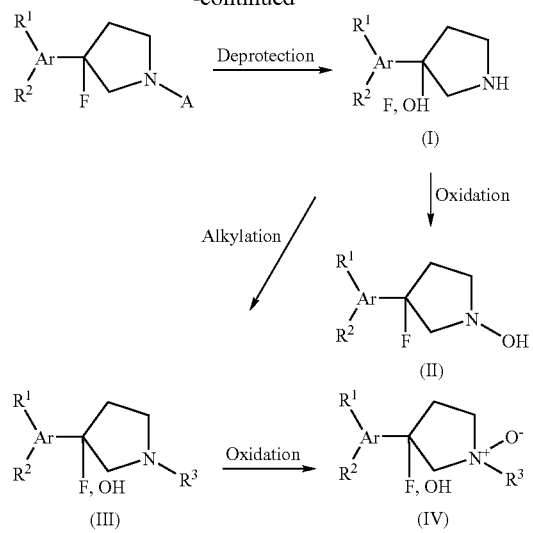

The substituents in Scheme 1 are as follows: Z is a leaving group, A is alkyl or a protecting group, Ar, R1, R2, and R3 are as defined above. Oxidation from (III) to (IV) can take place using standard oxidising procedures and reagents (e.g. *Handbook of Reagents for Organic Synthesis—Oxidising and Reducing Agents*. S. D. Burke, R. L. Danheiser (Eds.); John. Wiley & Sons, Chichester, 1999, ISBN 0-471-97926-0).

The compounds of the present invention may be isolated in any level of purity by standard methods and purification can be achieved by conventional means known to those skilled in the art, such as distillation, recrystallization and chromatography.

Pharmaceutical Compositions

In another aspect the invention provides novel pharmaceutical compositions comprising a therapeutically effective amount of the chemical compound of the invention.

The present invention relates to pharmaceutical compositions comprising the compounds of the present invention, and their use in treating CNS disorders. Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as those mentioned above.

The pharmaceutical composition comprising a compound according to the invention may also comprise substances used to facilitate the production of the pharmaceutical preparation or the administration of the preparations. Such substances are well known to people skilled in the art and may for instance be pharmaceutically acceptable adjuvants, carriers and preservatives.

In clinical practice, the compounds according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate or sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of tablet and capsule formulations suitable for oral administration are given below:

| Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound | 10 |
| Lactose Ph. Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also contain stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Further details on techniques for formulation and administration may be found in the latest edition of Remington's Pharmaceutical Sciences (Maack Publishing Co., Easton, Pa.).

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for

Example 1

(−)-3-(3,5-DIFLUOROPHENYL)-1-ETHYLPYR-ROLIDIN-3-OL

In a sealed tube a mixture of enantiomer E2 of 3-(3,5-difluorophenyl)pyrrolidin-3-ol (0.17 g, 0.85 mmol), acetonitrile (4 mL), sodium carbonate (0.11 g, 2.12 mmol) and iodoethane (0.13 g, 0.85 mmol) was stirred at ambient temperature for 72 h. Water (30 mL) was added and the aqueous phase was extracted with ethyl acetate (2×50 mL), the combined organic phase was dried (MgSO4) and evaporated. Purification by flash chromatography on silica gel (ethyl acetate/methanol, 1:1) gave the title compound (0.11 g). $[\alpha]_D = -21.4°$ (methanol). The amine was converted to the oxalic acid salt and recrystallized from ethanol/diisopropyl ether: M.p. 111-112° C.; MS m/z (relative intensity, 70 eV) 227 (M+, 19), 212 (15), 141 (15), 127 (15), 71 (bp).

Example 2

(+)-3-(3,5-DIFLUOROPHENYL)-1-ETHYLPYR-ROLIDIN-3-OL

In a sealed tube a mixture of enantiomer E1 of 3-(3,5-difluorophenyl)pyrrolidin-3-ol (0.14 g, 0.70 mmol), acetonitrile (4 mL), potassium carbonate (0.09 g, 1.75 mmol) and iodoethane (0.12 g, 0.77 mmol) was heated under microwave irradiation at 100° C. for 5 minutes. Water (30 mL) was added and the aqueous phase extracted with ethyl acetate (2×50 mL), the combined organic phase was dried (MgSO4) and evaporated. Purification by flash chromatography on silica gel (ethyl acetate/methanol, 2:1 to 1:1) gave the title compound (0.11 g). $[\alpha]_D = +18.7°$ (methanol). The amine was converted to the oxalic acid salt and recrystallized from ethanol/diisopropyl ether: M.p. 137-139° C.; MS m/z (relative intensity, 70 eV) 227 (M+, 19), 212 (15), 141 (15), 127 (15), 71 (bp).

Example 3

3-(3-CHLORO-4-FLUOROPHENYL)-1-ETHYLPYRROLIDIN-3-OL

Preparation according to Example 2: 3-(3-chloro-4-fluorophenyl)pyrrolidin-3-ol (0.31 g, 1.46 mmol), acetonitrile (3 mL), potassium carbonate (0.20 g, 1.46 mmol), iodoethane (0.12 mL, 1.5 mmol). Microwave irradiation at 100° C. for 20 minutes. Purification by HPLC on Waters OBD C18, 5 µm (MeOH/33 mM NH3, 55:45). Yield: 0.19 g. The amine was converted to the fumaric acid salt and recrystallized from ethanol/diethyl ether/diisopropyl ether: M.p. 157-158° C.; MS m/z (relative intensity, 70 eV) 243 (M+, 9), 228 (9), 157 (13), 129 (10), 71 (bp).

Example 4

3-(2,3-DIFLUOROPHENYL)-1-ETHYLPYRROLIDIN-3-OL

Preparation according to Example 2: 3-(2,3-difluorophenyl)pyrrolidin-3-ol (0.30 g, 1.50 mmol), acetonitrile (3 mL), potassium carbonate (0.21 g, 1.50 mmol), iodoethane (0.12 mL, 1.50 mmol). Microwave irradiation at 100° C. for 20 minutes. Purification by HPLC on Waters OBD C18, 5 µm (MeOH/33 mM NH3, 1:1). The amine was converted to the fumaric acid salt and recrystallized from ethanol/diethyl ether/diisopropyl ether: M.p. 119-120° C.; MS m/z (relative intensity, 70 eV) 227 (M+, 14), 212 (11), 141 (14), 127 (11), 71 (bp).

Example 5

3-(3-CHLORO-5-FLUOROPHENYL)-1-ETHYLPYRROLIDIN-3-OL

Preparation according to Example 8: 3-(3-chloro-5-fluorophenyl)pyrrolidin-3-ol (0.30 g, 1.4 mmol), acetonitrile (20 mL), sodium carbonate (0.19 g, 3.5 mmol), iodoethane (0.22 g, 1.4 mmol). Yield: 0.17 g. The amine was converted to the oxalic acid salt and recrystallized from ethanol/diethyl ether/diisopropyl ether: M.p. 169-170° C.; MS m/z (relative intensity, 70 eV) 243 (M+, 8), 228 (7), 157 (7), 129 (7), 72 (30), 71 (bp).

Example 6

3-(3,5-DICHLOROPHENYL)-1-ETHYLPYRROLIDIN-3-OL

Preparation according to Example 8: 3-(3,5-dichlorophenyl)pyrrolidin-3-ol (0.34 g, 1.46 mmol), acetonitrile (24 mL), sodium carbonate (0.20 g, 3.65 mmol), iodoethane (0.23 g, 1.46 mmol). Heated at reflux for 15 minutes. Yield: 0.24 g. The amine was converted to the fumaric acid salt and evaporated to a solid residue. MS m/z (relative intensity, 70 eV) 259 (M+, 5), 244 (5), 173 (4), 145 (44), 71 (bp).

Example 7

3-(3,4-DIFLUOROPHENYL)-1-PROPYLPYRROLIDIN-3-OL

Preparation according to Example 1: 3-(3,5-difluorophenyl)pyrrolidin-3-ol (0.34 g, 1.7 mmol), acetonitrile (5 mL), sodium carbonate (0.33 g, 2.4 mmol), iodopropane (0.17 mL, 1.7 mmol). Stirred for 3 h at ambient temperature. Purification on a Biotage (solute SCX-3 SPE column (washed with methanol and eluted with methanol/triethylamine, 4:1). Yield: 0.15 g. The amine was converted to the oxalic acid salt and recrystallized from methanol/diethyl ether: M.p. 131-132° C.; MS m/z (relative intensity, 70 eV) 241 (M+, 9), 212 (bp), 182 (34), 141 (19), 84 (93).

Example 8

3-(3,5-DIFLUOROPHENYL)-1-ETHYLPYRROLIDIN-3-OL

To a mixture of 3-(3,5-difluorophenyl)pyrrolidin-3-ol (0.50 g, 2.5 mmol) in acetonitrile (25 mL) was added sodium carbonate (0.34 g, 6.25 mmol) and iodoethane (0.39 g, 2.5 mmol) and the mixture was refluxed for 1 h. Water (50 mL) was added and the aqueous phase was extracted with ethyl acetate (2×50 mL), the combined organic phase was dried (MgSO4) and evaporated. Purification by flash chromatography on silica gel (ethyl acetate/methanol, 1:1) gave the title compound (0.12 g). The amine was converted to the fumaric acid salt and lyophilized from water. MS m/z (relative intensity, 70 eV) 227 (M+, 19), 212 (15), 141 (15), 127 (15), 71 (bp).

Example 9

3-(3,5-DIFLUOROPHENYL)-1-PROPYLPYRROLIDIN-3-OL

Preparation according to Example 8: 3-(3,5-difluorophenyl)pyrrolidin-3-ol (0.54 g, 2.7 mmol), acetonitrile (30 mL), sodium carbonate (0.38 g, 6.75 mmol), iodopropane (0.26 mL, 2.7 mmol). Yield: 0.22 g. The amine was converted to the fumaric acid salt: M.p. 136-137° C.; MS m/z (relative intensity, 70 eV) 241 (M+, 8), 213 (13), 212 (bp), 182 (34), 84 (60).

Example 10

3-(3,4-DICHLOROPHENYL)-1-ETHYLPYRROLIDIN-3-OL

Preparation according to Example 2: 3-(3,4-difluorophenyl)pyrrolidin-3-ol (0.34 g, 1.46 mmol), acetonitrile (3 mL), a drop of methanol, sodium carbonate (0.20 g, 1.46 mmol), iodoethane (0.12 mL, 1.46 mmol). Yield: 0.18 g. The amine was converted to the fumaric acid salt and recrystallized in ethanol/diethyl ether/diisopropyl ether: M.p. 184-185° C.; MS m/z (relative intensity, 70 eV) 259 (M+, 7), 244 (6), 239 (8), 173 (7), 71 (bp).

Example 11

3-(3,5-DIFLUOROPHENYL)-3-FLUORO-1-METHYLPYRROLIDINE

A mixture of 3-(3,5-difluorophenyl)-3-fluoropyrrolidine (0.17 g, 0.85 mmol) in formic acid (2.45 mL) and aqueous formaldehyde (40%, 2.2 mL) was heated at 85° C. for 1 h. Water (100 mL) and diethyl ether was added, the phases were separated and the aqueous phase was basified by the addition of aqueous sodium hydroxide (5M, 20 mL). The aqueous phase was extracted with ethyl acetate (2×50 mL), the combined organic phase was dried (MgSO4) and evaporated. Purification by flash chromatography on silica gel (ethyl acetate/methanol, 1:0 to 1:1) gave the title compound (0.12 g). The amine was converted to the oxalic acid salt and recrystallized from methanol/diethyl ether/diisopropyl ether: M.p. 128-129° C.; MS m/z (relative intensity, 70 eV) 215 (M+, bp), 194 (29), 193 (36), 151 (33), 57 (92).

Example 12

3-(3,4-DIFLUOROPHENYL)-1-ETHYLPYRROLIDIN-3-OL

Preparation according to Example 8: 3-(3,4-difluorophenyl)pyrrolidin-3-ol (0.38 g, 1.9 mmol), acetonitrile (20 mL), sodium carbonate (0.26 g, 4.75 mmol), iodoethane (0.29 g, 1.9 mmol). Refluxed 2 h. Purification by HPLC on Waters OBD C18, 5 µm (MeOH/33 mM NH3, 35:65 to 50:50). Yield: 0.26 g. The amine was converted to the fumaric acid salt and recrystallized from 2-propanol/diisopropyl ester: M.p. 157-158° C.; MS m/z (relative intensity, 70 eV) 227 (M+, 26), 212 (18), 141 (30), 127 (23), 113 (22), 71 (bp).

Example 13

3-(3,5-DIFLUOROPHENYL)-3-FLUOROPYRROLIDINE

A mixture of 1-benzyl-3-(3,5-difluorophenyl)-3-fluoropyrrolidine (0.65 g, 2.2 mmol) and ammonium formiate (1.4 g, 22 mmol) in methanol (50 mL) was purged with nitrogen and palladium on carbon (65 mg) was added. The mixture was refluxed for 8 h and palladium on carbon (30 mg) was added at 4 h, 6 h and 7 h respectively. The mixture was cooled to ambient temperature and filtered through a pad of celite. The filtrate was evaporated, aqueous sodium carbonate (10%, 50 mL) was added and the aqueous phase was extracted with dichloromethane (2×50 mL). Purification by flash column chromatography on silica gel (ethyl acetate/methanol, 1:1 to 0:1) gave the title compound (0.14 g). The amine was converted to the oxalic acid salt and recrystallized from methanol/diethyl ether: M.p. 176-177° C.; MS m/z (relative intensity, 70 eV) 201 (M+, bp), 181 (20), 180 (29), 158 (21), 151 (53).

Example 14

3-(3,5-DICHLOROPHENYL)-3-FLUOROPYRROLIDINE

Preparation according to Preparation 2: tert-Butyl 3-(3,5-dichlorophenyl)-3-fluoro-pyrrolidin-1-carboxylate (0.45 g, 1.34 mmol), dichloromethane (2 mL), trifluoroacetic acid (2 mL). Stirred for 4 h at ambient temperature. Purification on a Biotage Isolute SCX-3 SPE column (washed with methanol and eluted with methanol/triethylamine, 4:1) followed by HPLC on Waters OBD C18, 5 µm (MeOH/33 mM NH3, 20:80 to 60:40) and flash chromatography on silica gel (ethyl acetate/methanol, 1:0 to 1:1). Yield: 0.15 g. The amine was converted to the hydrochloric acid salt and recrystallized from ethanol/diethyl ether: M.p. 201-202° C.; MS m/z (relative intensity, 70 eV) 235 (M+, 64), 233 (M+, bp), 213 (28), 133 (49), 120 (32).

Example 15

3-(2,4-DIFLUOROPHENYL)-1-METHYLPYRROLIDIN-3-OL

Preparation according to Example 26: 3-(2,4-difluorophenyl)-3-pyrrolidin-3-ol (0.44 g, 2.21 mmol), formic acid (6.41 mL), aqueous formaldehyde (40%, 5.75 mL). 85° C. for 3 h. Yield: 0.395 g. The amine was converted to the oxalic acid salt and recrystallized from methanol/ethanol/diethyl ether: M.p. 117-119° C.; MS m/z (relative intensity, 70 eV) 213 (M+, 27), 194 (38), 127 (19), 58 (41), 57 (bp).

Example 16

3-(3,4-DIFLUOROPHENYL)-1-METHYLPYRROLIDIN-3-OL

Preparation according to Example 26: 3-(3,4-difluorophenyl)-pyrrolidin-3-ol (1.32 g, 6.63 mmol), formic acid (19.2 mL), aqueous formaldehyde (40%, 17.2 mL). 60° C. for 24 h. Yield: 0.83 g. The amine was converted to the fumaric acid salt and recrystallized from methanol/diethyl ether/diisopropyl ether: M.p. 164-166° C.; MS m/z (relative intensity, 70 eV) 213 (M+, 7), 141 (10), 113 (10), 58 (43), 57 (bp).

Example 17

3-(2,3-DICHLOROPHENYL)-1-ETHYLPYRROLIDIN-3-OL

In a sealed tube a mixture of 3-(2,3-dichlorophenyl)pyrrolidin-3-ol (0.35 g, 1.51 mmol), acetonitrile (20 mL), potassium carbonate (0.019 g, 3.77 mmol) and iodoethane (0.24 g, 1.51 mmol) was stirred at ambient temperature over night, additional iodoethane (0.02 mL) was added and the resulting mixture was stirred over night. Water (50 mL) was added, the aqueous phase was extracted with tert-butyl methyl ether (2×50 mL) and the combined organic phase was dried (MgSO4) and evaporated. Purification by flash column chromatography on silica gel (ethyl acetate/methanol, 1:0 to 1:1) gave the title compound (0.13 g). The amine was converted to the oxalic acid salt and recrystallized from methanol/ethanol/diethyl ether: M.p. 206-207° C.; MS m/z (relative intensity, 70 eV) 259 (M+, 5), 173 (7), 145 (6), 72 (23), 71 (bp).

Example 18

3-(3,5-DIFLUOROPHENYL)-1-METHYLPYRROLIDIN-3-OL

Preparation according to Example 11: 3-(3,5-difluorophenyl)pyrrolidin-3-ol (0.125 g, 0.628 mmol), formic acid (1.82 mL), aqueous formaldehyde (40%, 1.63 mL). 65° C.; over night. The amine was converted to the oxalic acid salt and recrystallized from methanol/diethyl ether (0.126 g). M.p. 159-162° C.; MS m/z (relative intensity, 70 eV) 213 (M+, 27), 141 (13), 113 (15), 58 (32), 57 (bp).

Example 19

3-(3-CHLORO-2-FLUOROPHENYL)-1-METHYLPYRROLIDIN-3-OL

Preparation according to Example 26: 3-(3-chloro-2-fluorophenyl)-pyrrolidin-3-ol (0.6 g, 2.78 mmol), formic acid (8.1 mL), aqueous formaldehyde (40%, 7.2 mL). Purification by flash chromatography on silica gel (ethyl acetate/methanol, 2:8 to 3:8) and by HPLC on Waters OBD C18, 5 μm (MeOH/33 mM NH3, 20:80 to 100:0). Yield: 0.3 g. The amine was converted to the fumaric acid salt and evaporated to a solid residue: MS m/z (relative intensity, 70 eV) 229 (M+, 10), 157 (8), 129 (5), 58 (28), 57 (bp).

Example 20

3-(3-CHLORO-2-FLUOROPHENYL)-1-ETHYLPYRROLIDIN-3-OL

In a sealed tube a mixture of 3-(3-chloro-2-fluorophenyl) pyrrolidin-3-ol (0.5 g, 2.32 mmol), acetonitrile (3 mL), potassium carbonate (0.48 g, 3.48 mmol) and iodoethane (0.36 g, 2.32 mmol) was heated under microwave irradiation at 120° C. for 20 minutes. Aqueous sodium carbonate (10%, 50 mL) was added and the aqueous phase was extracted with ethyl acetate (2×50 mL). The combined organic phase was dried (Na2SO4) and evaporated. Purification by HPLC on Waters OBD C18, 5 μm (MeOH/33 mM NH3, 20:80 to 50:50) gave the title compound. The amine was converted to the fumaric acid salt and recrystallized from methanol/diethyl ether/diisopropyl ether (0.249 g). M.p. 142-145.5° C.; MS m/z (relative intensity, 70 eV) 243 (M+, 24), 228 (19), 157 (15), 72 (27), 71 (bp).

Example 21

3-(3-CHLORO-4-FLUOROPHENYL)-1-PROPYLPYRROLIDIN-3-OL

Preparation according to Example 22: 3-(3-chloro-4-fluorophenyl)pyrrolidin-3-ol (0.8 g, 3.72 mmol), potassium carbonate (1.03 g, 7.45 mmol), iodopropane (0.83 mg, 4.86 mmol), acetonitrile (20 mL). Purification by flash chromatography on silica gel (ethyl acetate/methanol, 1:1 to 0:1). Yield: 520 mg. The amine was converted to the fumaric acid salt and recrystallized from ethanol/diethyl ether: M.p. 157.9° C.; MS m/z (relative intensity, 70 eV) 257 (M+, 8), 228 (bp), 198 (30), 157 (15), 84 (88).

Example 22

3-(3-CHLORO-5-FLUOROPHENYL)-1-PROPYLPYRROLIDIN-3-OL

A mixture of 3-(3-chloro-5-fluorophenyl)pyrrolidin-3-ol (1.10 g, 5 mmol), acetonitrile (20 mL), potassium carbonate (1.4 g, 10.1 mmol) and iodopropane (1.13 mg, 6.65 mmol) was stirred at ambient temperature for 2 h. The temperature was shortly raised to 40° C. twice during this period. Water was added and the aqueous phase was extracted with ethyl acetate, the combined organic phase was dried (MgSO4), and evaporated. Purification by flash chromatography on silica gel (ethyl acetate/methanol, 1:0 to 1:1) gave the title compound (0.57 g). The amine was converted to the oxalic acid salt and recrystallized from ethanol/diisopropyl ether: M.p. 157.2° C.; MS m/z (relative intensity, 70 eV) 257 (M+, 8), 228 (bp), 198 (46), 129 (36), 84 (59).

Example 23

3-(2,3-DIFLUOROPHENYL)-3-FLUOROPYRROLIDINE

To a solution of 1-benzyl-3-(2,3-difluorophenyl)-3-fluoropyrrolidine (1.6 g, 5.5 mmol) in dry 1,2-dichloroethane (10 mL) under nitrogen was added 1-chloroethylchloroformate (600 μl, 5.5 mmol). The mixture was stirred at ambient temperature for 7 h after which methanol was added and the mixture was evaporated. Methanol (10 mL) was added and the mixture was heated at reflux for 4 h. The mixture was evaporated and purified by column chromatography on silica gel (ethyl acetate/methanol, 1:0 to 1:1) to give the title compound (214 mg). The amine was converted to the hydrochloric acid salt and recrystallized from ethanol/diethyl ether: M.p. 136° C.; MS m/z (relative intensity, 70 eV) 201 (M+, 35), 151 (bp), 158 (69), 138 (45), 133 (42).

Example 24

(+)-3-(3,4-DIFLUOROPHENYL)-1-ETHYLPYRROLIDIN-3-OL

In a sealed tube a mixture of enantiomer E1 of 3-(3,4-difluorophenyl)pyrrolidin-3-ol (0.26 g, 1.3 mmol), acetonitrile (3 mL), potassium carbonate (0.269 g, 1.95 mmol) and iodoethane (0.20 g, 1.3 mmol) was heated under microwave irradiation at 80° C. for 25 minutes. Aqueous sodium carbonate (10%, 50 mL) was added and the aqueous phase was extracted with ethyl acetate (2×50 mL), the combined organic phase was washed with brine, dried (Na2SO4) and evaporated. Purification by HPLC on Waters OBD C18, 5 μm (MeOH/33 mM NH3, 35:65 to 50:50) gave the title compound (0.117 g). $[\alpha]_D$=+19.4° (methanol). The amine was converted to the fumaric acid salt and recrystallized from methanol/diethyl ether/diisopropyl ether: M.p. 136-137° C.; MS m/z (relative intensity, 70 eV) 227 (M+, 10), 207, (19), 141 (20), 72 (42), 71 (bp).

Example 25

(−)-3-(3,4-DIFLUOROPHENYL)-1-ETHYLPYRROLIDIN-3-OL

Preparation according to Example 24: Enantiomer E2 of 3-(3,4-difluorophenyl)-pyrrolidin-3-ol (0.27 g, 1.35 mmol), acetonitrile (3 mL), potassium carbonate (0.279 g, 2.02 mmol) and iodoethane (0.21 g, 1.35 mmol). Purification by HPLC on Waters OBD C18, 5 μm (MeOH/33 mM NH3, 35:65 to 50:50). Yield 0.14 g. $[\alpha]_D$=−18.8° (methanol). The amine was converted to the fumaric acid salt and recrystallized from methanol/diethyl ether/diisopropyl ether: M.p. 136-137° C.; MS m/z (relative intensity, 70 eV) 227 (M+, 11), 141, (20), 113 (17), 72 (43), 71 (bp).

Example 26

3-(3-CHLORO-5-FLUOROPHENYL)-1-METHYLPYRROLIDIN-3-OL

A mixture of 3-(3-chloro-5-fluorophenyl)pyrrolidin-3-ol (0.4 g, 1.85 mmol) in formic acid (5.4 mL) and aqueous formaldehyde (40%, 4.8 mL) was heated at 85° C. for 2.5 h. Aqueous sodium carbonate (10%, 50 mL) was added and the aqueous phase was extracted with ethyl acetate (2×70 mL), the combined organic phase was dried (MgSO4) and evaporated. Purification by HPLC on Waters OBD C18, 5 μm (MeOH/33 mM NH3, 20:80 to 100:0) gave the title compound (0.131 g). The amine was converted to the fumaric acid salt and recrystallized from methanol/diethyl ether/diisopropyl ether: M.p. 129-131° C.; MS m/z (relative intensity, 70 eV) 229 (M+, 7), 157 (5), 129 (6), 58 (30), 57 (bp).

Example 27

(+)-3-(3,4-DIFLUOROPHENYL)-1-PROPYLPYRROLIDIN-3-OL

Preparation according to Example 24: Enantiomer E1 of 3-(3,4-difluorophenyl)-pyrrolidin-3-ol (0.26 g, 1.3 mmol), acetonitrile (3 mL), potassium carbonate (0.269 g, 1.95 mmol) and iodopropane (0.22 g, 1.3 mmol). Purification by HPLC on Waters OBD C18, 5 μm (MeOH/33 mM NH3, 45:55 to 60:40). Yield: 0.156 g. $[\alpha]_D$=+19.0° (methanol). The amine was converted to the fumaric acid salt and recrystallized from methanol/diethyl ether/diisopropyl ether: M.p. 127-129° C.; MS m/z (relative intensity, 70 eV) 241 (M+, 9), 212, (bp), 182 (32), 141 (17), 84 (58).

Example 28

(−)-3-(3,4-DIFLUOROPHENYL)-1-PROPYLPYRROLIDIN-3-OL

Preparation according to Example 24: Enantiomer E2 of 3-(3,4-difluorophenyl)-pyrrolidin-3-ol (0.27 g, 1.35 mmol), acetonitrile (3 mL), potassium carbonate (0.279 g, 2.02 mmol) and iodopropane (137 μl, 1.35 mmol). Purification by HPLC on Waters OBD C18, 5 μm (MeOH/33 mM NH3, 45:55 to 60:40). Yield: 0.125 g. $[\alpha]_D$=−21.1° (methanol). The amine was converted to the fumaric acid salt and recrystallized from methanol/diethyl ether/diisopropyl ether: M.p. 128-129° C.; MS m/z (relative intensity, 70 eV) 241 (M+, 9), 212, (bp), 182 (32), 141 (17), 84 (62).

Example 29

(+)-3-(3,5-DIFLUOROPHENYL)-1-PROPYLPYRROLIDIN-3-OL

Preparation according to Example 24: Enantiomer E1 of 3-(3,5-difluorophenyl)-pyrrolidin-3-ol (0.53 g, 2.66 mmol), acetonitrile (3 mL), potassium carbonate (0.55 g, 3.99 mmol) and iodopropane (260 μl, 2.66 mmol). Purification by HPLC on Waters OBD 018, 5 μm (MeOH/33 mM NH3, 40:60 to 60:40). Yield: 0.274 g. $[\alpha]_D$=+21.2° (methanol). The amine was converted to the oxalic acid salt and recrystallized from methanol/diethyl ether: M.p. 117-118° C.; MS m/z (relative intensity, 70 eV) 241 (M+, 8), 212, (bp), 182 (35), 127 (12), 84 (45).

Example 30

(−)-3-(3,5-DIFLUOROPHENYL)-1-PROPYLPYRROLIDIN-3-OL

Preparation according to Example 24: Enantiomer E2 of 3-(3,5-difluorophenyl)-pyrrolidin-3-ol (0.53 g, 2.66 mmol), acetonitrile (3 mL), potassium carbonate (0.55 g, 3.99 mmol) and iodopropane (260 μl, 2.66 mmol). Purification by HPLC on Waters OBD C18, 5 μm (MeOH/33 mM NH3, 40:60 to 60:40). Yield: 0.295 g. $[\alpha]_D$=−22.7° (methanol). The amine was converted to the oxalic acid salt and recrystallized from methanol/diethyl ether: M.p. 118-119° C.; MS m/z (relative intensity, 70 eV) 241 (M+, 9), 213, (12), 212 (bp), 182 (32), 84 (36).

Example 31

(−)-3-(3-CHLORO-5-FLUOROPHENYL)-1-ETHYLPYRROLIDIN-3-OL

A mixture of (−)-1-benzyl-3-(3-chloro-5-fluorophenyl)pyrrolidin-3-ol (0.66 g, 2.16 mmol) and iodoethane (4 mL, 50.2 mmol) was refluxed for 4 h. The mixture was evaporated and tert-butyl methyl ether (20 mL) was added. The solvent was decantated off, morpholine (5 mL) was added and the mixture was heated under microwave irradiation at 120° C. for 30 minutes. The mixture was evaporated and purified twice by flash chromatography on silica gel (methanol/ethyl acetate, 7:3 to 3:7 and isocratic 1:1) to give the title compound (0.26 g). $[\alpha]_D$=−21.4° (methanol). The amine was converted to the oxalic acid salt and recrystallized from ethanol/diethyl ether/diisopropyl ether: M.p. 117-118° C.; MS m/z (relative intensity, 70 eV) 243 (M+, 23), 157, (78), 130 (82), 129 (95), 71 (bp).

Example 32

(−)-3-(2,3-DIFLUOROPHENYL)-1-ETHYLPYRROLIDIN-3-OL

In a sealed tube a mixture of (−)-1-benzyl-3-(2,3-difluorophenyl-3-ol-pyrrolidin (0.3 g, 1.04 mmol) and iodoethane (3 mL, 30.6 mmol) was heated under microwave irradiation at 70° C. for 4 h. The resulting mixture was evaporated, morpholine (2 mL) and acetonitrile (2 mL) was added and the mixture was heated under microwave irradiation at 130° C. for 30 minutes. The mixture was evaporated and purified by HPLC on Waters OBD 018, 5 μm (MeOH/33 mM NH3, 20:80 to 45:55) to give the title compound: $[\alpha]_D$=−18.7° (methanol). The amine was converted to the oxalic acid salt and

Example 33

(−)-3-(2,3-DIFLUOROPHENYL)-1-PROPYLPYR-ROLIDIN-3-OL

Preparation according to Example 34: (−)-1-benzyl-3-(2, 3-difluorophenyl)pyrrolidin-3-ol (0.40 g, 1.38 mmol), dimethyl formamide (3 mL), iodopropane (1.35 mL, 13.8 mmol) and morpholine (2 mL). Purification by HPLC on Waters OBD C18, 5 μm (MeOH/33 mM NH3, 40:60 to 60:40). Yield: 0.174 g. $[\alpha]_D$=−22.1° (methanol). The amine was converted to the fumaric acid salt and recrystallized from methanol/diethyl ether/diisopropyl ether: M.p. 97-100° C.; MS m/z (relative intensity, 70 eV) 241 (M+, 10), 212, (bp), 182 (34), 84 (53), 57 (14).

Example 34

(+)-3-(2,3-DIFLUOROPHENYL)-1-PROPYLPYR-ROLIDIN-3-OL

In a sealed tube a mixture of (+)-1-benzyl-3-(2,3-difluorophenyl)pyrrolidin-3-ol (0.40 g, 1.38 mmol), dimethyl formamide (3 mL) and iodopropane (1.35 mL, 13.8 mmol) was heated under microwave irradiation at 80° C. for 45 minutes. The resulting mixture was evaporated, morpholine (2 mL) was added and the mixture was heated under micro-wave irradiation at 130° C. for 30 minutes. Aqueous sodium carbonate (10%, 50 mL) was added and the aqueous phase was extracted with ethyl acetate (2×50 mL), the combined organic phase was washed with aqueous LiCl (5%, 50 mL), dried (Na2SO4) and evaporated. Purification by HPLC on Waters OBD C18, 5 μm (MeOH/33 mM NH3, 40:60 to 60:40) gave the title compound (0.115 g). $[\alpha]_D$=+22.8° (methanol). The amine was converted to the fumaric acid salt and recrystallized from methanol/diethyl ether/diisopropyl ether: M.p. 95-98° C.; MS m/z (relative intensity, 70 eV) 241 (M+, 8), 212, (bp), 182 (41), 84 (88), 57 (24).

Example 35

(+)-3-(3-CHLORO-2-FLUOROPHENYL)-1-ETH-YLPYRROLIDIN-3-OL

In a sealed tube a mixture of (+)-1-benzyl-3-(3-chloro-2-fluorophenyl)pyrrolidin-3-ol (0.31 g, 1.01 mmol), dimethyl formamide (3 mL) and iodoethane (0.16 mL, 2.02 mmol) was heated under microwave irradiation at 80° C. for 2×15 minutes. The resulting mixture was evaporated, morpholine (2 mL) was added and the mixture was heated under microwave irradiation at 130° C. for 30 minutes. Aqueous LiCl (5%, 50 mL) was added and the aqueous phase was extracted with ethyl acetate (2×50 mL, dried (Na2SO4) and evaporated. Purification by flash chromatography on silica gel (ethyl acetate/methanol, 1:0 to 1:1) gave the title compound (0.131 g). $[\alpha]_D$=+27.2° (methanol). The amine was converted to the oxalic acid salt and recrystallized from methanol/diethyl ether/diisopropyl ether: M.p. 71-74° C.; MS m/z (relative intensity, 70 eV) 243 (M+, 13), 228, (10), 157 (12), 72 (26), 71 (bp).

Example 36

(+)-3-(2,3-DIFLUOROPHENYL)-1-ETHYLPYR-ROLIDIN-3-OL

Preparation according to Example 34: (+)-1-benzyl-3-(2, 3-difluorophenyl)pyrrolidin-3-ol (0.40 g, 1.38 mmol), dimethyl formamide (3 mL), iodoethane (1.1 mL, 13.8 mmol) and morpholine (2 mL). Purification by HPLC on Waters OBD C18, 5 μm (MeOH/33 mM NH3, 20:80 to 45:55). Yield: 0.11 g. $[\alpha]_D$=+19.8° (methanol). The amine was converted to the fumaric acid salt and recrystallized from methanol/diethyl ether/diisopropyl ether: M.p. 118-120° C.; MS m/z (relative intensity, 70 eV) 228 (M+, 14), 141, (16), 127 (14), 72 (26), 71 (bp).

Example 37

(−)-3-(3-CHLORO-2-FLUOROPHENYL)-1-ETH-YLPYRROLIDIN-3-OL

In a sealed tube a mixture of (−)-1-benzyl-3-(2-fluor-3-chlorophenyl-3-ol-pyrrolidin (0.31 g, 1.01 mmol), dimethyl formamide (3 mL) and iodoethane (1.35 mL, 13.8 mmol) was heated under microwave irradiation at 80° C. for 45 minutes. The resulting mixture was evaporated, morpholine (2 mL) was added and the mixture was heated under micro-wave irradiation at 130° C. for 30 minutes. Aqueous LiCl (5%, 50 mL) was added and the aqueous phase was extracted with ethyl acetate (2×50 mL, dried (Na2SO4) and evaporated. Purification by flash chromatography on silica gel (ethyl acetate/methanol, 1:0 to 1:1) gave the title compound (0.128 g). $[\alpha]_D$=−27.8° (methanol). The amine was converted to the oxalic acid salt and recrystallized from methanol/diethyl ether/diisopropyl ether: M.p. 72-74° C.; MS m/z (relative intensity, 70 eV) 243 (M+, 11), 228, (9), 157 (12), 72 (27), 71 (bp).

Example 38

(−)-1-BUTYL-3-(2,3-DIFLUOROPHENYL)PYR-ROLIDIN-3-OL

In a sealed tube a mixture of enantiomer E2 of 3-(2,3-difluorophenyl)pyrrolidin-3-ol (0.5 g, 2.5 mmol), acetonitrile (20 mL), potassium carbonate (0.69 g, 5 mmol) and n-butyl-bromide (0.25 mL, 2.6 mmol) was stirred at ambient temperature for 30 min after which an additional amount of n-butyl-bromide (0.12 mL, 1.25 mmol) was added and the mixture was stirred for 1 h. Water was added and the aqueous phase was extracted with ethyl acetate. The combined organic phase was dried (Na2SO4) and evaporated. Purification by flash chromatography on silica gel (ethyl acetate/methanol, 1:1) gave the title compound (0.35 g). $[\alpha]_D$=−26° (methanol). The amine was converted to the oxalic acid salt and recrystallized from ethanol/diethyl ether: M.p. 155.3° C.; MS m/z (relative intensity, 70 eV) 255 (M+, 8), 182 (30), 98 (25), 57 (16), 212 (bp).

Example 39

(−)-3-(2,3-DIFLUOROPHENYL)-1-ISOBU-TYLPYRROLIDIN-3-OL

Preparation according to Example 38: Enantiomer E2 of 3-(2,3-difluorophenyl)pyrrolidin-3-ol (0.5 g, 2.5 mmol), acetonitrile (20 mL), potassium carbonate (0.69 g, 5 mmol), 1-bromo-2-methylpropane (0.32 mL, 2.97 mmol). Stirred 4 h. Purification by flash chromatography on silica gel (ethyl acetate/methanol, 2:1). Yield: 0.16 g. [α]$_D$=−16.1° (methanol). The amine was converted to the oxalic acid salt and recrystallized from ethanol/diethyl ether: M.p. 176° C.; MS m/z (relative intensity, 70 eV) 255 (M+3), 182 (45), 213 (12), 127 (6) 212 (bp).

Example 40

(−)-3-(2,3-DIFLUOROPHENYL)-1-METHYLPYR-ROLIDIN-3-OL

Preparation according to Example 11: Enantiomer E2 of 3-(2,3-difluorophenyl)pyrrolidin-3-ol (0.5 g, 2.5 mmol) in formic acid (7.2 mL) and aqueous formaldehyde (40%, 6.5 mL). 65° C. for 5 h. Water was added (50 mL), and the mixture was washed with diethyl ether. The water phase was basified with NaOH (5 M), extracted with ethyl acetate, dried (MgSO4) and evaporated. The crude compound was again treated with the same amount of formic acid and aqueous formaldehyde as above for 5 h. Purification by flash chromatography on silica gel (ethyl acetate/methanol, 4:1 to 2:1). Yield: 0.7 g. [α]$_D$=−21.5° (methanol). The amine was converted to the oxalic acid salt and recrystallized from ethanol/diethyl ether: M.p. 134.3° C.; MS m/z (relative intensity, 70 eV) 213 (M+, 20), 58 (27), 141 (16), 127 (11), 57 (bp).

Example 41

(−)-1-ALLYL-3-(2,3-DIFLUOROPHENYL)PYR-ROLIDIN-3-OL

Preparation according to Example 8: Enantiomer E2 of 3-(2,3-difluorophenyl)pyrrolidin-3-ol (0.5 g, 2.5 mmol), acetonitrile (20 mL), potassium carbonate (0.69 g, 5 mmol) and 3-bromo-1-propene (0.23 mL, 2.78 mmol). Refluxed for 2 h. Purification by flash chromatography on silica gel (ethyl acetate/methanol, 5:1). Yield: 0.33 g. [α]$_D$=−26.6° (methanol). The amine was converted to the oxalic acid salt and recrystallized from methanol/diisopropyl ether: M.p. 120° C.; MS m/z (relative intensity, 70 eV) (239 (M+, 25), 198 (48), 141 (35), 127 (23), 83 (bp).

Example 42

(−)-3-(2,3-DIFLUOROPHENYL)-1-(2-METHOXY-ETHYL)PYRROLIDIN-3-OL

Preparation according to Example 43: Enantiomer E2 of 3-(2,3-difluorophenyl)-pyrrolidin-3-ol (0.5 g, 2.5 mmol), acetonitrile (20 mL), potassium carbonate (0.69 g, 5 mmol), 1-bromo-2-methoxyethane (0.255 mL, 2.7 mmol). Stirred 1 h at ambient temperature. Addition of 1-bromo-2-methoxyethane (0.05 mL, 0.53 mmol), stirred at 40° C. for 2 min. Purification by flash chromatography on silica gel (ethyl acetate/methanol, 4:1). Yield: 0.32 g. [α]$_D$=−20.8° (methanol). The amine was converted to the oxalic acid salt and recrystallized from methanol/diisopropyl ether: M.p. 146.7° C.; MS m/z (relative intensity, 70 eV) 257 (M+, 2), 212 (bp), 182 (56), 141 (9), 127 (12).

Example 43

(−)-1-BUTYL-3-(3,5-DIFLUOROPHENYL)PYR-ROLIDIN-3-OL

In a sealed tube a mixture of enantiomer E2 of 3-(3,5-difluorophenyl)pyrrolidin-3-ol (0.29 g, 1.45 mmol), acetonitrile (15 mL), potassium carbonate (0.4 g, 2.9 mmol) and n-butylbromide (0.15 mL, 1.59 mmol) was stirred at ambient temperature for 5 h and then at 60° C. for 2 h. Aqueous sodium carbonate (10%, 5 mL) was added and the aqueous phase was extracted with ethyl acetate (2×50 mL). The combined organic phase was dried (Na2SO4) and evaporated. Purification by flash chromatography on silica gel (ethyl acetate/methanol, 7:1) gave the title compound (0.175 g). [α]$_D$=−19.8° (methanol). The amine was converted to the oxalic acid salt and recrystallized from methanol/diisopropyl ether: M.p. 146-147° C.; MS m/z (relative intensity, 70 eV) 255 (M+, 6), 212 (bp), 98 (46), 182 (35), 57 (29), 127 (13).

Example 44

(−)-1-ALLYL-3-(3,5-DIFLUOROPHENYL)PYR-ROLIDIN-3-OL

In a sealed tube a mixture of enantiomer E2 of 3-(3,5-difluorophenyl)pyrrolidin-3-ol (0.29 g, 1.45 mmol), acetonitrile (15 mL), potassium carbonate (0.4 g, 2.9 mmol) and allylbromide (0.13 mL, 1.59 mmol) was heated at 60° C. for 2 h. Aqueous sodium carbonate (10%, 5 mL) was added and the aqueous phase was extracted with ethyl acetate (2×50 mL). The combined organic phase was dried (Na2SO4) and evaporated. Purification by flash chromatography on silica gel (ethyl acetate/methanol, 7:1) gave the title compound (0.08 g). [α]$_D$=−20.3° (methanol). The amine was converted to the oxalic acid salt and recrystallized from ethanol/diisopropyl ether: M.p. 102-103° C.; MS m/z (relative intensity, 70 eV) 239 (M+, 22), 83 (bp), 198 (52), 82 (33), 84 (29), 113 (27).

Example 45

(−)-3-(3,5-DIFLUOROPHENYL)-1-(2-METHOXY-ETHYL)PYRROLIDIN-3-OL

In a sealed tube a mixture of enantiomer E2 of 3-(3,5-difluorophenyl)pyrrolidin-3-ol (0.29 g, 1.45 mmol), acetonitrile (15 mL), potassium carbonate (0.4 g, 2.9 mmol) and 2-bromoethylmethyleter (0.145 mL, 1.55 mmol) was stirred at ambient temperature for 4 h. and then at 80° C. for 1 h. Aqueous sodium carbonate (10%, 5 mL) was added and the aqueous phase was extracted with ethyl acetate (2×50 mL). The combined organic phase was dried (Na2SO4) and evaporated. Purification by flash chromatography on silica gel (ethyl acetate/methanol, 10:1) gave the title compound (0.157 g). [α]$_D$=−18.9° (methanol). The amine was converted to the oxalic acid salt and recrystallized from ethanol/diisopropyl ether: M.p. 130-131° C.; MS m/z (relative intensity, 70 eV) 257 (M+, 2), 212 (bp), 182 (52), 127 (12), 213 (12), 58 (8).

Example 46

(−)-3-(3,5-DIFLUOROPHENYL)-1-ISOBU-TYLPYRROLIDIN-3-OL

In a sealed tube a mixture of enantiomer E2 of 3-(3,5-difluorophenyl)pyrrolidin-3-ol (0.28 g, 1.45 mmol), acetonitrile (15 mL), potassium carbonate (0.4 g, 2.9 mmol) and 1-bromo-2-methylpropane (0.15 mL, 1.59 mmol) was stirred at ambient temperature for 5 h and then at 60° C. for 2 h. Aqueous sodium carbonate (10%, 5 mL) was added and the aqueous phase was extracted with ethyl acetate (2×50 mL). The combined organic phase was dried (Na2SO4) and evaporated. Purification by flash chromatography on silica gel (ethyl acetate/methanol, 10:1) gave the title compound (0.193 g). $[\alpha]_D$=−22.9° (methanol). The amine was converted to the oxalic acid salt and recrystallized from ethanol/diisopropyl ether: M.p. 162-163° C.; MS m/z (relative intensity, 70 eV) 255 (M+, 2), 212 (bp), 182 (46), 213 (13), 57 (10), 127 (10).

Example 47

(−)-3-(3,5-DIFLUOROPHENYL)-1-METHYLPYRROLIDIN-3-OL

Preparation according to Example 11: Enantiomer E2 of 3-(3,5-difluorophenyl)-pyrrolidin-3-ol (0.29 g, 1.45 mmol), formic acid (3.8 mL), aqueous formaldehyde (40%, 3.4 mL). 65° C. for 5 h. Purification by flash chromatography on silica gel (ethyl acetate/methanol, 10:1). Yield: 0.19 g. $[\alpha]_D$=−22.8° (methanol). The amine was converted to the oxalic acid salt and recrystallized from ethanol/diethyl ether/diisopropyl ether: M.p. 134-135° C.; MS m/z (relative intensity, 70 eV) 213 (M+, 15), 57.1 (bp), 58.1 (31), 113 (13), 127 (11), 141 (11).

Example 48

(−)-3-(2,3-DIFLUOROPHENYL)-1-(3,3,3-TRIFLUOROPROPYL)PYRROLIDIN-3-OL

Preparation according to Example 43: Enantiomer E2 of 3-(2,3-difluorophenyl)-pyrrolidin-3-ol (0.5 g, 2.5 mmol), acetonitrile (20 mL), potassium carbonate (0.69 g, 5 mmol), 1,1,1-trifluoro-3-iodopropane (0.32 mL, 3.1 mmol). Stirred 2 h at ambient temperature and 2×5 min at 40° C.; Purification by flash chromatography on silica gel (ethyl acetate/methanol, 4:1) Yield: 0.2 g. $[\alpha]_D$=−14.6° (methanol). The amine was converted to the oxalic acid salt and recrystallized from ethanol/diethyl ether: M.p. 144° C.; MS m/z (relative intensity, 70 eV) 295 (M+, 24), 212 (31), 182 (12), 139 (bp), 127 (20).

Example 49

(−)-1-(CYCLOPROPYLMETHYL)-3-(2,3-DIFLUOROPHENYL)PYRROLIDIN-3-OL

Preparation according to Example 43: Enantiomer E2 of 3-(2,3-difluorophenyl)-pyrrolidin-3-ol (0.58 g, 2.9 mmol), acetonitrile (20 mL), potassium carbonate (0.69 g, 5 mmol), cyclopropylmethyl bromide (0.308 mL, 3.18 mmol). Stirred 2 h at ambient temperature and 2×5 min at 40° C.; Purification by flash chromatography on silica gel (ethyl acetate/methanol, 4:1) Yield: 0.28 g. $[\alpha]_D$=−14.3° (methanol). The amine was converted to the oxalic acid salt and recrystallized from ethanol/diethyl ether: M.p. 172.8° C.; MS m/z (relative intensity, 70 eV) 253 (M+, 4) 55 (50), 141 (18), 127 (14), 96 (bp).

Example 50

3-(3,4-DIFLUOROPHENYL)-1-ISOPROPYLPYRROLIDIN-3-OL

In a sealed tube a mixture of 3-(3,4-difluorophenyl)pyrrolidin-3-ol (0.192 g, 0.963 mmol), acetonitrile (3 mL), potassium carbonate (0.133 g, 0.963 mmol) and isopropylbromide (0.118 g, 0.963 mmol) was heated under microwave irradiation at 120° C. for 25 minutes. The mixture was filtrated and evaporated. Purification by flash chromatography on silica gel (ethyl acetate/methanol, 4:1 to 1:1) and by HPLC on Waters OBD C18, 5 μm (MeOH/33 mM NH3, 20:80 to 55:45) gave the title compound (0.092 g). The amine was converted to the fumaric acid salt and recrystallized from ethanol/diethyl ether/diisopropyl ether: M.p. 143-147° C.; MS m/z (relative intensity, 70 eV) 241 (M+, 11), 226 (bp), 182 (46), 85 (53), 84 (31).

Example 51

(+)-1-BUTYL-3-(3,5-DIFLUOROPHENYL)PYRROLIDIN-3-OL

In a sealed tube a mixture of enantiomer E1 of 3-(3,5-difluorophenyl)pyrrolidin-3-ol (0.18 g, 0.92 mmol), acetonitrile (5 mL), potassium carbonate (0.25 g, 1.84 mmol) and n-butylbromide (0.1 mL, 1.01 mmol) was heated under microwave irradiation at 120° C. for 45 min. Aqueous sodium carbonate (10%, 5 mL) was added and the aqueous phase was extracted with ethyl acetate (2×50 mL), the combined organic phase was dried (Na2SO4) and evaporated. Purification on a Biotage Isolute SCX-3 SPE column (washed with methanol and eluted with methanol/triethylamine, 4:1) and by flash chromatography on silica gel (ethyl acetate/methanol, 7:1) gave the title compound (0.13 g). $[\alpha]_D$=+21.9° (methanol). The amine was converted to the oxalic acid salt and recrystallized from methanol/diisopropyl ether: M.p. 146-147° C.; MS m/z (relative intensity, 70 eV) 255 (M+, 5), 212 (bp), 98 (66), 57 (51), 182 (39), 127 (18).

Example 52

(+)-3-(3,5-DIFLUOROPHENYL)-1-METHYLPYRROLIDIN-3-OL

Preparation according to Example 11: Enantiomer E1 of 3-(3,5-difluorophenyl)-pyrrolidin-3-ol (0.18 g, 0.92 mmol), formic acid (2.6 mL), aqueous formaldehyde (40%, 2.45 mL). Purification on a Biotage Isolute SCX-3 SPE column (washed with methanol and eluted with methanol/triethylamine, 4:1) and by flash chromatography on silica gel (ethyl acetate/methanol, 10:1). Yield: 0.125 g. $[\alpha]_D$=+19.8° (methanol). The amine was converted to the oxalic acid salt and recrystallized from ethanol/diethyl ether/diisopropyl ether: M.p. 150° C.; MS m/z (relative intensity, 70 eV) 213 (M+, 14), 57 (bp), 58 (31), 113 (13), 127 (11), 141 (10).

Example 53

(+)-3-(3,5-DIFLUOROPHENYL)-1-ISOBUTYLPYRROLIDIN-3-OL

Preparation according to Example 51. Enantiomer E1 of 3-(3,5-difluorophenyl)-pyrrolidin-3-ol (0.18 g, 0.92 mmol), acetonitrile (6 mL), potassium carbonate (0.25 g, 1.84 mmol), 1-bromo-2-methylpropane (0.1 mL, 0.92 mmol). Flash chromatography on silica gel (ethyl acetate/methanol, 9:1). Yield: 0.18 g. $[\alpha]_D$=+22.6° (methanol). The amine was converted to the oxalic acid salt and recrystallized from methanol/diisopropyl ether: M.p. 164-165° C.; MS m/z (relative intensity, 70 eV) 255 (M+, 2), 212 (bp), 182 (46), 213 (12), 127 (8), 98 (6) 1-bromo-2-methylpropane.

Example 54

(+)-3-(3,5-DIFLUOROPHENYL)-1-(2-METHOXYETHYL)PYRROLIDIN-3-OL

Preparation according to Example 51: Enantiomer E1 of 3-(3,5-difluorophenyl)-pyrrolidin-3-ol (0.18 g, 0.92 mmol), acetonitrile (6 mL), potassium carbonate (0.25 g, 1.84 mmol) and 2-bromo ethyl methyl eter (0.09 mL, 0.92 mmol). Flash chromatography on silica gel (ethyl acetate/methanol, 10:1). Yield: 0.118 g. $[\alpha]_D$=+22.3° (methanol). The amine was converted to the oxalic acid salt and recrystallized from methanol/diisopropyl ether: M.p. 131-132° C.; MS m/z (relative intensity, 70 eV) 257 (M+, 2), 212 (bp), 182 (52), 213 (13), 127 (13), 58 (9).

Example 55

(+)-1-ALLYL-3-(3,5-DIFLUOROPHENYL)PYRROLIDIN-3-OL

Preparation according to Example 51: Enantiomer E1 of 3-(3,5-difluorophenyl)-pyrrolidin-3-ol (0.18 g, 0.92 mmol), acetonitrile (6 mL), potassium carbonate (0.25 g, 1.84 mmol) and allyl bromide (0.077 mL, 0.92 mmol). Flash chromatography on silica gel (ethyl acetate/methanol, 10:1). Yield: 0.1 g. $[\alpha]_D$=+22.4° (methanol). The amine was converted to the oxalic acid salt and recrystallized from methanol/diisopropyl ether: M.p. 104-105° C.; MS m/z (relative intensity, 70 eV) 239 (M+, 40), 83 (bp), 198 (84), 82 (13), 14 (33), 127 (31).

Example 56

(+)-3-(3-CHLORO-2-FLUOROPHENYL)-1-METHYLPYRROLIDIN-3-OL

Preparation according to Example 34: (+)-1-benzyl-3-(3-chloro-2-fluorophenyl)-pyrrolidin-3-ol (0.93 g, 3.05 mmol) and iodomethane (1 mL, 15.9 mmol), dimethyl formamid (3 mL), morpholine (2 mL). Purification by flash chromatography on silica gel (ethyl acetate/methanol, 1:0 to 1:1). Yield: 0.289 g. $[\alpha]_D$=+25.9° (methanol). The amine was converted to the oxalic acid salt and recrystallized from methanol/diethyl ether/diisopropyl ether: M.p. 123-125° C.; MS m/z (relative intensity, 70 eV) 229 (M+, 7), 157 (8), 129 (6), 58 (29), 57 (bp).

Example 57

(−)-3-(3-CHLORO-2-FLUOROPHENYL)-1-METHYLPYRROLIDIN-3-OL

Preparation according to Example 34: (−)-1-benzyl-3-(3-chloro-2-fluorophenyl)pyrrolidin-3-ol (0.748 g, 2.45 mmol), iodomethane (1 mL, 15.9 mmol), dimethyl formamid (3 mL), morpholine (2 mL). Purification by flash chromatography on silica gel (ethyl acetate/methanol, 1:0 to 1:1). Yield: 0.193 g. $[\alpha]_D$=−25.7° (methanol). The amine was converted to the oxalic acid salt and recrystallized from methanol/diethyl ether/diisopropyl ether: M.p. 123-125° C.; MS m/z (relative intensity, 70 eV) 229 (M+, 14), 157 (11), 129 (7), 58 (27), 57 (bp).

Example 58

(+)-1-BUTYL-3-(2,3-DIFLUOROPHENYL)PYRROLIDIN-3-OL

Preparation according to Example 51. Enantiomer E1 of 3-(2,3-difluorophenyl)-pyrrolidin-3-ol (0.15 g, 0.77 mmol), acetonitrile (6 mL), potassium carbonate (0.21 g, 1.55 mmol), n-butylbromid (0.08 mL, 0.77). Flash chromatography on silica gel (Ethyl acetate/methanol, 7:1). Yield: 0.085 g. $[\alpha]_D$=+24.8°; The amine was converted to the oxalic acid salt and recrystallized from ethanol/diisopropyl ether; M.p. 157-158° C.; MS m/z (relative intensity, 70 eV) 255 (M+, 7), 212 (bp), 98 (52), 57 (40), 182 (37), 127 (16).

Example 59

(+)-3-(2,3-DIFLUOROPHENYL)-1-METHYLPYRROLIDIN-3-OL

Preparation according to Example 11: Enantiomer E1 of 3-(2,3-difluorophenyl)-pyrrolidin-3-ol (0.15 g, 0.72 mmol), formic acid (1.95 mL), aqueous formaldehyde (40%, 2.17 mL). The mixture was stirred for 5 h after which additional aqueous formaldehyde (1.5 mL) was added and the mixture was refluxed overnight. Purification by flash chromatography on silica gel (ethyl acetate/methanol, 10:1). Yield: 0.09 g. $[\alpha]_D$=+19.1°; The amine was converted to the oxalic acid salt and recrystallized from ethanol/diethyl ether/diisopropyl ether; M.p. 131-132° C.; MS m/z (relative intensity, 70 eV) 213 (M+, 15), 57 (bp), 58 (28), 141 (15), 127 (10), 113 (10).

Example 60

(+)-3-(2,3-DIFLUOROPHENYL)-1-(2-METHOXYETHYL)PYRROLIDIN-3-OL

Preparation according to Example 51: Enantiomer E1 of 3-(2,3-difluorophenyl)-pyrrolidin-3-ol (0.15 g, 0.75 mmol), acetonitrile (6 mL), potassium carbonate (0.208 g, 1.5 mmol) and 1-bromo-2-methoxyethane (0.07 mL, 0.75 mmol). Flash chromate-graphy on silica gel (Ethyl acetate/methanol, 10:1). Yield: 0.07 g. $[\alpha]_D$=+22.5°; The amine was converted to the oxalic acid salt and recrystallized from ethanol/diethyl ether/ diisopropyl ether; M.p. 149-150° C.; MS m/z (relative intensity, 70 eV) 257 (M+, 1), 212 (bp), 182 (65), 127 (22), 141 (16), 213 (12).

Example 61

(+)-3-(2,3-DIFLUOROPHENYL)-1-ISOBUTYLPYRROLIDIN-3-OL

Preparation according to Example 51. Enantiomer E1 of 3-(2,3-difluorophenyl)-pyrrolidin-3-ol (0.15 g, 0.75 mmol), acetonitrile (6 mL), potassium carbonate (0.208 g, 1.5 mmol) 1-bromo-2-methylpropane (0.08 mL, 0.75 mmol). Flash chromatography on silica gel (Ethyl acetate/methanol, 9:1). Yield: 0.09 g. $[\alpha]_D$=+17.9°; The amine was converted to the oxalic acid salt and recrystallized from ethanol/diethyl ether/ diisopropyl ether; M.p. 168-169° C.; MS m/z (relative intensity, 70 eV) 255 (M+, 2), 212 (bp), 182 (56), 127 (15), 141 (12), 213 (12).

Example 62

(+)-1-ALLYL-3-(2,3-DIFLUOROPHENYL)PYRROLIDIN-3-OL

Preparation according to Example 51. Enantiomer E1 of 3-(2,3-difluorophenyl)-pyrrolidin-3-ol (0.15 g, 0.75 mmol), acetonitrile (6 mL), potassium carbonate (0.208 g, 1.5 mmol) allyl bromide (0.065 mL, 0.76 mmol). Flash chromatography on silica gel (Ethyl acetate/methanol, 10:1). Yield 0.1 g. $[\alpha]_D$=+23.4°; The amine was converted to the oxalic acid salt and recrystallized from ethanol/diethyl ether/diisopropyl ether; M.p. 119-120° C.; MS m/z (relative intensity, 70 eV) 239 (M+, 13), 83 (bp), 141 (41), 82 (39), 198 (35), 84 (32).

Example 63

(+)-3-(2,3-DIFLUOROPHENYL)-1-(3,3,3-TRIFLUOROPROPYL)PYRROLIDIN-3-OL

Preparation according to Example 51. Enantiomer E1 of 3-(2,3-difluorophenyl)-pyrrolidin-3-ol (0.15 g, 0.75 mmol), acetonitrile (6 mL), potassium carbonate (0.208 g, 1.5 mmol) 1,1,1-trifluoro-3-iodopropane (0.09 mL, 0.76 mmol). Flash chromatography on silica gel (Ethyl acetate/isooctane, 1:1 to 1:2). Yield 0.1 g. $[\alpha]_D$=+16.5°; The amine was converted to the oxalic acid salt and recrystallized from ethanol/diethyl ether/diisopropyl ether; M.p. 144-145° C.; MS m/z (relative intensity, 70 eV) 295 (M+, 12), 139 (bp), 140 (70), 141 (46), 127 (36), 212 (30).

Example 64

(+)-1-(CYCLOPROPYLMETHYL)-3-(2,3-DIFLUOROPHENYL)PYRROLIDIN-3-OL

Preparation according to Example 51. Enantiomer E1 of 3-(2,3-difluorophenyl)-pyrrolidin-3-ol (0.11 g, 0.55 mmol), acetonitrile (6 mL), potassium carbonate (0.140 g, 1 mmol) cyclopropylmethyl bromide (0.05 mL, 0.51 mmol). Flash chromatography on silica gel (Ethyl acetate/methanol, 10:1). Yield: 0.045 g. $[\alpha]_D$=+12.5°; The amine was converted to the oxalic acid salt and recrystallized from ethanol/diethyl ether/diisopropyl ether; Mp. 170-171° C.; MS m/z (relative intensity, 70 eV) 253 (M+, 27), 96 (bp), 97 (60), 55 (44), 141 (32), 98 (2).

Example 65

(−)-3-(3-CHLORO-5-FLUOROPHENYL)-1-METHYLPYRROLIDIN-3-OL

Preparation according to Example 34: (−)-1-benzyl-3-(3-chloro-5-fluorophenyl)pyrrolidin-3-ol (0.115 g, 0.38 mmol) and iodomethane (1 mL, 15.9 mmol), dimethyl formamid (2 mL), morpholine (2 mL). Purification by flash chromatography on silica gel (ethyl acetate/methanol, 1:0 to 1:1). Yield: 0.1 g. $[\alpha]_D$=−21.7° (methanol). The amine was converted to the oxalic acid salt and recrystallized from ethanol/diethyl ether/diisopropyl ether: M.p. 117-118° C.; MS m/z (relative intensity, 70 eV) 229 (M+, 6), 129 (7), 109 (6), 58 (28), 57 (bp).

Example 66

(+)-3-(3-CHLORO-5-FLUOROPHENYL)-1-METHYLPYRROLIDIN-3-OL

Preparation according to Example 34: (+)-1-benzyl-3-(3-chloro-5-fluorophenyl)-pyrrolidin-3-ol (0.1 g, 0.33 mmol) and iodomethane (1 mL, 15.9 mmol), dimethyl formamid (2 mL), morpholine (2 mL). Purification by flash chromatography on silica gel (ethyl acetate/methanol, 1:0 to 1:1). Yield: 0.05 g. $[\alpha]_D$=+21° (methanol). The amine was converted to the oxalic acid salt and recrystallized from ethanol/diethyl ether/diisopropyl ether: M.p. 114-115° C.; MS m/z (relative intensity, 70 eV) 229 (M+, 7), 129 (9), 109 (7), 58 (30), 57 (bp).

Example 67

(+)-3-(3-CHLORO-5-FLUOROPHENYL)-1-ETHYLPYRROLIDIN-3-OL

Preparation according to Example 34: (+)-1-benzyl-3-(3-chloro-5-fluorophenyl)-pyrrolidin-3-ol (0.1 g, 0.33 mmol) iodoethane (1 mL, 12.37 mmol), dimethyl formamid (2 mL), morpholine (2 mL). Purification by flash chromatography on silica gel (ethyl acetate/methanol, 1:0 to 1:1). Yield: 0.05 g. $[\alpha]_D$=+16.7° (methanol). The amine was converted to the oxalic acid salt and recrystallized from ethanol/diisopropyl ether: M.p. 113-114° C.; MS m/z (relative intensity, 70 eV) 243 (M+, 6), 157 (7), 129 (11), 72 (33), 71 (bp).

Example 68

3-(3-CHLORO-5-FLUOROPHENYL)-1-ETHYLPYRROLIDIN-3-OL 1-OXIDE 3-(3-chloro-5-fluorophenyl)-1-ethylpyrrolidin-3-ol (0.65 g, 2.67 mmol) was dissolved in dichloromethane (30 ml) and m-chlorobenzoic acid (1.38 g, 8.01 mmol) was added in portions. The mixture was stirred at ambient temperature for 15 h after which about 75% of the solvent was evaporated. The resulting slurry was purified with flash chromatography on basic Al2O3 eluted with methanol. The methanol was evaporated and dichloromethane (50 ml) and aqueous sodium carbonate (10%, 50 mL) was added. The organic phase was dried (MgSO4) and evaporated to give the title compound (0.45 g). The amine was converted to the hydrochloric acid salt and recrystallized from ethanol/diethyl ether: M.p. 158-160° C.

Example 69

3-(2,3-DIFLUOROPHENYL)-1-PROPYLPYRROLIDIN-3-OL 1-OXIDE

Preparation according to Example 68: (−)-3-(2,3-difluorophenyl)-1-propylpyrrolidin-3-ol (1.3 g, 5.4 mmol), dichloromethane (60 ml), m-chlorobenzoic acid (2.7 g, 16.2 mmol). Yield: 1.15 g. $^1$H NMR (400 MHz, CHLOROFORM-d) δ ppm 1.06 (t, J=7.41 Hz, 3H) 1.96-2.16 (m, 2H) 2.69-2.83 (m, 1H) 2.84-3.00 (m, 1H) 3.35 (dt, J=10.92, 5.46 Hz, 2H) 3.50 (br. s., 2H) 3.67 (d, J=9.75 Hz, 1H) 3.77 (d, J=10.92 Hz, 1H) 3.89-3.99 (m, 1H) 7.18 (d, J=1.56 Hz, 1H) 7.13-7.20 (m, 1H) 7.62 (td, J=6.63, 5.46 Hz, 1H)

The following Preparations are used in the synthesis of the above Examples.

Preparation 1

TERT-BUTYL 3-(3,5-DIFLUOROPHENYL)-3-HYDROXYPYRROLIDIN-1-CARBOXYLATE

To a solution of 1-bromo-3,5-difluorobenzene (3.13 g, 16.2 mmol) in dry tetrahydro-furan (40 mL), under nitrogen, was added magnesium turnings (0.39 g, 16.2 mmol). The mixture was refluxed for 1 h, cooled to ambient temperature and a solution of 1-N-boc-3-pyrrolidinone (2.0 g, 10.8 mmol) in dry tetrahydrofuran (10 mL) was added drop wise. The resulting mixture was refluxed 1 h, cooled to ambient temperature, aqueous saturated ammonium chloride solution (40 mL) was added and the mixture was extracted with ethyl acetate (3×50 mL). The combined organic phase was dried (MgSO4), filtered and evaporated to give the title compound (3.38 g). MS m/z (rel. intensity, 70 eV) 299 (M+, 1), 243 (42), 198 (49), 168 (31), 127 (28), 57 (bp).

Preparation 2

3-(3,5-DIFLUOROPHENYL)PYRROLIDIN-3-OL

To a solution of tert-butyl 3-(3,5-difluorophenyl)-3-hydroxypyrrolidin-1-carboxylate (3.38 g, 11.3 mmol) in dichloromethane (100 mL), was added trifluoroacetic acid (10 mL). The mixture was stirred for 1 h at ambient temperature after which the solvent was evaporated. Purification on a Biotage Isolute SCX-3 SPE column (washed with methanol and eluted with methanol/triethylamine, 4:1) gave the title compound (1.04 g). MS m/z (rel. intensity, 70 eV) 199 (M+, bp), 141 (52), 127 (52), 114 (36), 113 (63).

Preparation 3

(+) AND (−)-1-BENZYL-3-(3,5-DIFLUOROPHENYL)PYRROLIDIN-3-OL

Preparation according to Preparation 1: 1-Bromo-3,5-difluorobenzene (2.0 g, 10.3 mmol), magnesium turnings (0.25 g, 10.3 mmol), 1-benzylpyrrolidin-3-one (1.65 g, 9.3 mmol). Purification using flash chromatography on silica gel (ethyl acetate/isooctane, 1:4 to 1:1). Yield: 0.81 g. MS m/z (rel. intensity, 70 eV) 289 (M+, 2), 198 (26), 133 (32), 132 (23), 91 (bp). The enantiomers were separated by HPLC on Kromasil 5-Cellucoat (heptane/2-propanol/diethyl amine, 99:1:0.1): (+)-enantiomer (0.23 g). $[\alpha]_D = +28.3°$ (methanol). MS m/z (rel. intensity, 70 eV) 289 (M+, 5), 198 (48), 133 (48), 132 (37), 91 (bp). (−)-enantiomer (0.35 g). $[\alpha]_D = -28.1°$ (methanol). MS m/z (rel. intensity, 70 eV) 289 (M+, 9), 198 (58), 133 (48), 132 (40), 91 (bp).

Preparation 4

3-(3,4-DIFLUOROPHENYL)PYRROLIDIN-3-OL

To a mixture of 1-benzyl-3-(3,4-difluorophenyl)pyrrolidin-3-ol (0.55 g, 1.9 mmol) and ammonium formiate (0.36 g, 5.7 mmol) in ethanol (20 mL) was added palladium on carbon (0.11 g) and the mixture was refluxed for 1 h, cooled to ambient temperature and filtered through a pad of celite. The filtrate was evaporated to give the title compound (0.4 g). MS m/z (rel. intensity, 70 eV) 199 (M+, bp), 180 (51), 150 (60), 141 (90), 113 (75).

Preparation 5

TERT-BUTYL 3-(3-CHLORO-5-FLUOROPHENYL)-3-HYDROXYPYRROLIDIN-1-CARBOXYLATE

To a solution of 1-bromo-3-chloro-5-fluorobenzene (4.0 g, 19.1 mmol) in dry tetrahydrofuran (40 mL), under nitrogen, was added magnesium turnings (0.47 g, 21.0 mmol) and a small piece of iodine. The mixture was heated with a heat-gun until the colour disappeared and then stirred at ambient temperature for 0.5 h after which a solution of 1-N-boc-3-pyrrolidinone (2.8 g, 15.3 mmol) in dry tetrahydrofuran (10 mL) was added drop wise. The reaction mixture was stirred for 0.5 h at ambient temperature and then quenched with water (70 mL). Aqueous saturated ammonium chloride (20 mL) was added and the mixture was extracted with ethyl acetate (2×100 mL). The combined organic phase was dried (MgSO4), filtered and evaporated. Purification by flash column chromatography on silica gel (ethyl acetate/isooctane, 1:1) gave the title compound (2.43 g). MS m/z (rel. intensity, 70 eV) 315 (M+, 1), 259 (14), 214 (22), 184 (13), 143 (11), 57 (bp).

Preparation 6

TERT-BUTYL 3-(3-CHLORO-4-FLUOROPHENYL)-3-HYDROXYPYRROLIDIN-1-CARBOXYLATE

Preparation according to Preparation 5: 4-bromo-2-chloro-1-fluorobenzene (4.0 g, 19.1 mmol), dry tetrahydrofuran (50 mL), magnesium turnings (0.5 g, 21.0 mmol) and 1-N-boc-3-pyrrolidinone (3.89 g, 21.0 mmol). Yield: 1.65 g. MS m/z (rel. intensity, 70 eV) 315 (M+, 1), 259 (50), 214 (63), 157 (44), 57 (bp).

Preparation 7

3-(3-CHLORO-4-FLUOROPHENYL)PYRROLIDIN-3-OL

Preparation according to Preparation 2: tert-Butyl 3-(3-chloro-4-fluorophenyl)-3-hydroxypyrrolidin-1-carboxylate (0.87 g, 2.77 mmol), dichloromethane (3 mL) and trifluoroacetic acid (3 mL). Stirred for 5 h. Yield: 0.31 g. MS m/z (rel. intensity, 70 eV) 215 (M+, 72), 157 (bp), 133 (53), 130 (62), 129 (98).

Preparation 8

TERT-BUTYL 3-(2,3-DIFLUOROPHENYL)-3-HYDROXYPYRROLIDIN-1-CARBOXYLATE

Preparation according to Preparation 23: 1-bromo-2,3-difluorobenzene (3.12 g, 16.2 mmol), dry diethyl ether (30 mL), N-butyl lithium (2.5 M, 6.5 mL, 16.2 mmol), 1-N-boc-3-pyrrolidinone (2.0 g, 10.8 mmol). Stirred 2 h at −78° C. before addition, and 1 h at ambient temperature after addition of 1-N-boc-3-pyrrolidinone. Yield: 1.72 g. MS m/z (rel. intensity, 70 eV) 299 (M+, 1), 243 (46), 226 (38), 198 (68), 57 (bp).

Preparation 9

3-(2,3-DIFLUOROPHENYL)PYRROLIDIN-3-OL

Preparation according to Preparation 2: tert-butyl 3-(2,3-difluorophenyl)-3-hydroxy-pyrrolidin-1-carboxylate (1.72 g, 5.75 mmol), dichloromethane (3 mL) and trifluoroacetic acid (3 mL). Stirred for 3 h. Yield: 0.31 g. MS m/z (rel. intensity, 70 eV) 199 (M+, bp), 141 (87), 127 (60), 114 (38), 113 (63).

Preparation 10

TERT-BUTYL 3-(3,5-DICHLOROPHENYL)-3-HYDROXYPYRROLIDIN-1-CARBOXYLATE

Preparation according to Preparation 5: 1-bromo-3,5-dichlorobenzene (5.0 g, 22.1 mmol), dry tetrahydrofuran (100 mL), magnesium turnings (0.54 g, 24.3 mmol) and 1-N-boc-3-pyrrolidinone (3.25 g, 17.7 mmol). Yield: 2.1 g. MS m/z (rel. intensity, 70 eV) 332 (M+, 1), 232 (17), 231 (23), 230 (22), 57 (bp).

Preparation 11

3-(3,5-DICHLOROPHENYL)PYRROLIDIN-3-OL

Preparation according to Preparation 2: tert-butyl 3-(3,5-dichlorophenyl)-3-hydroxypyrrolidin-1-carboxylate (1.3 g, 3.9 mmol), dichloromethane (10 mL) and trifluoroacetic acid (3 mL). Stirred for 1 h. Purification by HPLC on Waters OBD C18, 5 μm (MeOH/33 mM NH3, 20:80 to 40:60). Yield: 0.57 g. MS m/z (rel. intensity, 70 eV) 233 (M+, 64), 231 (M+, bp), 145 (56), 111 (55), 75 (72).

Preparation 12

TERT-BUTYL 3-(3,4-DICHLOROPHENYL)-3-HYDROXYPYRROLIDIN-1-CARBOXYLATE

Preparation according to Preparation 1: 4-bromo-1,2-dichlorobenzene (2.0 g, 8.85 mmol), dry tetrahydrofuran (35 mL), magnesium turnings (0.21 g, 8.85 mmol) and 1-N-boc-3-pyrrolidinone (1.63 g, 8.85 mmol). Refluxed for 1 h before addition of 1-N-boc-3-pyrrolidinone and 2 h after addition. Yield: 1.0 g. MS m/z (rel. intensity, 70 eV) 332 (M+, 1), 275 (41), 232 (37), 231 (28), 230 (52), 57 (bp).

Preparation 13

3-(3,4-DICHLOROPHENYL)PYRROLIDIN-3-OL

Preparation according to Preparation 2: tert-butyl 3-(3,4-dichlorophenyl)-3-hydroxypyrrolidin-1-carboxylate (1.0 g, 3.0 mmol), dichloromethane (2 mL) and trifluoroacetic acid (1 mL). Stirred for 12 h. Yield: 0.34 g. MS m/z (rel. intensity, 70 eV) 233 (M+, 66), 231 (M+, bp), 173 (59), 145 (47), 75 (40).

Preparation 14

1-BENZYL-3-(3,5-DIFLUOROPHENYL)-3-FLUOROPYRROLIDINE

To a cooled (0° C.) solution of 1-benzyl-3-(3,5-difluorophenyl)pyrrolidin-3-ol (1.9 g, 6.6 mmol) in dichloromethane (20 mL) was added dropwise diethylaminosulphurtrifluoride (1.05 mL, 7.26 mmol) dissolved in dichloromethane (5 mL) and the mixture was stirred at ambient temperature for 1 h. Additional diethylaminosulphurtrifluoride (0.1 mL, 0.69 mmol) was added and stirring was continued 0.5 h. Aqueous sodium carbonate (10%, 50 mL) was added and the phases separated. The aqueous phase was extracted with dichloromethane (50 mL) and the pooled organic phase was dried (MgSO4) and evaporated. Purification by flash column chromatography gave the title compound (0.65 g). MS m/z (rel. intensity, 70 eV) 291 (M+, 44), 200 (17), 133 (51), 132 (45), 91 (bp).

Preparation 15

TERT-BUTYL 3-(3,5-DICHLOROPHENYL)-3-FLUOROPYRROLIDIN-1-CARBOXYLATE

To a cooled (0° C.) solution of tert-butyl 3-(3,5-dichlorophenyl)-3-hydroxypyrrolidin-1-carboxylate (0.88 g, 2.65 mmol) in dichloromethane (50 mL) was added dropwise diethylaminosulphurtrifluoride (0.35 mL, 2.65 mmol) dissolved in dichloromethane (20 mL) and the mixture was stirred at 0° C. for 20 minutes and at ambient temperature for 10 minutes. Aqueous sodium carbonate (10%, 50 mL) was added and the phases separated. The aqueous phase was extracted with dichloromethane (2×50 mL) and the pooled organic phase was dried (Na2SO4) and evaporated. Purification by flash column chromatography gave the title compound (0.45 g). MS m/z (rel. intensity, 70 eV) 334 (M+, 1), 278 (8), 277 (6), 260 (8), 57 (bp).

Preparation 16

3-(2,4-DIFLUOROPHENYL)-3-PYRROLIDIN-3-OL

A mixture of 1-benzyl-3-(2,4-difluorophenyl)-3-pyrrolidin-3-ol (1.5 g, 5.2 mmol) and ammonium formiate (3.26 g, 52 mmol) in methanol (50 mL) was purged with nitrogen and palladium on carbon (150 mg) was added. The mixture was refluxed for 1 h. The mixture was filtered and the filtrate was evaporated. Aqueous sodium carbonate (10%) was added and the aqueous phase was extracted with ethyl acetate (2×50 mL). The combined organic phase was dried (Na2SO4) and evaporated to give the title compound (0.740 g). MS m/z (relative intensity, 70 eV) 199 (M+, 80), 151 (30), 141 (bp), 127 (44), 113 (41).

Preparation 17

1-BENZYL-3-(2,4-DIFLUOROPHENYL)-3-PYRROLIDIN-3-OL

To a solution of 1-bromo-2,4-difluorobenzene (7.49 g, 38.5 mmol) in dry diethyl ether (30 mL), under nitrogen, was added dropwise at −78° C., n-hexyllithium (2.3 M in hexane, 16.77 mL, 38.5 mmol). The mixture was stirred for 1 min after which a solution of 1-benzylpyrrolidin-3-one (4.5 g, 25.7 mmol) in dry diethyl ether (30 mL) was added dropwise. The resulting mixture was brought to ambient temperature, water (50 mL) was added and the mixture was extracted with ethyl acetate (2×50 mL). The combined organic phase was washed with brine, dried (Na2SO4), filtered and evaporated. Purification by flash column chromatography on silica gel (ethyl acetate/isooctane, 1:1) gave the title compound (5.7 g). MS m/z (rel. intensity, 70 eV) 289 (M+, 5), 198 (60), 133 (47), 132 (38), 91 (bp).

Preparation 18

ENANTIOMER E1 OF 3-(3,4-DIFLUOROPHENYL)PYRROLIDIN-3-OL

A mixture of enantiomer E1 of 1-benzyl-3-(3,4-difluorophenyl)pyrrolidin-3-ol (0.81 g, 2.8 mmol), methanol (15 mL) and palladium on carbon (160 mg) was purged with nitrogen. Triethyl silane (6.5 g, 56 mmol) was added drop wise and the resulting mixture was stirred at ambient temperature for 3 h after which the mixture was filtrated over celite and evaporated. Methanol (15 mL) and palladium on carbon (160 mg) was added and the mixture was purged with nitrogen. Triethyl silane (6.5 g, 56 mmol) was added in 5 equal portions over 1.5 h and the resulting mixture was stirred at ambient temperature for 11.5 h. The mixture was filtrated over celite, evaporated and purified on a Biotage (solute SCX-3 SPE column (washed with methanol and eluted with methanol/triethylamine, 4:1) to give the title compound (0.52 g). MS m/z (relative intensity, 70 eV) 199 (M+, bp), 141, (97), 127 (54), 114 (48), 113 (85).

Preparation 19

ENANTIOMER E2 OF 3-(3,4-DIFLUOROPHENYL)PYRROLIDIN-3-OL

Preparation according to Preparation 18: Enantiomer E2 of 1-benzyl-3-(3,4-difluorophenyl)pyrrolidin-3-ol (0.835 g, 2.89 mmol), methanol (15 mL), palladium on carbon (165 mg), triethyl silane (6.7 g, 57.7 mmol). Reaction restart: Methanol (15 mL), palladium on carbon (165 mg), triethyl silane (6.7 g, 57.7 mmol). Purification on a Biotage Isolute SCX-3 SPE column (washed with methanol and eluted with methanol/triethylamine 4:1). Yield: 0.54 g. MS m/z (relative intensity, 70 eV) 199 (M+, 85), 141, (bp), 127 (58), 114 (53), 113 (98).

Preparation 20

ENANTIOMER E1 OF 3-(3,5-DIFLUOROPHENYL)PYRROLIDIN-3-OL

A mixture of (+)-1-benzyl-3-(3,5-difluorophenyl)pyrrolidin-3-ol (0.853 g, 2.95 mmol), methanol (15 mL) and palladium on carbon (170 mg) was purged with nitrogen. Triethyl silane (3.42 g, 29.5 mmol) was added in 7 equal portions over 3.5 h and the resulting mixture was stirred at ambient temperature for 3 h. The mixture was filtrated over celite, evaporated and Purification on a Biotage Isolute SCX-3 SPE column (washed with methanol and eluted with methanol/triethylamine, 4:1) gave the title compound (0.53 g). MS m/z (relative intensity, 70 eV) 199 (M+, bp), 141, (61), 127 (73), 114 (59), 113 (88).

Preparation 21

ENANTIOMER E2 OF 3-(3,5-DIFLUOROPHENYL)PYRROLIDIN-3-OL

Preparation according to Example 18: (−)-1-benzyl-3-(3,5-difluorophenyl)pyrrolidin-3-ol (0.81 g, 2.8 mmol), methanol (15 mL), palladium on carbon (165 mg) and triethyl silane (3.25 g, 28 mmol). Yield 0.53 g. MS m/z (relative intensity, 70 eV) 199 (M+, bp), 141, (48), 127 (56), 114 (43), 113 (62).

Preparation 22

(+) AND (−)-1-BENZYL-3-(3-CHLORO-2-FLUOROPHENYL)PYRROLIDIN-3-OL

To a solution of 1-bromo-3-chloro-2-fluorobenzene (6 g, 28.7 mmol) in dry tetrahydrofuran (40 mL), under nitrogen, was added magnesium turnings (0.82 g, 25.8 mmol). The mixture was refluxed for 30 min, cooled to ambient temperature and a solution of 1-benzylpyrrolidin-3-one (4.5 g, 25.8 mmol) in dry tetrahydrofuran (20 mL) was added drop wise. The resulting mixture was stirred at 55° C. for 3 h after which saturated aqueous ammonium chloride (50 mL) was added and the mixture was extracted with ethyl acetate (3×50 mL). The combined organic phase was dried (Na2SO4) and evaporated. Purification by flash chromatography on silica gel (isooctane/ethyl acetate, 1:1). Yield: 0.9 g. The enantiomers were separated by HPLC on Kromasil 5-Cellucoat (heptane/2-propanol/diethyl amine, 99:1:0.1): (+)-enantiomer (0.315 g). $[\alpha]_D$=+59.3° (methanol). MS m/z (rel. intensity, 70 eV) 305 (M+, 8), 214 (40), 133 (72), 132 (51), 91 (bp). (−)-enantiomer (0.33 g). $[\alpha]_D$=−60.4° (methanol). MS m/z (rel. intensity, 70 eV) 305 (M+, 23), 214 (89), 133 (93), 132 (66), 91 (bp).

The enantiomers can also be separated by the following method: 1.0 eq of (+) and (−)-1-benzyl-3-(3-chloro-2-fluorophenyl)pyrrolidin-3-ol and 2.0 eq of (−)-dibenzoyl-L-tartaric acid was dissolved in warm methanol (2 L per mole) and cooled to −20° C. The salt formed contained (+)-1-benzyl-3-(3-chloro-2-fluorophenyl)pyrrolidin-3-ol of high enantiomeric excess.

Preparation 23

(+) AND (−)-1-BENZYL-3-(2,3-DIFLUOROPHENYL)PYRROLIDIN-3-OL

To a solution of 1-bromo-2,3-difluorobenzene (5.79 g, 30 mmol) in dry diethyl ether (50 mL) under nitrogen at −78° C., was added dropwise n-butyllithium (2.5 M in hexane, 13.2 mL, 33 mmol). The mixture was stirred for 30 min at −78° C. after which a solution of 1-benzylpyrrolidin-3-one (5.25 g, 30 mmol) in dry diethyl ether (15 mL) was added drop wise. The mixture was stirred at −78° C. for 1 h and at ambient temperature for 1 h. Saturated aqueous ammonium chloride (50 mL) was added and the mixture was extracted with ethyl acetate (2×50 mL). The combined organic phase was dried (Na2SO4), filtered and evaporated. Purification by flash chromatography on silica gel (ethylacetate/isooctane/triethylamine, 10:85:5). Yield: 3.7 g. The enantiomers were separated by HPLC on Kromasil 5-Cellucoat (heptane/2-propanol/diethyl amine, 99:1:0.1): (+)-enantiomer (1.69 g). $[\alpha]_D$=+47.0° (methanol). MS m/z (rel. intensity, 70 eV) 289 (M+, 38), 198 (76), 133 (64), 132 (47), 91 (bp). (−)-enantiomer (1.54 g). $[\alpha]_D$=−46.2° (methanol). MS m/z (rel. intensity, 70 eV) 289 (M+, 11), 198 (43), 133 (56), 132 (40), 91 (bp).

Preparation 24

3-(3-CHLORO-5-FLUOROPHENYL)PYRROLIDIN-3-OL

To a solution of tert-butyl 3-(3-chloro-5-fluorophenyl)-3-hydroxypyrrolidin-1-carboxylate (2.43 g, 7.7 mmol) in dichloromethane (80 mL), was added trifluoroacetic acid (5 mL). The mixture was stirred for 1.5 h after which the mixture was basified with aqueous sodium carbonate (10%, 50 mL) and evaporated. Ethyl acetate (100 mL) was added, the mixture was washed with brine and the organic phase was dried (MgSO4) and evaporated. Purification on a Biotage (solute SCX-3 SPE column (washed with methanol and eluted with methanol/triethylamine, 4:1), and by HPLC on Waters OBD 018, 5 μm (MeOH/33 mM NH3, 20:80 to 0:100), gave the title compound (1.07 g). MS m/z (rel. intensity, 70 eV) 215 (M+, bp), 157 (47), 129 (65), 109 (61), 95 (43).

Preparation 25

3-(3-CHLORO-2-FLUOROPHENYL)PYRROLIDIN-3-OL

Preparation according to Preparation 2: tert-Butyl 3-(3-chloro-2-fluorophenyl)-3-hydroxypyrrolidin-1-carboxylate (4.42 g, 14 mmol), dichloromethane (100 mL), trifluoroacetic acid (10 mL). Stirred for 1 h. Yield: 2.24 g.

Preparation 26

TERT-BUTYL 3-(3-CHLORO-2-FLUOROPHENYL)-3-HYDROXYPYRROLIDIN-1-CARBOXYLATE

To a solution of 1-bromo-3-chloro-2-fluorobenzene (5.0 g, 23.8 mmol) in dry tetrahydrofuran (50 mL) under nitrogen at −78° C., was added dropwise n-butyllithium (2.5 M in tetrahydrofuran, 9.5 mL, 23.8 mmol). The mixture was stirred for 0.5 h at −78° C. after which a solution of 1-N-boc-3-pyrrolidinone (4.37 g, 23.8 mmol) in dry tetrahydrofuran (20 mL) was added drop wise. The resulting mixture was brought to ambient temperature, aqueous saturated ammonium chloride (50 mL) was added and the mixture was extracted with ethyl acetate (3×50 mL). The combined organic phase was dried (MgSO4), filtered and evaporated. Purification by flash column chromatography on silica gel (ethyl acetate/methanol, 4:1 to 1:1) gave the title compound (4.42 g). MS m/z (rel. intensity, 70 eV) 315 (M+, 1), 259 (16), 214 (31), 157 (17), 57 (bp).

Preparation 27

3-(2,3-DICHLOROPHENYL)PYRROLIDIN-3-OL

Preparation according to Preparation 2: tert-Butyl 3-(2,3-dichlorophenyl)-3-hydroxypyrrolidin-1-carboxylate (1.23 g, 3.7 mmol), dichloromethane (20 mL), trifluoroacetic acid (3 mL). Stirred for 0.5 h. Purification by HPLC on Waters OBD C18, 5 μm (MeOH/33 mM NH3, 20:80 to 0:100). Yield: 0.35 g. MS m/z (rel. intensity, 70 eV) 233 (M+, 6), 231 (M+, 10), 198 (32), 196 (bp), 75 (37), 56 (27).

Preparation 28

TERT-BUTYL 3-(2,3-DICHLOROPHENYL)-3-HYDROXYPYRROLIDIN-1-CARBOXYLATE

Preparation according to Example 23: 1-bromo-2,3-dichlorobenzene (2.1 g, 9.23 mmol) in dry tetrahydrofuran (40 mL), n-butyllithium (2.5 M in tetrahydrofuran, 3.7 mL, 9.23 mmol), 1-N-boc-3-pyrrolidinone (1.13 g, 6.15 mmol) in dry tetrahydrofuran (10 mL). Purified by flash column chromatography on silica gel (isooctane/ethyl acetate, 4:1 to 1:1). Yield: 1.23 g. MS m/z (rel. intensity, 70 eV) 230 (25), 196 (46), 172 (19), 57 (bp), 56 (29).

Preparation 29

3-(3,4-DIFLUOROPHENYL)PYRROLIDIN-3-OL

Preparation according to Preparation 2: tert-Butyl 3-(3,4-difluorophenyl)-3-hydroxy-pyrrolidin-1-carboxylate (2.6 g, 8.69 mmol), dichloromethane (3 mL) and trifluoroacetic acid (3 mL). Stirred for 4 h. Yield: 1.32 g. MS m/z (relative intensity, 70 eV) 199 (M+, 876), 141 (bp), 127 (58), 113 (99), 63 (55).

Preparation 30

TERT-BUTYL 3-(3,4-DIFLUOROPHENYL)-3-HYDROXYPYRROLIDIN-1-CARBOXYLATE

To a solution of 1-bromo-3,4-difluorobenzene (3.5 g, 18.13 mmol) in dry diethyl ether (25 mL) under nitrogen at −78° C., was added dropwise n-butyllithium (2.5 M in hexane, 7.25 mL, 18.13 mmol). The mixture was stirred for 30 min at −78° C. after which a solution of 1-N-boc-3-pyrrolidinone (3.35 g, 18.13 mmol) in dry diethyl ether (25 mL) was added drop wise. The mixture was stirred at −78° C. for 10 min and then brought to ambient temperature over a period of 2 h. Aqueous sodium carbonate (10%) was added and the mixture was extracted with ethyl acetate (3×50 mL). The combined organic phase was dried (Na2SO4), filtered and evaporated. Purification by flash column chromatography on silica gel (isooctane/ethyl acetate, 4:1 to 1:1) gave the title compound (2.6 g). MS m/z (rel. intensity, 70 eV) 243 (18), 198 (23), 141 (18), 127 (21), 57 (bp).

Preparation 31

Enantiomer E2 of 3-(3,5-DIFLUOROPHENYL)PYRROLIDIN-3-OL

A mixture of (−)-1-benzyl-3-(3,5-difluorophenyl)pyrrolidin-3-ol (2.73 g, 9.44 mmol), methanol (20 mL) and palladium on carbon (500 mg) was purged with nitrogen. Triethyl silane (15.09 mL, 94.4 mmol) was added drop wise over 3 h and the mixture was stirred at ambient temperature for 24 h. The mixture was filtrated over celite, evaporated and purified by flash chromatography on silica gel (ethyl acetate/methanol/triethylamine, 1:0 to 0:4:1) to give the title compound (1.4 g). MS m/z (relative intensity, 70 eV) 199 (M+, bp), 141, (50), 127 (58), 114 (50), 113 (71).

Preparation 32

Enantiomer E1 of 3-(3,5-DIFLUOROPHENYL)PYRROLIDIN-3-OL

Preparation according to Preparation 18: (+)-1-benzyl-3-(3,5-difluorophenyl)pyrrolidin-3-ol (2.89 g, 10 mmol), methanol (20 mL), palladium on carbon (500 mg), triethyl silane (15.97 mL, 100 mmol). Yield 0.92 g. MS m/z (relative intensity, 70 eV) 199 (M+, bp), 141, (61), 127 (72), 114 (57), 113 (84).

Preparation 33

(+) AND (−)-1-BENZYL-3-(3,5-DIFLUOROPHENYL)PYRROLIDIN-3-OL

The enantiomers of 1-benzyl-3-(3,5-difluorophenyl)pyrrolidin-3-ol (7.2 g, 24.9 mmol) were separated by HPLC on Kromasil 10-Cellucoat (heptane/2-propanol/diethyl amine, 97.5:2.5:0.1). (+)-Enantiomer (2.89 g). $[\alpha]_D$=+28.3° (methanol). MS m/z (relative intensity, 70 eV) 289 (M+, 5), 198, (48), 133 (48), 132 (37), 91 (bp). (−)-Enantiomer (2.89 g). $[\alpha]_D$=−28.1° (methanol). MS m/z (relative intensity, 70 eV) 289 (M+, 9), 198 (58), 133 (48), 132 (40), 91 (bp).

Preparation 34

1-BENZYL-3-(3,5-DIFLUOROPHENYL)PYRROLIDIN-3-OL

To a solution of 1-bromo-3,5-difluorobenzene (10 g, 57.14 mmol) in dry tetrahydrofuran (60 mL), under nitrogen, was added magnesium turnings (1.37 g, 57.14 mmol) and one crystal of Iodine. The mixture started to reflux spontaneously and when all magnesium was consumed, a solution of 1-benzylpyrrolidin-3-one (10 g, 57.14 mmol) in dry tetrahydrofuran (40 mL) was added drop wise. The resulting mixture was heated to 60° C. for 2 h after which aqueous saturated ammonium chloride solution (50 mL) was added. The mixture was extracted with ethyl acetate (2×50 mL) and the combined organic phase was dried (Na2SO4) and evaporated. Purification twice by flash chromatography on silica gel (isooctane/ethyl acetate, 1:1 and 6:4) gave the title compound (5.5 g). MS m/z (rel. intensity, 70 eV) 289 (M+, 9), 198 (61), 133 (51), 132 (41), 91 (bp).

Preparation 35

1-BENZYL-3-(2,3-DIFLUOROPHENYL)PYRROLIDIN-3-OL

To a solution of 1-bromo-2,3-difluorobenzene (25 g, 129.5 mmol) in dry diethyl ether (150 mL), under nitrogen at −78° C. was added drop wise n-butyllithium (2.5 M in hexane, 51.8 mL, 129.5 mmol). The mixture was stirred for 30 min after which a solution of 1-benzylpyrrolidin-3-one (20.4 g, 116.5 mmol) in dry diethyl ether (50 mL) was added drop wise. The mixture was stirred at −78° C. for 30 min and for 2 h at ambient temperature. Aqueous saturated ammonium chloride solution (50 mL) was added and the mixture was extracted with ethyl acetate (2×50 mL). The combined organic phase was dried (Na2SO4), filtered and evaporated. Purification by flash chromatography on silica gel (isooctane/ethyl acetate/triethyl amine, 75:20:5) gave the title compound (19.5 g). MS m/z (relative intensity, 70 eV) 289 (M+, 20), 198 (69), 133 (72), 132 (51), 91 (bp).

Preparation 36

(+) AND (−)-1-BENZYL-3-THIEN-2-YLPYRROLIDIN-3-OL

The enantiomers of 1-benzyl-3-thien-2-ylpyrrolidin-3-ol (2.9 g, 11.2 mmol) were separated by HPLC on Kromasil 10-Cellucoat (heptane/2-propanol/diethyl amine, 92.5:7.5:0.1). (+)-Enantiomer (0.137 g). $[\alpha]_D$=+26.3° (methanol). MS m/z (relative intensity, 70 eV) 259 (M+, 4), 168 (42), 133 (24), 132 (28), 91 (bp). (−)-Enantiomer (0.102 g). $[\alpha]_D$=−25.0° (methanol). MS m/z (relative intensity, 70 eV) 259 (M+, 6), 168 (51), 133 (31), 132 (31), 91 (bp).

Preparation 37

(+) AND (−)-1-BENZYL-3-(3-CHLORO-5-FLUOROPHENYL)PYRROLIDIN-3-OL

The enantiomers of 1-benzyl-3-(3-chloro-5-fluorophenyl)pyrrolidin-3-ol (0.92 g, 3 mmol) were separated by HPLC on Kromasil 10-Cellucoat (heptane/2-propanol/diethyl amine, 95:5:0.1). (+)-Enantiomer (0.2 g). $[\alpha]_D$=+31.9° (methanol). MS m/z (relative intensity, 70 eV) 305 (M+, 10), 214 (80), 133 (75), 132 (57), 91 (bp). (−)-Enantiomer (2.89 g). $[\alpha]_D$=−30.2° (methanol). MS m/z (relative intensity, 70 eV) 305 (M+, 16), 214 (bp), 133 (67), 132 (51), 91 (81).

Preparation 38

1-BENZYL-3-(3-CHLORO-5-FLUOROPHENYL)PYRROLIDIN-3-OL

To a solution of 1-bromo-3-chloro-5-fluorobenzene (5 g, 23.9 mmol) in dry tetrahydrofuran (50 mL), under nitrogen, was added magnesium turnings (0.58 g, 26.2 mmol) and one crystal of iodine. The mixture was heated until self sustained reflux started. When the reflux ceased a solution of 1-N-benzyl-3-pyrrolidone (4.17 g, 23.9 mmol) in dry tetrahydrofuran (50 mL) was added drop wise. The resulting mixture was stirred at ambient temperature for 15 min after which aqueous saturated ammonium chloride solution (40 mL) was added. The aqueous phase was extracted with tert-butyl methyl ether the combined organic phases were extracted with aqueous HCl (10%, 200 mL), the aqueous phase was basified with aqueous NaOH (5 M) and the mixture was extracted with ethyl acetate (2×50 mL). The combined organic phase was dried (MgSO4), filtered and evaporated. Purification on silica gel (isooctane/ethyl acetate, 1:1 to 0:1) gave the title compound (0.92 g).

Preparation 39

(+) AND (−)-1-BENZYL-3-(3-CHLORO-2-FLUOROPHENYL)PYRROLIDIN-3-OL

The enantiomers of 1-benzyl-3-(3-chloro-2-fluorophenyl)pyrrolidin-3-ol (5 g, 16.4 mmol) were separated by HPLC on Kromasil 10-Cellucoat (heptane/2-propanol/diethyl amine, 95:5:0.1). (+)-Enantiomer (1.63 g). $[\alpha]_D$=+59.3° (methanol). MS m/z (relative intensity, 70 eV) 305 (M+, 8), 214 (40), 133 (72), 132 (51), 91 (bp). (−)-Enantiomer (1.48 g). $[\alpha]_D$=−60.4° (methanol). MS m/z (relative intensity, 70 eV) 305 (M+, 7), 214 (38), 133 (70), 132 (50), 91 (bp).

Preparation 40

1-BENZYL-3-(3-CHLORO-2-FLUOROPHENYL)PYRROLIDIN-3-OL

To a solution of 1-bromo-3-chloro-2-fluorobenzene (11.8 g, 56.3 mmol) in dry diethyl ether (100 mL), under nitrogen at −78° C. was added drop wise n-butyllithium (2.5 M in hexane, 22.5 mL, 56.3 mmol). The mixture was stirred at −78° C. for 10 min after which a solution of 1-benzylpyrrolidin-3-one (10 g, 56.3 mmol) in dry diethyl ether (50 mL) was added drop wise. The resulting mixture was brought to ambient temperature, aqueous ammonium chloride solution (50%, 50 mL) was added and the mixture was extracted with ethyl acetate (2×50 mL). The combined organic phase was dried (MgSO4), filtered and evaporated. Purification by flash chromatography on silica gel (isooctane/ethyl acetate, 1:1) gave the title compound (16 g). MS m/z (relative intensity, 70 eV) 305 (M+, 9), 214 (41), 133 (71), 132 (50), 91 (bp).

Preparation 41

ENANTIOMER E1 AND E2 OF 1-BENZYL-3-(3,4-DIFLUOROPHENYL)PYRROLIDIN-3-OL

To a solution of 1-bromo-3,4-difluorobenzene (4 g, 20.7 mmol) in dry diethyl ether (25 mL), under nitrogen at −78° C. was added drop wise n-butyllithium (2.5 M in hexane, 8.3 mL, 20.7 mmol). The mixture was stirred at −78° C. for 1 h after which a solution of 1-benzylpyrrolidin-3-one (3.62 g, 20.7 mmol) in dry diethyl ether (15 mL) was added drop wise. The mixture was stirred at −78° C. for 15 min and at ambient temperature for 1 h after which aqueous saturated ammonium chloride solution (50 mL) was added and the mixture was extracted with ethyl acetate (2×50 mL). The combined organic phase was dried (Na2SO4), filtered and evaporated. Purification twice by flash chromatography on silica gel (isooctane/ethyl acetate, 4:1 to 1:1 and 3:2 isocratic) gave the title compound (2.32 g). MS m/z (relative intensity, 70 eV) 289 (M+, 4), 198 (23), 133 (29), 132 (23), 91 (bp). The enantiomers were separated by chiral HPLC (Kromasil

Preparation 42

1-BENZYL-3-(2,3-DIFLUOROPHENYL)-3-FLUOROPYRROLIDINE

To a solution of 1-benzyl-3-(2,3-difluorophenyl)pyrrolidin-3-ol (5.3 g, 18.3 mmol) in dichloromethane (30 mL) at 0° C. was added drop wise, a solution of diethylaminosulfur trifluoride (2.93 mL, 22.4 mmol) in dichloromethane. The cooling was removed and the mixture was stirred at ambient temperature for 2 h after which an additional amount of diethylaminosulfur trifluoride (0.1 mL, 0.76 mmol) was added. The mixture was stirred for 1 h at ambient temperature after which aqueous sodium hydrogen carbonate (10%) was added and the mixture was extracted with ethyl acetate. The organic phase was dried (Na2SO4), filtered and evaporated. Purification by flash chromatography on silica gel (isooctane/ethyl acetate, 1:0 to 1:1) gave the title compound (2 g). MS m/z (relative intensity, 70 eV) 291 (M+, 32), 200 (18), 133 (54), 91 (bp), 65 (20).

Preparation 43

TERT-BUTYL 3-(3-CHLORO-5-FLUOROPHENYL)-3-HYDROXYPYRROLIDIN-1-CARBOXYLATE

To a slurry of magnesium turnings (0.38 g, 14.4 mmol), a small crystal of iodine and a few drops of dibromoethane in dry tetrahydrofuran (30 mL) under nitrogen was added a solution of 1-bromo-3-chloro-5-fluorobenzene (3 g, 14.4 mmol) in dry tetrahydrofuran (30 mL). The mixture was refluxed for 30 min and then cooled to ambient temperature after which a solution of 1-N-boc-3-pyrrolidone (2.9 g, 15.8 mmol) in a small amount of dry tetrahydrofuran was added. The resulting mixture was stirred at ambient temperature for 2 h after which Aqueous sodium carbonate (10%) was added and the mixture was extracted with ethyl acetate (3×50 mL). The combined organic phase was dried (Na2SO4), filtered and evaporated. Purification by flash column chromatography on silica gel (isooctane/ethyl acetate, 1:0 to 1:1) gave the title compound (1.6 g). MS m/z (relative intensity, 70 eV) 315 (M+, 1), 259 (99), 214 (99), 143 (65), 57 (bp).

Preparation 44

3-(3-CHLORO-5-FLUOROPHENYL)PYRROLIDIN-3-OL

Preparation according to Preparation 2: tert-Butyl 3-(3-Chloro-5-fluorophenyl)-3-hydroxypyrrolidin-1-carboxylate (1.6 g, 5.08 mmol), dichloromethane (3 mL) and trifluoroacetic acid (3 mL). Stirred for 4 h. Purification on a Biotage (solute SCX-3 SPE column (washed with methanol and eluted with methanol/triethylamine, 4:1) and by HPLC on Waters OBD C18, 5 μm (MeOH/33 mM NH3, 20:80 to 100:0). Yield: 1.1 g. MS m/z (rel. intensity, 70 eV) 215 (M+, bp), 129 (65), 109 (52), 157 (46), 95 (44).

Preparation 45

3-(3,4-DIFLUOROPHENYL)PYRROLIDIN-3-OL

To a solution of tert-butyl-3-(3,4-difluorophenyl)-3-hydroxypyrrolidin-1-carboxylate (0.34 g, 1.13 mmol) in dichloromethane (2 mL), was added trifluoroacetic acid (2 mL). The mixture was stirred for 4 h at ambient temperature. The mixture was Purification on a Biotage Isolute SCX-3 SPE column (washed with methanol and eluted with methanol/triethylamine, 4:1) gave the title compound (0.19 g). MS m/z (relative intensity, 70 eV) 199 (M+, 44), 151 (82), 141 (98), 113 (bp), 63 (99).

Preparation 46

TERT-BUTYL-3-(3,4-DIFLUOROPHENYL)-3-HYDROXYPYRROLIDIN-1-CARBOXYLATE

To a mixture of 1-benzyl-3-(3,4-difluorophenyl)pyrrolidin-3-ol (2.83 g, 9.8 mmol), polymethyl hydrosiloxane (1.8 g, 30 mmol) and palladium hydroxide (150 mg) on carbon in ethanol (100 mL) was added di-tert-butyl dicarbonate (2.4 g, 10.77 mmol). The mixture was stirred for 24 h at ambient temperature, filtrated over celite and evaporated. Purification by flash chromatography on silica gel (isooctane/ethyl acetate, 1:2) gave the title compound (2.79 g). MS m/z (relative intensity, 70 eV) 299 (M+, 1), 243 (30), 198 (37), 127 (26), 57 (bp).

Preparation 47

1-BENZYL-3-(3,4-DIFLUOROPHENYL)PYRROLIDIN-3-OL

To a solution of 1-bromo-3,4-difluorobenzene (5.0 g, 25.9 mmol) in dry diethyl ether (40 mL), under nitrogen, was added dropwise at −78° C., n-butyllithium (2.5 M in hexane, 10.36 mL, 25.9 mmol). The mixture was stirred for 1 h after which a solution of 1-benzylpyrrolidin-3-one (3.63 g, 20.7 mmol) in dry diethyl ether (20 mL) was added drop wise. The resulting mixture was stirred for 1 h at −78° C. and then brought to ambient temperature. Aqueous sodium carbonate (10%, 50 mL) was added and the aqueous phase was extracted with ethyl acetate (3×50 mL). The combined organic phase was washed with brine, dried (MgSO4) and evaporated. Purification by flash column chromatography on silica gel (ethyl acetate/isooctane, 1:1) gave the title compound (3.6 g). MS m/z (rel. intensity, 70 eV) 289 (M+, 3), 198 (74), 133 (44), 132 (38), 91 (bp).

Preparation 48

ENANTIOMER E1 OF 3-(2,3-DIFLUOROPHENYL)PYRROLIDIN-3-OL

Preparation according to preparation 4: (+)-1-benzyl-3-(2,3-difluorophenyl)pyrrolidin-3-ol (2.86 g, 9.88 mmol), ammonium formiate (1.25 g, 19.76 mmol), ethanol (50 mL) and palladium on carbon (130 mg). Refluxed for 90 min. Dichloromethane/methyl tert-butyl ether (1:1, 50 mL) was added and the mixture was filtrated through celite, the filtrate was evaporated and purified by flash column chromatography on silica gel (triethylamine/methanol, 0:1 to 1:4) to give the title compound (1.0 g). MS m/z (relative intensity, 70 eV) 199 (M+, bp), 141 (84), 113 (65), 127 (64), 63 (48).

Preparation 49

ENANTIOMER E2 OF 3-(2,3-DIFLUOROPHENYL)PYRROLIDIN-3-OL

Preparation according to preparation 4: (−)-1-benzyl-3-(2,3-difluorophenyl)pyrrolidin-3-ol (5.5 g, 19 mmol), ammonium formiate (3 g, 48 mmol), ethanol (100 mL) and palladium on carbon (300 mg). Refluxed for 35 min. Dichloromethane/tert-butylmethyleter (1:1, 100 mL) was added and the mixture was filtrated through celite, the filtrate was evaporated to give the title compound (4.5 g). MS m/z (relative intensity, 70 eV) 199 (M+100) 141 (82), 113 (61), 124 (59), 63 (45).

The following tests were used for evaluation of the compounds according to the invention.

In Vivo Test: Neurochemistry

Male Sprague-Dawley rats weighing 220-320 g are used throughout the experiments. Sixty (60) minutes following administration of the test substance, the rats are decapitated. Directly after decapitation the brain is removed from the skull and put on a glass petri bowl filled with ice. The limbic system (containing the nucleus accumbens—both the core and shell, most parts of the olfactory tubercle and ventral pallidum) is dissected using two thin, angled tweezers and put directly on foil on dry ice (carbon dioxide −78° C.). The striatum and cortex are then dissected and also put on dry ice. The time from decapitation until the last tissue is dissected varies from four to six minutes. The tissue is weighed using a Sartorius BP3105 connected to a computer and packed in labelled tin foil, then stored in an −80° C. freezer. Great care is taken in order to keep the tissue frozen until the time of neurochemical analysis. Each brain part is subsequently analyzed with respect to its content of monoamines and their metabolites.

The monoamine transmitter substances (NE (norepinephrine), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 μm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 mL/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 mL/min) for the amine system contains citric acid 5 mM, sodium citrate 10 mM, MeOH 9% (v/v), MeCN 10.5% (v/v), decane sulfonic acid 0.45 mM, and EDTA 0.1 mM. Detection potentials relative to Ag/AgCl reference are 0.45 and 0.65V.

In Vivo Test: Microdialysis

Male Sprague-Dawley rats weighing 220-320 g were used throughout the experiments. Before the experiment the animals were group housed, five animals in each cage, with free access to water and food. The animals were housed at least 5 days after arrival prior to surgery and use in the experiments. Each rat was used only once for microdialysis.

We use a modified version (Waters, Lofberg et al. 1994) of the I-shaped probe (Santiago and Westerink 1990). The dialysis membrane we use is the AN69 polyacrylonitrile/sodium methalylsulfonate copolymer (HOSPAL; o.d./i.d. 310/220 μm: Gambro, Lund, Sweden). In the dorsal striatum we use probes with an exposed length of 3 mm of dialysis membrane and in the prefrontal cortex the corresponding length is 2.5 mm. The rats were operated under isoflurane inhalation anesthesia while mounted into a Kopf stereotaxic instrument. Coordinates were calculated relative to bregma; dorsal striatum AP +1, ML ±2.6, DV −6.2; Pf cortex, AP +3.2, 8° ML ±1.2, DV −4.0 according to (Paxinos and Watson 1986). The dialysis probe was positioned in a burr hole under stereotaxic guidance and cemented with phosphatine dental cement.

The rats were housed individually in cages for 40 h before the dialysis experiments, allowing them to recover from surgery and minimizing the risk of drug interactions with the anaesthetic during the following experiments. During this period the rats had free access to food and water. On the day of experiment the rats were connected to a micro perfusion pump via a swivel and were replaced in the cage where they could move freely within its confinements. The perfusion medium was a Ringer's solution containing in mmol/l: NaCl; 140, CaCl2; 1.2, KCl; 3.0, MgCl2; 1.0 and ascorbic acid; 0.04 according to (Moghaddam and Bunney 1989). The pump was set to a perfusion speed of 2 μl/min and 40 μl samples were collected every 20 min.

The monoamine transmitter substances (NE (norepinephrine), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindole-acetic acid), HVA (homovanillic acid)) metabolites are quantified in brain tissue homogenates by HPLC separations and electrochemical detection.

The monoamine transmitter substances (NA, DA, 5-HT) as well as their amine (NM, 3-MT) and acid (DOPAC, 5-HIAA, HVA) metabolites are quantified in micro dialysis samples by HPLC separations and electrochemical detection.

The analytical method is based on two chromatographic separations dedicated for amines or acids. Two chromatographic systems share a common auto-injector with a 10-port valve and two sample loops (5 μl for acids, 20 μl for amines) for simultaneously injection on the two systems. The acids are separated by reverse phase chromatography while the amines are separated by reverse phase ion pairing preceded by a reverse phase separation in a column switching configuration.

Three separation columns (Luna C18(2), dp 3 μm, 2 mm i.d., Phenomenex) of different lengths are used. Electrochemical detection is accomplished on glassy carbon electrodes (MF-1000, Bioanalytical Systems, Inc.).

The aqueous mobile phase (0.6 mL/min) for the acid system contains Citric Acid 40 mM, di-Potassium hydrogen phosphate 10 mM, MeOH 8% (v/v) and EDTA 0.1 mM. Column length is 30 mm. Detection potential relative to Ag/AgCl reference is 0.70V.

The aqueous ion pairing mobile phase (0.4 mL/min) for the amine system contains Citric Acid 5 mM, Sodium Citrate 10 mM, MeCN 10% (v/v), THF 4% (v/v), Dodecane Sulfonic Acid 0.05 mM, and EDTA 0.1 mM. Column length is 50 mm. Detection potentials relative to Ag/AgCl reference are 0.45 and 0.65V.

The aqueous mobile phase (0.4 mL/min) for the coupled reverse phase separation is identical to the ion pairing mobile phase, but Dodecane Sulfonic Acid is excluded.

Column length is 20 mm. Minor modifications in analytical conditions may occur over time for optimisation.

After the experiment the rats were uncoupled from the perfusion pump and decapitated. Their brains were rapidly taken out and fixed in Accustain solution (Sigma, Sweden) for subsequent inspection of probe localisation. The Animal Ethics Committee in Göteborg, Sweden approved the procedures applied in these experiments.

For comparative example 16 of reference 1 an earlier analytical procedure was used. In this procedure the amines are separated without column switching and the ion pairing conditions are slightly different optimised. For comparative example 16 in reference 1, anesthesia was induced by injection of ketamine and xylazine, and the brains were fixed in Neo-fix solution (Kebolab, Sweden) for subsequent inspection of probe localisation.

REFERENCES

Moghaddam, B. and B. S. Bunney (1989). "Ionic Composition of Microdialysis Perfusing Solution Alters the Pharmacological Responsiveness and Basal Outflow of Striatal Dopamine." J. Neurochem. 53: 652-654.

Paxinos, G. and C. Watson (1986). The Rat Brain in Stereotaxic Coordinates. New York, Academic Press.

Santiago, M. and B. H. C. Westerink (1990). "Characterization of the in vivo release of dopamine as recorded by different types of intracerebral microdialysis probes." Naunyn-Schmiedeberg's Arch. Pharmacol. 342: 407-414.

Waters, N., L. Lofberg, S. Haadsma-Svensson, K. Svensson, C. Sonesson and A. Carlsson (1994). "Differential effects of dopamine D2 and D3 receptor antagonists in regard to dopamine release, in vivo receptor displacement and behaviour." J Neural Transm Gen Sect 98(1): 39-55.

The invention claimed is:

1. A compound of Formula (2):

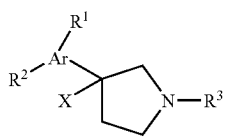

(2)

any of its stereoisomers or any mixture of its stereoisomers, or an N-oxide thereof, or a pharmaceutically acceptable salt thereof, wherein;
Ar is selected from the group consisting of phenyl, thiophenyl, furanyl, 2-pyrimidinyl, oxazoyl and thiazolyl;
$R^1$ is selected from the group consisting of F and Cl;
$R^2$ is selected from the group consisting of F and Cl;
$R^3$ is selected from the group consisting of H, Me, Et, n-Pr, i-Pr, n-Bu, i-Bu, s-Bu, t-Bu, cyclopropylmethyl, $CFH_2CH_2CH_2$—, $CF_2HCH_2CH_2$—, $CF_3CH_2CH_2$—, allyl and $CH_3OCH_2CH_2$—; and
X is selected from the group consisting of F or OH; provided that when X is OH, $R^3$ is not H.

2. The compound according to claim 1, wherein Ar is phenyl.

3. The compound according to claim 1, of Formula (3):

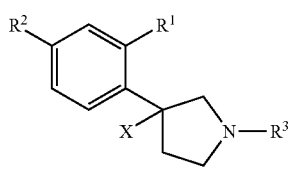

(3)

or Formula (4):

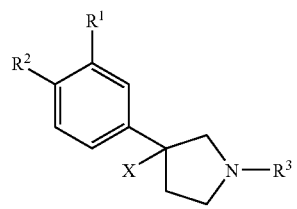

(4)

or Formula (5):

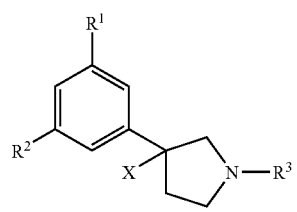

(5)

or Formula (6):

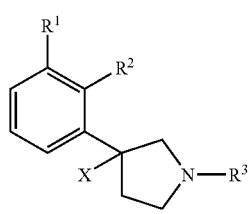

(6)

or a pharmaceutically acceptable salt thereof.

4. The compound according to claim 1, wherein $R^1$ is F.

5. The compound according to claim 1, wherein $R^2$ is F and $R^3$ is H or Me.

6. The compound according to claim 1, wherein $R^3$ is Et or n-Pr.

7. The compound according to claim 1, wherein $R^3$ is Me.

8. The compound according to claim 1, said compound is in the (+)-enantiomeric form.

9. The compound according to claim 1, said compound is in the (−)-enantiomeric form.

10. A pharmaceutical composition comprising a therapeutically effective amount of the compound according to claim 1, any of its stereoisomers or any mixture of its stereoisomers, or an N-oxide thereof, or a pharmaceutically acceptable salt thereof, together with one or more pharmaceutically acceptable carriers or diluents.

11. A method for treatment of dementia, age-related cognitive impairment, an Autism spectrum disorder, ADHD, Cerebral Palsy, Gilles de la Tourette's syndrome, a cognitive disorder occurring as part of the core symptoms of schizophrenia, schizophrenia, a schizophreniform disorder, depression, bipolar disorder, generalized anxiety disorder (GAD), specific phobia, panic disorder (PD), or a sleep disorder in a living animal body, including a human, which method comprises the step of administering to such a living animal body in need thereof a therapeutically effective amount of the compound according to claim 1, or any of its stereoisomers or any mixture of its stereoisomers, or an N-oxide thereof, or a pharmaceutically acceptable salt thereof.

12. The compound according to claim 1, which is
(−)-3-(3,5-difluorophenyl)-1-ethylpyrrolidin-3-ol;
(+)-3-(3,5-difluorophenyl)-1-ethylpyrrolidin-3-ol;
3-(3-chloro-4-fluorophenyl)-1-ethylpyrrolidin-3-ol;
3-(2,3-difluorophenyl)-1-ethylpyrrolidin-3-ol;
3-(3-chloro-5-fluorophenyl)-1-ethylpyrrolidin-3-ol;
3-(3,5-dichlorophenyl)-1-ethylpyrrolidin-3-ol;
3-(3,4-difluorophenyl)-1-propylpyrrolidin-3-ol;
3-(3,5-difluorophenyl)-1-ethylpyrrolidin-3-ol;
3-(3,5-difluorophenyl)-1-propylpyrrolidin-3-ol;
3-(3,4-dichlorophenyl)-1-ethylpyrrolidin-3-ol;
3-(3,5-difluorophenyl)-3-fluoro-1-methylpyrrolidine;
3-(3,4-difluorophenyl)-1-ethylpyrrolidin-3-ol;
3-(3,5-difluorophenyl)-3-fluoropyrrolidine;
3-(3,5-dichlorophenyl)-3-fluoropyrrolidine;
3-(2,4-difluorophenyl)-1-methylpyrrolidin-3-ol;
3-(3,4-difluorophenyl)-1-methylpyrrolidin-3-ol;
3-(2,3-dichlorophenyl)-1-ethylpyrrolidin-3-ol;
3-(3,5-difluorophenyl)-1-methylpyrrolidin-3-ol;
3-(3-chloro-2-fluorophenyl)-1-methylpyrrolidin-3-ol;
3-(3-chloro-2-fluorophenyl)-1-ethylpyrrolidin-3-ol;
3-(3-chloro-4-fluorophenyl)-1-propylpyrrolidin-3-ol;
3-(3-chloro-5-fluorophenyl)-1-propylpyrrolidin-3-ol;
3-(2,3-difluorophenyl)-3-fluoropyrrolidine;
(+)-3-(3,4-difluorophenyl)-1-ethylpyrrolidin-3-ol;
(+3-(3,4-difluorophenyl)-1-ethylpyrrolidin-3-ol;
3-(3-chloro-5-fluorophenyl)-1-methylpyrrolidin-3-ol;
(+)-3-(3,4-difluorophenyl)-1-propylpyrrolidin-3-ol;
(+3-(3,4-difluorophenyl)-1-propylpyrrolidin-3-ol;
(+)-3-(3,5-difluorophenyl)-1-propylpyrrolidin-3-ol;
(+3-(3,5-difluorophenyl)-1-propylpyrrolidin-3-ol;
(−)-3-(3-chloro-5-fluorophenyl)-1-ethylpyrrolidin-3-ol;
(−)-3-(2,3-difluorophenyl)-1-ethylpyrrolidin-3-ol;
(−)-3-(2,3-difluorophenyl)-1-propylpyrrolidin-3-ol;
(+)-3-(2,3-difluorophenyl)-1-propylpyrrolidin-3-ol;
(+)-3-(3-chloro-2-fluorophenyl)-1-ethylpyrrolidin-3-ol;
(+)-3-(2,3-difluorophenyl)-1-ethylpyrrolidin-3-ol;
(−)-3-(3-chloro-2-fluorophenyl)-1-ethylpyrrolidin-3-ol;
(−)-1-butyl-3-(2,3-difluorophenyl)pyrrolidin-3-ol;
(−)-3-(2,3-difluorophenyl)-1-isobutylpyrrolidin-3-ol;
(−)-3-(2,3-difluorophenyl)-1-methylpyrrolidin-3-ol;
(−)-1-allyl-3-(2,3-difluorophenyl)pyrrolidin-3-ol;
(−)-3-(2,3-difluorophenyl)-1-(2-methoxyethyl)pyrrolidin-3-ol;
(−)-1-butyl-3-(3,5-difluorophenyl)pyrrolidin-3-ol;
(−)-1-allyl-3-(3,5-difluorophenyl)pyrrolidin-3-ol;
(−)-3-(3,5-difluorophenyl)-1-(2-methoxyethyl)pyrrolidin-3-ol;
(−)-3-(3,5-difluorophenyl)-1-isobutylpyrrolidin-3-ol;
(−)-3-(3,5-difluorophenyl)-1-methylpyrrolidin-3-ol;
(−)-3-(2,3-difluorophenyl)-1-(3,3,3-trifluoropropyl)pyrrolidin-3-ol;
(−)-1-(cyclopropylmethyl)-3-(2,3-difluorophenyl)pyrrolidin-3-ol;
3-(3,4-difluorophenyl)-1-isopropylpyrrolidin-3-ol;
(+)-1-butyl-3-(3,5-difluorophenyl)pyrrolidin-3-ol;
(+)-3-(3,5-difluorophenyl)-1-methylpyrrolidin-3-ol;
(+)-3-(3,5-difluorophenyl)-1-isobutylpyrrolidin-3-ol;
(+)-3-(3,5-difluorophenyl)-1-(2-methoxyethyl)pyrrolidin-3-ol;
(+)-1-allyl-3-(3,5-difluorophenyl)pyrrolidin-3-ol;
(+)-3-(3-chloro-2-fluorophenyl)-1-methylpyrrolidin-3-ol;
(−)-3-(3-chloro-2-fluorophenyl)-1-methylpyrrolidin-3-ol;
(+)-1-butyl-3-(2,3-difluorophenyl)pyrrolidin-3-ol;
(+)-3-(2,3-difluorophenyl)-1-methylpyrrolidin-3-ol;
(+)-3-(2,3-difluorophenyl)-1-(2-methoxyethyl)pyrrolidin-3-ol;
(+)-3-(2,3-difluorophenyl)-1-isobutylpyrrolidin-3-ol;
(+)-1-allyl-3-(2,3-difluorophenyl)pyrrolidin-3-ol;
(+)-3-(2,3-difluorophenyl)-1-(3,3,3-trifluoropropyl)pyrrolidin-3-ol;
(+)-1-(cyclopropylmethyl)-3-(2,3-difluorophenyl)pyrrolidin-3-ol;
(−)-3-(3-chloro-5-fluorophenyl)-1-methylpyrrolidin-3-ol;
(+)-3-(3-chloro-5-fluorophenyl)-1-methylpyrrolidin-3-ol; or
(+)-3-(3-chloro-5-fluorophenyl)-1-ethylpyrrolidin-3-ol;
or an n-oxide thereof, or a pharmaceutically acceptable salt thereof.

13. The compound according to claim 1, which is
(+)-3-(2,3-difluorophenyl)-1-ethylpyrrolidin-3-ol;
or an n-oxide thereof, or a pharmaceutically acceptable salt thereof.

\* \* \* \* \*